(12) United States Patent
Park et al.

(10) Patent No.: US 7,811,790 B2
(45) Date of Patent: Oct. 12, 2010

(54) POLYMYXIN SYNTHETASE AND GENE CLUSTER THEREOF

(75) Inventors: Seung-Hwan Park, Gongju-si (KR); Jihyun F. Kim, Taejeon-si (KR); ChoongHwan Lee, Taejeon-si (KR); Soo-Keun Choi, Taejeon-si (KR); Heayoung Jeong, Taejeon-si (KR); Seong-Bin Kim, Taejeon-si (KR); Yon Kyoung Park, Taejeon (KR); Rumi Kim, Taejeon-si (KR); Choong-Min Ryu, Taejeon-si (KR); Soo-Young Park, Taejeon-si (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 8 days.

(21) Appl. No.: 12/096,789

(22) PCT Filed: Nov. 8, 2006

(86) PCT No.: PCT/KR2006/004665

§ 371 (c)(1),
(2), (4) Date: Jun. 9, 2008

(87) PCT Pub. No.: WO2007/066906

PCT Pub. Date: Jun. 14, 2007

(65) Prior Publication Data

US 2009/0226964 A1 Sep. 10, 2009

(30) Foreign Application Priority Data

Dec. 9, 2005 (KR) .................. 10-2005-0120878

(51) Int. Cl.
*C12P 21/06* (2006.01)
*C12N 9/00* (2006.01)
*C12N 15/00* (2006.01)
*C12N 1/20* (2006.01)
*C07H 21/04* (2006.01)

(52) U.S. Cl. .............. 435/69.1; 435/183; 435/252.3; 435/320.1; 536/23.2

(58) Field of Classification Search .............. None
See application file for complete search history.

(56) References Cited

OTHER PUBLICATIONS

Beck et al. (2003) Novel pyrazine metabolites found in polymyxin biosynthesis by *Paenibacillus polymyxa*. FEMS Microbiology Letters, 220:67-73.
Paulus (1975) Polymyxin synthetase: L-2,4-diaminobutyrate activating enzyme. Methods Enzymol. 43:579-84.
Balakrishnan et al. (1980) Biosynthesis of polymyxin by *Bacillus Polymyxa*. II. On the nature and interaction of the multienzyme complex with the end product polymyxin. Archives of Biochemistry and Biophysics. 200(1):45-54.
Komura et al. (1979) Partial purification and properties of L-2,4-diaminobutyric acid activating enzyme from a polymyxin E producing organism. J. Biochem. 86:1013-1021.
Choi, et al., Identification of a Polymyxin Synthetase Gene Cluster of *Paenibacillus polymyxa* and Heterologous Expression of the Gene in *Bacillus subtilis*, Journal of Bacteriology, May 2009, pp. 3350-3358, vol. 191, No. 10, American Society for Microbiology.

*Primary Examiner*—Nashaat T Nashed
(74) *Attorney, Agent, or Firm*—Greenlee Sullivan P.C.

(57) ABSTRACT

The present invention relates to a polymyxin synthetase isolated from Gram-positive *Paenibacillus* sp. and a gene cluster encoding the same, more precisely a polymyxin synthetase isolated from *Paenibacillus polymyxa* E681, a gene cluster encoding thereof and a preparation method of polymyxin or its derivatives using the gene cluster. The polymyxin synthetase of the present invention can be effectively used for the increase of productivity of polymyxin and the development of a novel antibiotic.

14 Claims, 3 Drawing Sheets

(A)

(B)

A: adenylation domain
C: condensation domain
E: epimerization domain
T: thiolation domain
TE: termination domain

US 7,811,790 B2

POLYMYXIN SYNTHETASE AND GENE CLUSTER THEREOF

CROSS REFERENCE TO RELATED APPLICATIONS

This application is the National Stage filed under 35 U.S.C. 371 of International Application No. PCT/KR2006/0044665, filed Nov. 8, 2006, which claims priority to KR 10-2005-120878, filed Dec. 9, 2005.

TECHNICAL FIELD

The present invention relates to a polymyxin synthetase isolated from Gram-positive *Paenibacillus* sp. and a gene cluster encoding thereof, more precisely a polymyxin synthetase isolated from *Paenibacillus polymyxa* E681, a gene cluster encoding thereof and a preparation method of polymyxin or its derivatives using the gene cluster.

BACKGROUND ART

Non-ribosomal peptide synthetase (referred as 'NRPS' hereinafter) is organized by at least one ORF (open reading frame) forming NRPS complex, and each NRPS or NRPS subunit comprises one or more modules. A module is defined as the catalytic unit that incorporates one building block (for example, one amino acid) into the growing chain. Order and specificity of the modules within the NRPS determine the sequence and structure of the peptide product. Thus, NRPS which is not involved in ribosomal RNA translation used to be carried out by genetic code can produce peptides of wider structural diversity than those peptides translated from RNA template by ribosome. The peptides produced by NRPS can be further modified by the connection between hydroxyl acid and D- and L-amino acid, mutation and oxidation in main peptide chain forming linear, cyclic or branched cyclic structure, acylation, glycosylation, N-methylation and heterocyclic ring formation.

Polymyxin synthetase, one of NRPSs, stepwisely combines each amino acid monomer forming polymyxin and if necessary transforms the amino acid to complete the entire amino acid chain and to form a ring structure in order to synthesize a peptide antibiotic. Each module of NRPS is organized by at least three domains, which are A, C, and T domains. A domain (adenylation domain) plays a role in the selection and activation of an amino acid monomer, C domain (condensation domain) catalyzes peptide bond formation and T domains (thiolation domain, also called PCP) is involved in rotating phosphopantheteine group to incorporate an amino acid monomer into the growing peptide chain.

Recently, the tertiary structure of A domain recognizing phenylalanine of gramicidin biosynthesis gene has been identified, in which a specific amino acid binding site contains 8 amino acid residues (Conti E. et al., 1997. EMBO J. 16: 4174-4183). The amino acid sequence of this A domain was compared with that of the conventional A domain, as a result this A domain had high homology in 8 amino acid residues with the conventional A domain. Thus, analyzing the 8 amino acid residues may lead to the understanding of the association of a specific A domain with an amino acid (Challis G. L. et al., 2000. Chem. Biol. 7: 211-224).

In addition to these major domains, there are E domain (epimerization domain) playing a role in conversion of L-amino acid into D-amino acid and TE domain (termination domain), which are characterized by a specific amino acid motif.

A novel enzyme characterized by specificity can be designed by the modification of numbers and locations of modules at DNA level by genetic engineering and in vivo recombination techniques. For example, a domain originated from heterologous NRPS is substituted by using a recombinant technique (Schneider et al., Mol. Gen. Genet., 257, pp. 308-318, 1998) or a module can be designed to have specificity by changing residues forming the substrate binding pocket of A domain (Cane et al., Chem. Biol. vol. 6, p. 319-325, 1999).

Unlike other general peptides ribosomally translated, polymyxin is an antibiotic isolated from *Bacillus* sp. or *Paenibacillus* sp., which is produced by non-ribosomal peptide synthetase (Marahiel M. A. et al., 1997, Chem. Rev. 97, 2651-2673; Doekel S. et al., 2001, Metab. Eng. 6, 64-77).

The molecular weight of polymyxin is approximately 1200 Da (1.2 kDa) (Storm D. R. et al., Ann Rev. Biochem. 1977; 46:723-763). The basic structure of polymyxin is polyketidic peptide ring comprising 8~10 amino acids and 2,4-diaminobutyric acid (Dab) at high concentration. Fatty acid is also attached on the peptide ring, which is preferably 6-methyoctanoic acid or 6-methylheptanoic acid (see FIG. 4). This structure favors solubility of polymyxin, suggesting that polymyxin is soluble in both water and an organic solvent.

Polymyxin is an antibiotic that is able to induce apoptosis by changing permeability of cell membrane and is functioning according to the following mechanisms.

First, polyketidic peptide ring of polymyxin changes the bridge between magnesium and calcium that stabilizes lipopolysaccharide of cell membrane to be bound to the cell. Then, lipopolysaccharide of cell membrane is reacted with fatty acid residue of polymyxin to make the linkage between polymyxin and cell membrane strong and tight. At last, polymyxin is incorporated into the outer membrane of cell, resulting in the destruction of the cell membrane (Hermsen E. D. et al., 2003, Infect. Dis. Clin. N. Am. 17: 545-562).

Polymyxin B was first isolated from *Paenibacillus polymyxa* in 1947 and since then 15 polymyxins have been reported (Storm D. R., et al., 1977, Annu. Rev. Biochem., 46: 723-763; Silaev, A. B. et al., 1975, Zh. Obshch. Khim. 45: 2331-2337; Martin N. I. et al., 2003, J. Biol. Chem. 278: 13124-13132). The polymyxin based antibiotic 'polymyxin B sulfate' killed 88% of *Pseudomonas aeruginosa* at the concentration of 0.01 µg/ml. Polymyxin E showed lethal effect at the concentration of 0.1 µg/ml. Polymyxin B and polymyxin E exhibited lethal effect on most *Escherichia coli* strains and *Pseudomonas aeruginosa* at the concentration under 2 µg/ml, in addition to on every *Enterobacter, Salmonella, Shigella, Pasteurella, Brucella* and *Bordetella*. However, both polymyxin B and E showed no lethal effect on *Proteus, Serratia, Providencia* and *Edwardsiella* even at the higher concentrations than 200 µg/ml. They had no effect on gram-positive bacteria, fungi and anaerobic bacteria, either (Nord N. M. et al., 1964, N. Engl. J. Med. 270: p. 1030-1035).

Thus, polymyxin had been used as a therapeutic agent for many diseases caused by pathogenic microorganisms until early 1970. But, it carried serious side effects such as fever, eruption and pain and induced severe neurotoxicity and hepatotoxicity (Pedersen M. F. et al., 1971, Invest. Urol. 9: p. 234-237). So, it has been replaced with other antibiotics with improved stability and most recently it is only being applied on local wounds as a form of ointment.

According to the increased use of antibiotics, pathogenic microorganisms having resistance to those antibiotics have been frequently noticed. In the midst, polymyxin draws our attention since it has excellent bactericidal effect on Gram-negative bacteria, in particular *Pseudomonas aeruginosa* and

*Acinetobacter baumannii* exhibiting resistance against β-lactam, aminoglycoside and fluoroquinolone antibiotics.

Levin, et al reported that colistin (polymyxin E) was intravenously injected to 60 patients infected with *Pseudomonas aeruginosa* and *Acinetobacter baumannii* exhibiting resistance against the conventional antibiotics and as a result 58% of the patients were improved (Levin A. S. et al. 1999. Clin. Infect. Dis. 28:1008-1011). And there is another report by Stein, et al. saying that 3 osteomyelitis patients infected with *Pseudomonas aeruginosa* having resistance against almost all antibiotics were improved by the treatment of colistin (Stein A. et al., 2002, Clin. Infect. Dis. 35: p. 901-902). In another report, meningitis caused by *Acinetobacter* having resistance against antibiotics was also successfully treated by colistin (Jimenez-Mejias M. E. et al., 2002. Eur. J. Clin. Microbiol. Infect. Dis. 21: p. 212-214). Another report says that ventriculis caused by antibiotics-resistant *Klebsiella pneumoniae* was successfully treated by polymyxin B (Segal-Maurer S. et al., 1999, Clin. Infect. Dis. 28: p. 1134-1138).

As described hereinbefore, polymyxin seems to have therapeutic effect on Gram-negative bacteria having resistance against the conventional antibiotics, so that it is in increasing demand.

It had been tried to introduce an antibiotic biosynthesis gene into an industrially mass-productive strain in order to increase antibiotic productivity (Eppelmann K. et al., 2001. J. Biol. Chem. 276: p. 34824-34831; Pfeifer B. A. et al., 2001, Microbiol. Mol. Biol. Rev. 65: 106-118) and in fact it was confirmed that the substitution of a promoter of the antibiotic biosynthesis gene with a stronger one resulted in the increase of productivity (Tsuge K. et al., 2001. J. Bacteriol. 183: p. 6265-6273). There is an attempt to develop a novel antibiotic by re-constructing modules or domains of an antibiotic biosynthesis gene (Mootz H. D. et al., 2000. Proc. Natl. Acad. Sci. USA 97: p. 5848-5853; Ferra F. D. et al., 1997. J. Biol. Chem. 272: p. 25304-25309) or substituting a specific amino acid of the domains (Eppelmann K. et al., Biochemistry 41: p. 9718-9726). However, no polymyxin biosynthesis gene has been identified so far, therefore it had hardly been tried to increase productivity or develop a novel antibiotic based on the above mentioned techniques.

Therefore, it is important to identify a polymyxin biosynthesis gene and secure the information on the gene to increase production of polymyxin or develop polymyxin with less side effects and polymyxin based novel antibiotics.

The present inventors isolated, purified and analyzed polymyxin from *Paenibacillus polymyxa* E681. And the inventors confirmed that the strain produced polymyxin and found out and isolated a gene cluster encoding NRPS by sequencing the entire nucleotide sequence. The present inventors finally completed this invention by confirming with the domain analysis that the gene cluster was polymyxin biosynthesis gene.

DISCLOSURE

Technical Problem

It is an object of the present invention to provide a polymyxin synthetase isolated from *Paenibacillus polymyxa* E681, a gene cluster encoding the enzyme, and a preparation method for polymyxin and its derivatives using the gene cluster.

Technical Solution

The present invention provides a gene cluster encoding one or more polypeptides involved in polymyxin synthesis.

The present invention also provides a polymyxin synthetase encoded by the gene cluster.

The present invention further provides a recombinant vector containing the gene cluster.

The present invention also provides a host cell transformed by the above vector.

The present invention also provides an amino acid additional module of the polymyxin synthetase, in which A-T-E, C-A-T, C-A-T-C, C-A-T-E, C-A-T-TE or A-T-TE domains are combined stepwisely.

The present invention also provides a gene encoding each amino acid additional module.

The present invention also provides a polymyxin synthetase produced by the combination of the amino acid additional modules.

And, the present invention provides a preparation method of polymyxin or its derivatives comprising the following steps:

1) Inserting a gene cluster encoding the polymyxin synthetase into an expression vector;
2) Transforming a host cell with the expression vector containing the gene cluster of step 1);
3) Culturing the transformant of step 2); and
4) Isolating and purifying polymyxin or its derivatives from the culture product of step 3).

The descriptions for the terms used in the present invention are given hereinafter.

Non-ribosomal peptide synthetase (NRPS): composed of one or more ORFs (open reading frame) forming NRPS complex. Each NRPS or NRPS subunit contains one or more modules.

Module: a catalytic unit that incorporates a building block (ex: an amino acid) into the growing peptide chain. NRPSs produced peptides of enormous structural diversity, compared with ribosomally synthesized peptides.

Polymyxin: an antibiotic isolated from *Bacillus* sp or *Paenibacillus* sp, which is generated by NRPS not by ribosomal synthesis after being encoded.

Polymyxin synthetase: one of NRPSs, which combines each amino acid monomer forming polymyxin stepwisely and modifies the amino acid to complete the entire amino acid chain and to form a ring structure to produce a peptide antibiotic.

NRPS module: composed of A, C and T domains and additional E and TE domains.

A domain (adenylation domain) plays a role in selection and activation of an amino acid monomer and C domain (condensation domain) catalyzes a peptide bond formation, while T domain (thiolation domain, PCP) is involved in rotating phophopantheteine group to incorporate the amino acid monomer into growing polypeptide chain, E domain (epimerization) plays a role in conversion of L-amino acid into D-amino acid, and TE domain (termination domain) terminates the addition reaction of amino acids.

Hereinafter, the present invention is described in detail.

The present invention provides a gene cluster encoding one or more polypeptides involved in polymyxin synthesis. The present invention also provides a polymyxin synthetase encoded by the gene cluster.

The gene cluster is preferably isolated from *Paenibacillus polymyxa* E681.

The polymyxin herein is preferably polymyxin B, E or M and more preferably polymyxin M having polyketidic ring structure characterized by the stepwise binding of L-DAB (diaminobutyric acid), L-Thr (threonine), L-DAB and L-DAB to the amino group of 6-MOA (methyloctanoyl acid) and the location of D-Phe (phenylalanine) or D-Leu (leucine) on the $6^{th}$ and the location of L-Leu, L-Thr, L-Ile (isoleucine) or L-Phe on the $7^{th}$ site from the above amino group (see FIG. 1).

Polymyxin synthetase is one of NRPSs composed of one or more polypeptides, which is encoded by a gene cluster. The "gene cluster" herein is defined as the genome segment of a microorganism containing every gene necessary for the synthesis of secondary metabolites.

Particularly, the polymyxin synthetase consists of the polypeptide Pmx A represented by SEQ. ID. NO: 4, the polypeptide Pmx B represented by SEQ. ID. NO: 5, and the polypeptide Pmx E represented by SEQ. ID. NO: 6, but not always limited thereto. The variants of the above polypeptides, which are polypeptides having functional identity even though there are addition, deletion or substitution of one or more modules, domains and/or amino acids, can also be included. That is, every genes encoding Pmx A, Pmx B, Pmx E and their variants are included in the criteria of the invention, and particularly those nucleotide sequences represented by SEQ. ID. NO: 1, NO: 2 and NO: 3 are preferred.

The present inventors sequenced the nucleotide sequence of *Paenibacillus polymyxa* E681 genome by using whole-genome shotgun sequencing strategy. As a result, it was confirmed that *Paenibacillus polymyxa* E681 genome is approximately 5.4 Mbps in length and has a single circular chromosome. The present inventors also identified a polymyxin biosynthetic gene cluster from the genome above.

Approximately 4800 genes encoding proteins have been identified from the nucleotide sequence of E681 genome by using Critica (Badger J. H. and Olsen G. J., 1999, Mol. Biol. Evol. 16, 512), glimmer (Delcher A. L. et al., 1999, Nucleic Acids Res. 27, 4636) and zcurve (Guo F.-B. et al., 2003, Nucleic Acids Res. 31, 1780) programs. To investigate the functions of each gene product, the genes were translated into amino acid sequences and compared with sequences in the protein sequence database (Altschul S. F. et al., 1997, Nucleic Acids Res. 25: 3389-3402). Next, domain and protein family analysis (Bateman A. et al., 2004, Nucleic Acids Res. 32 (Database issue):D138-141; Haft D. H. et al., 2003, Nucleic Acids Res. 31:371-373), motif and pattern screening (Hulo N. et al., 2004, Nucleic Acids Res. 32 (Database issue):D134-137) and protein site prediction analysis (Gardy J. L. et al., 2003, Nucleic Acids Res. 31:3613-3617) were performed.

From the above screening, at least 4 NRPS gene clusters encoding 4 different antibiotic synthetases have been identified.

The substrate specificity of adenylation (A) domain of each gene cluster was compared with the chart showing active amino acids associated with A domain substrate specificity prepared by Challis et al (Challis G. L. et al., 2000, Chem. Biol. 7: p. 211-224). As a result, one of the gene clusters was identified as the gene cluster encoding polymyxin synthetase (see FIG. 2).

Each polypeptide of the polymyxin synthetase of the present invention contains one or more modules and each module is preferably organized by at least 2 domains selected from a group consisting of A, C, T, E and TE domains.

In polymyxin synthetase organized with PmxA, PmxB and PmxE, the fifth module of PmxE, C domain joins in the fifth module 'A-T-E' of PMXA, and the last C domain of the forth module of PmxA joins A-T-TE of PmxB. PmxC and PmxD were proved not to be involved in polymyxin synthesis but expected to be involved in polymyxin secretion.

Polymyxin is synthesized by completing polyketidic peptide ring by the stepwise binding of L-DAB (diaminobutyric acid), L-Thr (threonine), L-DAB, L-DAB, and L-DAB to the amino group of 6-MOA (methyloctanoyl acid) by Pmx E polypeptide module (domain) and locating D-Phe (phenylalanine) or D-Leu (leucine) on the $6^{th}$ site and then locating L-Leu, L-Thr, L-Ile (isoleucine) or L-Phe on the $7^{th}$ site, followed by the stepwise binding of L-DAB and L-DAB, and at last linking L-Thr by Pmx B polypeptide module (domain) (see FIG. 1A).

The polymyxin synthetase predicted by the nucleotide sequence of the gene, as shown in FIG. 4, enabled the prediction of polymyxin B, polymyxin E or polymyxin M. Considering that polymyxin isolated in Example 1 was polymyxin M, the gene cluster of the invention was presumed to be polymyxin M synthetase.

A novel polymyxin synthetase having a different specificity can be derived from the gene cluster of the invention by genetic alteration such as changing number or position of a module or a domain in the gene cluster. For example, heterologous NRPS originated domain was substituted (Schneider et al., Mol. Gen. Genet., 257, p. 308-318, 1998) or a residue forming substrate binding pocket of A domain was replaced to design a novel substrate specificity (Cane and Walsh, Chem. Biol. vol. 6, p. 319-325, 1999), or structural modification was performed by addition, substitution or deletion of one or more modules, domains or amino acids or by the linkage between D- and L-amino acid and hydroxyl acid, mutation and oxidation of peptide chain, acylation, glycosylation, N-methylation and heterocyclic ring formation.

Therefore, the gene provided by the present invention can be effectively used for the development of polymyxin with minimized side effects and its derivatives or a novel antibiotic according to the above method.

The present invention also provides a recombinant vector containing the gene cluster of the invention and a host cell transformed with the vector.

The gene cluster encoding polymyxin synthetase of the invention can be cloned into such vectors as BAC, plasmid, and fosmid, and the vector can be introduced into a relevant host cell to produce a polymyxin antibiotic.

In the present invention, *Paenibacillus polymyxa, E. coli*, and *Bacillus subtillis* are preferably used as host cells. A recombinant vector can be introduced into such host cells by a conventional method well-known to those in the art including heat-shock method or electric-shock method. It is also well understood to those in the art that different strains can be used as host cells according to the purpose of expression or various vectors.

The present invention also provides an amino acid additional module of polymyxin synthetase A-T-E, C-A-T, C-A-T-C, C-A-T-E C-A-T-TE or A-T-TE and a gene encoding each of the amino acid additional module.

Each module forming a polypeptide is described herein. First, Pmx A polypeptide is organized by the following 4 modules, The first module: A(adenylation)-T(thiolation)-E(epimerization) domain;

The second module and the third modules: C(condensation)-A-T domain; and

The forth module: C-A-T-C domain.

Pmx B polypeptide comprises one module which is A-T-TE(termination) domain,

And Pmx E polypeptide is organized by the following 5 modules,

The first and the second modules: C-A-T domain;
The third module: C-A-T-E domain;
The forth module: C-A-T domain; and
The fifth module: C-A-T-C domain (see FIG. 3).

Genes encoding each domain and module of Pmx A, Pmx B and Pmx E are those represented by SEQ. ID. NO: 7~NO: 66, in which linker genes combining each domain are also included. The SEQ. ID. NO. of each domain is presented in Table 1.

The present invention also provides a polymyxin synthetase produced by the combination of the amino acid additional modules.

Each polymyxin synthetase is formed by the combination of modules arranged as A-T-E, C-A-T, C-A-T-C, C-A-T-E, C-A-T-TE or A-T-TE. Therefore, the construction of such recombinant expression vector that contains the combination of gene corresponding each module leads to the diversity of polymyxin synthetases.

The present invention also provides a preparation method of polymyxin or its derivatives comprising the following steps:

1) Inserting a gene cluster encoding the polymyxin synthetase into an expression vector;
2) Transforming a host cell with the expression vector containing the gene cluster of step 1);
3) Culturing the transformant of step 2); and
4) Isolating and purifying polymyxin or its derivatives from the culture product of step 3).

DESCRIPTION OF DRAWINGS

The application of the preferred embodiments of the present invention is best understood with reference to the accompanying drawings, wherein:

FIG. 1(A) is a representative diagram of polymyxin and FIG. 1(B) illustrates the structure of polymyxin M isolated from *Paenibacillus polymyxa* E681.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Isolation and Analysis of Polymyxin from *Paenibacillus polymyxa*

<1-1> Culture of *Paenibacillus polymyxa*

Paenibacillus *polymyxa* E681 was cultured in the medium designed by Paulus and Gray (Paulus H and Gray E. 1964, J. Biol. Chem. 239:865-871) under aerobic condition at 25° C. with 180 rpm for 3 days, followed by centrifugation (7000 rpm, 10 min) to separate supernatant.

<1-2> Identification of Polymyxin by LC/MS Analyzing System

The composition of the supernatant was analyzed by LC/MS system.

LC/MS was performed using high pressure liquid chromatography system provided by Thermo Electron Co. (USA) and ion spectrometer. The sample proceeded to reversed-phase column (YMC Hydrosphere C18 column) and analyzed in a mixed solvent of acetonitrile and water containing 0.1% formic acid (0.2 ml/min).

As a result, $(M+H)^+$ ion peak was 1158, and the actual molecular weight was confirmed to be 1157, which is the same molecular weight of the conventional polymyxin M.

Figure 1:
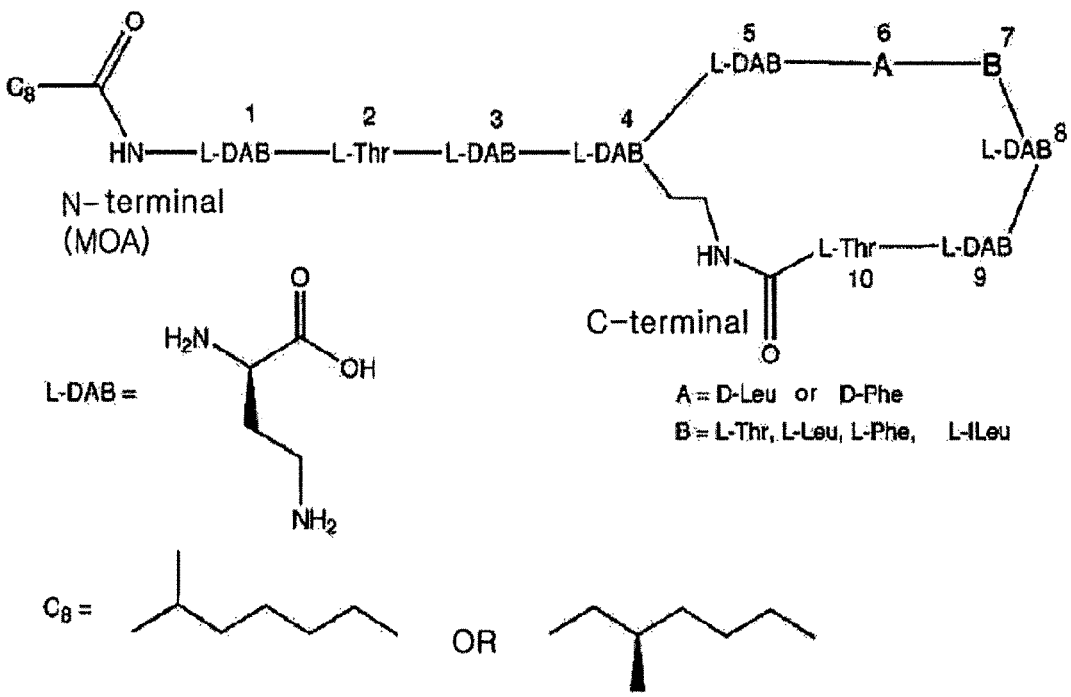
FIG. 1 illustrates the structure of polymyxin.
Figure 1:
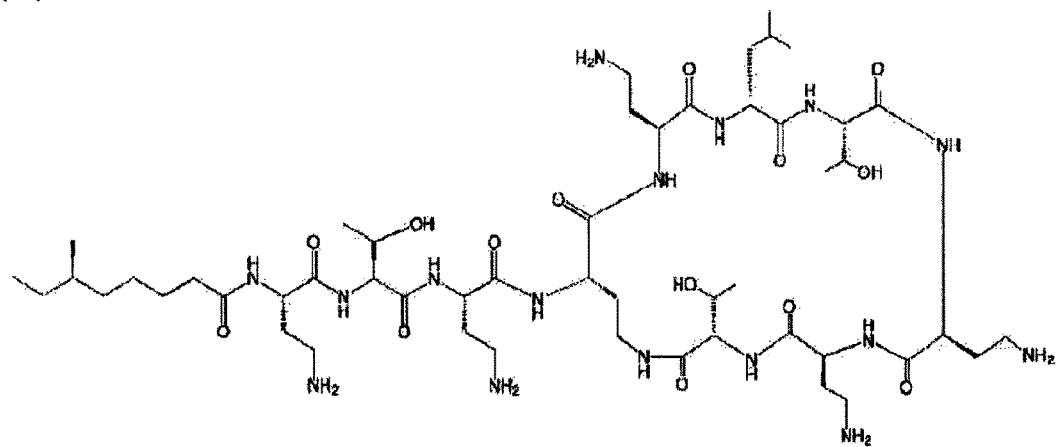

To confirm if the target compound was polymyxin M, acetylation was performed. Particularly, the target compound was treated with pyridine:acetic anhydride (1:1), followed by reaction for 12 hours at room temperature. The molecular weight of the target compound was measured by LC/MS. As a result, it was confirmed that the target compound had the molecular weight of 1493, which was the same weight as that Martinet al (Martin N I, et al., 2003. J. Biol. Chem. 278: 13124-13132) reported earlier (FIG. 1).

Example 2

Sequencing of Polymyxin Biosynthesis Gene

The nucleotide sequence of *Paenibacillus polymyxa* E681 genome was completely sequenced by whole-genome shotgun sequencing strategy and then the polymyxin biosynthetic gene cluster was identified.

<2-1> Library Construction

*Paenibacillus polymyxa* E681 was cultured by the same manner as described in Example 1, and chromosomal DNA was extracted by the method described in Genome Analysis, A laboratory manual Vol. III Cloning systems (CSHL Press, Cold Spring Harbor, N.Y., USA), and the DNA was fragmented to construct a shotgun library for sequencing.

The high molecular chromosomal DNA fragmentation was performed with VCX-500 ultrasonicator (Sonics, Newtown, Conn., USA) with 19% strength, 0.3/3 sec of pulse on/off time, 6 times. The DNA fragments of 2 kb, 5 kb, 8 kb and 10 kb in size were recovered and used to construct the library. pUC18, pUC19, pUC118 or pBCKS (Stratagene, La Jolla, Calif., USA), and pTrueBlue (Genomics One (Laval, Quebec, Canada) vectors were used. The DNAs of ~40 kb and ~100 kb in size were used to construct fosmid library and BAC library, which would be used for forming the contig structure.

The fosmid library was constructed by using a fosmid library production kit (CopyControl™ fosmid library production kit, Epicentre Biotechnologies, Madison, Wis., USA) and the BAC library was constructed by inserting the chromosomal DNA digested with HindIII into pindigo 536 vector (Peterson D. G. et al., 2000, J. Agric. Genomics, volume 5, see internet, ncrg.org/research/jag, Luo M. et al., 2001, Genome 44: p. 154-62).

The reactant for the plasmid library was inserted into *E. coli* DH10B by electroporation, which was smeared on a LB agar plate medium containing X-gal/IPTG/Amp (Ampicillin). White recombinant colony was inoculated to a 96 deepwell plate containing LB(Amp) liquid medium, followed by shaking-culture in a 37° C. incubator with 250 rpm for 48 hours. Cells were recovered and plasmid DNA was separated and purified according to the standard method.

<2-2> Nucleotide Sequence Analysis

DNA sequencing was performed by using BigDye™ terminator cycle sequencing kit (Applied Biosystems, CA, USA) and the reactant was analyzed with ABI 3700 and 3730 DNA analyzer (Applied Biosystems, Foster City, Calif., USA). Files containing the results were analyzed with phred/phrap/consed program (on the worldwide web, phrap.org) .All the result files were analyzed with phred to organize nucleotide sequences and relevant results were collected to mask the sequence of the vector. Sequence combining was carried out by phrap and contig confirmation and edition and primer design were carried out by consed.

Approximately 61,700 sequence fragments (6.7 times) were obtained from the termini of the plasmid and fosmid/BAC, followed by sequencing combining. As a result, approximately 800 contig sequences were obtained, followed by finishing.

Clones connecting contigs by the sequences of the both ends were screened and then a primer was designed to read the gap between sequences, followed by determination of the nucleotide sequence. Only those fosmids connecting a big part having the gap of at least 15 kb were selected, followed by limited shotgun sequencing. The incorrectly combined sequence by repetitive sequences such as rRNA gene or transferase gene was corrected by using consed program. To remove physical gaps, primers were designed based on the end of each contig, followed by recombinant PCR or RT-PCR to obtain the sequences of the unknown region. All the gaps were eliminated to prepare authentic circular chromosome sequence, and Phred was operated. PCR was performed again to amplify the uncertain region. The aim of the accuracy was >99.99% (up to 1 bp error per 10 kb).

The whole nucleotide sequence of the identified *Paenibacillus polymyxa* E681 genome was approximately 5.4 Mbps in total length and had the single circular chromosome structure (% G+C, 45.8).

<2-3> Prediction of a Protein from a Gene

Approximately 4800 protein encoding genes were identified from the genome by running Critica (Badger J. H. and Olsen G. J., 1999, Mol. Biol. Evol. 16, 512), glimmer (Delcher A. L. et al., 1999, Nucleic Acids Res. 27, 4636) and zcurve (Guo F.-B. et al., 2003, Nucleic Acids Res. 31, 1780). To investigate the functions of each gene product, those genes were translated into amino acid sequences, which were screened by blastp with the known protein sequence databases (Altschul S F, et al., 1997. Nucleic Acids Res. 25:3389-3402). At this time, the databases used were COG (Tatusov R. L. et al., 2003, BMC Bioinformatics. 4:41), UniProt Knowledgebase (Bairoch A. et al., 2005, Nucleic Acids Res. 33(Database issue):D154-159), NCBI-NR (on the internet, ncbi.nih.ogv/blast/db/nr.tar.gz) and KEGG-Genes (Kanehisa M. et al., 2004, Nucleic Acids Res. 32(Database issue):D277-280). For the analysis of a domain and a protein family, Pfam (Bateman A. et al., 2004. Nucleic Acids Res. 32(Database issue):D138-141) and TIGRFAMs (Haft D H, et al., 2003. Nucleic Acids Res. 31:371-373) databases were used. For the investigation of a motif and a pattern, Prosite (Hulo N. et al., 2004, Nucleic Acids Res. 32(Database issue):D134-137) database was used.

Psort-B was used to predict the location of a protein (Gardy J. L. et al., 2003, Nucleic Acids Res., 31:3613-3617). The proteins were given hierarchical names considering liability of the screening results. The protein had no homologs having E-value of lower than $10^{-5}$ from UniProt screening was named hypothetical protein.

Figure 2:
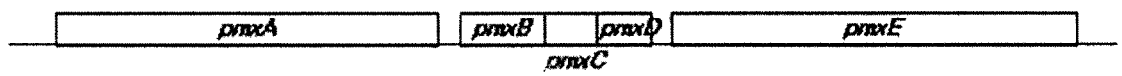
FIG. 2 is a diagram illustrating the structure of a polymyxin biosynthetic gene cluster originated from *Paenibacillus polymyxa* E681.

From the analysis of genome information, at least 4 NRPS gene clusters encoding 4 different antibiotic synthetases have been identified. The substrate specificity of A domain of each gene cluster was compared with the substrate specificity associated active amino acid chart made by Challis et al (Challis G. L. et al., 2000, Chem. Biol. 7: 211-224). As a result, one of them was identified as the gene cluster encoding polymyxin synthetase (FIG. 2).

Example 3

Figure 3:
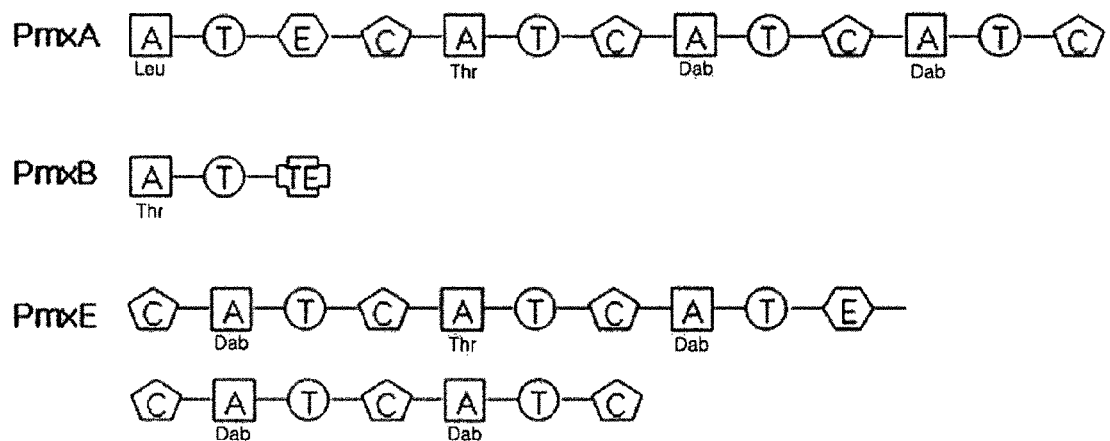
FIG. 3 is a diagram illustrating the structure of the domain of a polymyxin synthetase gene originated from *Paenibacillus polymyxa* E681 genome, A: Domain A (adenylation);
C: Domain C (condensation);
E: Domain E (epimerization);
T: Domain T (thiolation); and
TE: Domain TE (termination)

Prediction of Polymyxin Structure from the Nucleotide Sequence of Polymyxin Biosynthesis Gene The polymyxin biosynthesis gene of the present invention was analyzed based on the chart showing the substrate specificity associated active amino acids summarized by Challis et al (Challis G. L. et al., 2000. Chem. Biol. 7: 211-224). As a result, the gene was confirmed to be organized by such domains as pmx A, pmx B and pmx E, as shown in FIG. 3. Each A domain recognized amino acids such as DAB, Leu and Thr. The amino acid sequence of each domain was determined and the SEQ. ID. NO. corresponding to each domain is shown in Table 1.

TABLE 1

| Domain | pmx A | pmx B | pmx E |
| --- | --- | --- | --- |
| A | 8, 15, 20, 26 | 32 | 39, 44, 50, 57, 62 |
| T | 10, 17, 22, 28 | 34 | 41, 46, 52, 59, 64 |
| C | 14, 19, 24, 30 |  | 38, 43, 48, 56, 61, 66 |
| E | 12 |  | 54 |
| TE |  | 36 |  |

Figure 4:
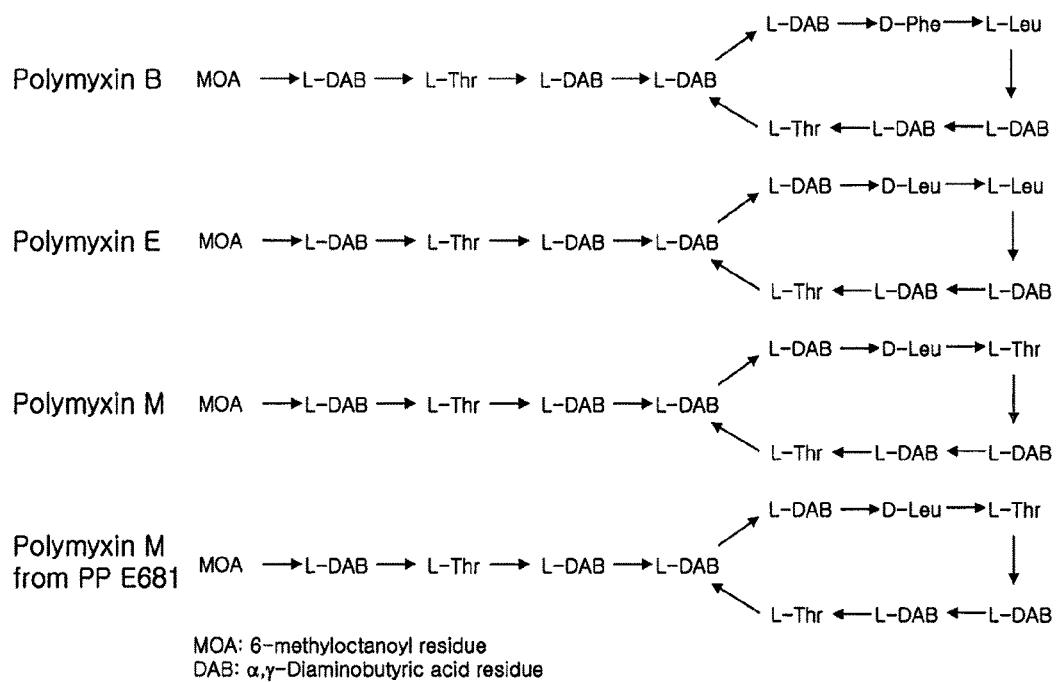
FIG. 4 is a diagram illustrating the structure of polymyxin predicted from the domain structure of polymyxin biosynthesis gene separated from *Paenibacillus polymyxa* E681 genome.

As shown in FIG. 4, the predicted polymyxin structure was confirmed to be that of polymyxin M, which was consistent with the result of Example 1.

INDUSTRIAL APPLICABILITY

As explained hereinbefore, the present inventors confirmed that polymyxin could be produced, separated and purified from *Paenibacillus polymyxa* E681 and then the whole nucleotide sequence of the genome and its domain were analyzed, by which the gene cluster was identified as polymyxin biosynthesis gene. The polymyxin synthetase of the invention can be effectively used for the development of a novel antibiotic and the increase of productivity of polymyxin.

[Sequence List Text]

SEQ. ID. NO: 1 is Pmx A DNA sequence, SEQ. ID. NO: 2 is Pmx B DNA sequence, SEQ. ID. NO: 3 is Pmx E DNA sequence, SEQ. ID. NO: 4 is Pmx A amino acid sequence, SEQ. ID. NO: 5 is Pmx B amino acid sequence, SEQ. ID. NO: 6 is Pmx E amino acid sequence, SEQ. ID. NO: 7 is N terminal (297 aa: 1-297) sequence, SEQ. ID. NO: 8 is A1 (505 aa: 298-802) sequence, SEQ. ID. NO: 9 is A1-T1 linker (18 aa: 803-820) sequence, SEQ. ID. NO: 10 is T1 (64 aa: 821-884) sequence, SEQ. ID. NO: 11 is T1-E1 linker (17 aa: 885-901) sequence, SEQ. ID. NO: 12 is E1 (460 aa: 902-1361) sequence, SEQ. ID. NO: 13 is E1-C2 linker (9 aa: 1362-1370) sequence, SEQ. ID. NO: 14 is C2 (437 aa: 1371-1807) sequence, SEQ. ID. NO: 15 is A2 (530 aa: 1798-2327) sequence, SEQ. ID. NO: 16 is A2-T2 linker (20 aa: 2328-2347) sequence, SEQ. ID. NO: 17 is T2 (63 aa: 2348-2410) sequence, SEQ. ID. NO: 18 is T2-C3 linker (21 aa: 2411-2431) sequence, SEQ. ID. NO: 19 is C3 (425 aa: 2432-2856) sequence, SEQ. ID. NO: 20 is A3 (557 aa: 2855-3411) sequence 2 aa overlapped with C3, SEQ. ID. NO: 21 is A3-T3 linker (18 aa: 3412-3429) sequence, SEQ. ID. NO: 22 is T3 (65 aa: 3430-3494) sequence, SEQ. ID. NO: 23 is T3-C4 linker (22 aa: 3495-3516) sequence, SEQ. ID. NO: 24 is C4 (424 aa: 3517-3940) sequence, SEQ. ID. NO: 25 is C4-A4 linker (19 aa: 3941-3959) sequence, SEQ. ID. NO: 26 is A4 (509 aa: 3960-4468) sequence, SEQ. ID. NO: 27 is A4-T4 linker (18 aa: 4469-4486) sequence, SEQ. ID. NO: 28 is T4 (65 aa: 4487-4551) sequence, SEQ. ID. NO: 29 is T4-C5 linker (21 aa: 4552-4572) sequence, SEQ. ID. NO: 30 is C5 (381 aa: 4573-4953) sequence, SEQ. ID. NO: 31 is N terminal (300 aa: 1-300) sequence, SEQ. ID. NO: 32 is A (530 aa: 301-830) sequence, SEQ. ID. NO: 33 is A-T linker (14 aa: 831-844) sequence, SEQ. ID. NO: 34 is T (62 aa: 845-906) sequence, SEQ. ID. NO: 35 is T-TE linker (25 aa: 907-931) sequence, SEQ. ID. NO: 36 is TE (171 aa: 932-1102) sequence, SEQ. ID. NO: 37 is N terminal (70 aa: 1-70) sequence, SEQ. ID. NO: 38 is C1 (432 aa: 71-502) sequence, SEQ. ID. NO: 39 is A1 (535 aa: 498-1032) sequence 5 aa overlapped with C1, SEQ. ID. NO: 40 is A1-T1 linker (15 aa: 1033-1047) sequence, SEQ. ID. NO: 41 is T1 (64 aa: 1048-1111) sequence, SEQ. ID. NO: 42 is T1-C2 linker (21 aa: 1112-1132) sequence, SEQ. ID. NO: 43 is C2 (427 aa: 1133-1559) sequence, SEQ. ID. NO: 44 is A2 (520 aa: 1558-2077) sequence 2 aa overlapped with C2, SEQ. ID. NO: 45 is A2-T2 linker (20 aa: 2078-2097) sequence, SEQ. ID. NO: 46 is T2 (63 aa: 2098-2160) sequence, SEQ. ID. NO: 47 is T2-C3 linker (21 aa: 2161-2181) sequence, SEQ. ID. NO: 48 is C3 (427 aa: 2182-2608) sequence, SEQ. ID. NO: 49 is C3-A3 linker (31 aa: 2609-2639) sequence, SEQ. ID. NO: 50 is A3 (556 aa: 2640-3195) sequence, SEQ. ID. NO: 51 is A3-T3 linker (14 aa: 3196-3209) sequence, SEQ. ID. NO: 52 is T3 (61 aa: 3210-3270) sequence, SEQ. ID. NO: 53 is T3-E3 linker (20 aa: 3271-3290) sequence, SEQ. ID. NO: 54 is E3 (459 aa: 3291-3749) sequence, SEQ. ID. NO: 55 is E3-C4 linker (11 aa: 3750-3760) sequence, SEQ. ID. NO: 56 is C4 (437 aa: 3761-4197) sequence, SEQ. ID. NO: 57 is A4 (556 aa: 4195-4750) sequence 3 aa overlapped with C4, SEQ. ID. NO: 58 is A4-T4 linker (18 aa: 4751-4768) sequence, SEQ. ID. NO: 59 is T4 (65 aa: 4769-4833) sequence, SEQ. ID. NO: 60 is T4-C5 linker (21 aa: 4834-4854) sequence, SEQ. ID. NO: 61 is C5 (425 aa: 4855-5279) sequence, SEQ. ID. NO: 62 is A5 (556 aa: 5277-5832) sequence 3 aa overlapped with C5, SEQ. ID. NO: 63 is A5-T5 linker (18 aa: 5833-5850) sequence, SEQ. ID. NO: 64 is T5 (64 aa: 5851-5914) sequence, SEQ. ID. NO: 65 is T5-C6 linker (21 aa: 5915-5935) sequence, SEQ. ID. NO: 66 is C6 (377 aa: 5936-6312) sequence.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. An isolated polymyxin synthetase comprising a Pmx A polypeptide subunit having the sequence set forth in SEQ ID NO:4, Pmx B polypeptide subunit having the amino acid sequence set forth in SEQ ID NO:5 and Pmx E polypeptide subunit having the amino acid sequence set forth in SEQ ID NO:6.

2. The polymyxin synthetase of claim 1, wherein the polypeptide subunits contain one or more modules and each module is organized by at least two domains selected from a group consisting of A(adenylation), C(condensation), T(thiolation), E(epimerization) and TE(termination) domains.

3. A gene cluster which encodes the polymyxin synthetase of claim 1, wherein the polymyxin synthesized by the polymyxin synthetase is polymyxin M.

4. The gene cluster of claim 3, comprising a gene which encodes the Pmx A polypeptide subunit, said gene comprising the sequence set forth in SEQ ID NO:1.

5. The gene cluster of claim 3, comprising a gene which encodes the Pmx B polypeptide subunit, said gene comprising the sequence set forth in SEQ ID NO:2.

6. The gene cluster of claim 3, comprising a gene which encodes the Pmx E polypeptide subunit, said gene comprising the sequence set forth in SEQ ID NO:3.

7. The gene cluster of claim 3, wherein the gene cluster is isolated from *Paenibacillus polymyxa* E681.

8. An expression vector comprising a gene encoding a polypeptide subunit selected from the gene cluster of claim 3.

9. A transformed host cell with the expression vector of claim 8.

10. A method for preparing polymyxin M comprising the following steps:
   1) constructing a recombinant expression vector by inserting genes encoding polymyxin synthetase, said polymyxin synthetase comprising a Pmx B polypeptide subunit comprising the amino acid sequence set forth in SEQ ID NO:5, a Pmx A polypeptide subunit comprising the amino acid sequence set forth in SEQ ID NO:4, and a Pmx E polypeptide subunit comprising the amino acid sequence set forth in SEQ ID NO:6, into an expression vector;
   2) transforming a host cell with the expression vector containing the gene cluster of step 1) to produce a transformant;
   3) culturing the transformant of step 2); and
   4) isolating and purifying polymyxin M from the culture product of the transformant of step 3).

11. The method of claim 10, wherein the gene encoding the Pmx A polypeptide subunit, said gene comprising the sequence set forth in SEQ ID NO:1.

12. The method of claim 10, comprising a gene encoding the Pmx B polypeptide subunit, said gene comprising the sequence set forth in SEQ ID NO:2.

13. The method of claim 10, comprising a gene encoding the Pmx E polypeptide subunit, said gene comprising the sequence set forth in SEQ ID NO:3.

14. The method of claim 10, wherein the gene cluster is isolated from *Paenibacillus polymyxa* E681.

* * * * *

SEQUENCE LISTING

```
<160> NUMBER OF SEQ ID NOS: 66

<210> SEQ ID NO 1
<211> LENGTH: 14862
<212> TYPE: DNA
<213> ORGANISM: Polymyxa betae

<400> SEQUENCE: 1
atggcttttg aaaaagaaac gttgttttgg aacgaaaaat ttggtaacga cgattatacc      60
ttgacgcggc tgccttacag caaagctcca agctccctgg cgcccattat gacaaccgtc     120
ggcggttcgc tttcggagga agcggcgcag cgcgtccttc aaatgagcaa gggcgctccg     180
ctggccgctt ttatgatttt gctcgccggt gttcagtcgc tcttgcataa atatacaggc     240
gcttctgaca ttctggtcgg catgccggtt gtacggaaac cgacggagac gcgccgatcc     300
gttaatcata cggtcatttt gaaaaactcg ctttcggcgg gtgcgacttt taaaacgctt     360
ctgaacgagc tgaggacttc cttgccgaga gcgattcagc atcaacatat tccgttcttg     420
aaaatgacgg agaagctgga cctgcaatat gcagacggga tacccgtcgt ccatacgcta     480
gtatccctta aggagctgca tctggacgaa atcgggcaaa acgtggtcac ggattgttcc     540
tttgaattca gcttaaccgg cgggacgata cagctagcgc tgtcatataa cgagcactta     600
tatgactccg agttcatgac tcgggtcgtc ggccatctga atcgcctgct ggtcgtgggg     660
```

-continued

```
cttcacgagt tggagctgga catcgtgcgg gcggacatgc tgtcggaaga cgagaaattt      720
caattgctgc aaagctttaa cgataccgag aaggactatc cccgtgatcg gacaattcat      780
cagctcgtgg aggagcaggc gaagcgggtg cccgaagcga cggcggttgt ctttgagggg      840
cggcggcttt cgtacgcgga gctgaacgaa cgggcgaacc ggctggcgcg gacgttgcga      900
tcgatcggcg tgctgcccaa tcagctggta ggcttgatgg tcagaagatc gttggagacg      960
gtcgttggca ttctggcggt tctgaaagct ggcggtgcct acgtgccgat cgacccggaa     1020
tacccggaag aacgcatccg ctacattttg gagaactcga acgcgcagct gctgctgact     1080
caaagggagc tgctgcagct gcaggtgccg ttcaaggga ccgtggtggc gctggatgac      1140
gagcaggcct acagcgacga tggctcgaac ctggagccgg ccagcggtcc gaacgatctg     1200
gcttatgtca tctatacgtc aggtacgacg gcaatccca aggggtcat gctggagcat      1260 cacggtttgg tcagcttgaa gctgatgttc gcggacaggc tgggcatcac ggagcatgac     1320
cggatcgttc aattcgccag cctgtcgttc gacgcgtcct gctgggaagt gttcaaagcg     1380
ctctattttg gcgcggcttt gtacatcccg acggccgaga cgattctcga caaccgcctg     1440
ttcgagagtt atatgaacga gcatgcgatt acggcggcga ttttgcctcc gacgtacagt     1500
gcttatttga acccggaccg ccttcccagc ttaacgaagc tcgtaacggg aggctcggcg     1560
gtatcggccg aattcgtgca gcagtggaaa cgcaaggtcc actatttcaa tgcttacggc     1620
cctaccgaag cttcgattgt tacgacgctt tgggatgcgg atgaggagca gccggagggc     1680
agagtcattc cgatcgggcg cccgctggcc aatcaccgga ttttattttt ggatgcccac     1740
ctgcagcttg tgcctccggg agtggacggc gagctgtgcg tggcaggcgt ggggcttgcg     1800
agaggttacc tgaaccatcc ggagctgacg gcagagaagt tcgtggaaca tccgtttgcg     1860
ccgggagaac gcctttaccg gacgggagat ctcgcccgct ggctgccgga cggaaatgtt     1920
gagtacttgg gccggatcga ccatcaggtg aaaatccgtg gattccggat cgagatcggc     1980
gagattgaag agcagcttct gaagatcgac tccgtgcagg agacgatcgt aatcgcgcgg     2040
gaaggcaaaa gcgggcaaga actgtgcgct tacctggtcg cgggccgccc gcttacgctc     2100
ggcgagctaa gaagcgcgct ggcgcaaaaa ttgccgaatt acatgattcc ggcgcatttt     2160
gttcagcttc cgcagatgcc gctcacgccg aacgacaaaa tcgaccgcaa ggctttgccc     2220
gctccggaag gaaacgcgct gaccggcggc gcgtacgtag ctcccccgcaa tgaagccgag     2280 cggacgcttg ccgatgtgtg gcaggcggta ttgaacgccg atcgcgttgg ggtaacggat     2340
catttcttcg agctgggcgg agactcgatc aagtccattc aagtatcttc gcggcttcat     2400
caagccgggt acaagctgga aatccgggat ttgttcaaat atccgactat ttcacagctc     2460
agcctgcatg tgaaaccgat cggacgtacc attgatcaag gcgaaataac gggtgaaacg     2520
gcgctgacgc cgattcagca ttggtttttc gagagctcct ttgcggaccc gcatcatttc     2580
aaccagtcgg tgatgctgta ccggaaggag cgcttcgacg aagagacggt gcgtcaggtg     2640
ctgcaaaagc tggccgagca tcatgacgcc ttgcggatgg tgttccgcaa gacggaacaa     2700
gggtttagcg cgcggaaccg cgcgattcag acggcgggt tgttcacgct ggacgtgttc      2760
gacttcaagg atgcggagaa taccgagcag gctgtggaag cgaaggcaac ggacattcaa     2820
gcgggcatcg atctggagaa cgggctcctc ttgaaggcgg gactgttccg gtgcgcggac     2880
ggagatcatt tgctgctcgc ggttcatcat gccgtggtgg atggcgtgtc ttggcgcatt     2940
ttgatggagg atttcgctct gggttacgag caggccggca aaagcgagga aattcgttt c    3000 ccggcgaaaa cggatgcgta ccgcacttgg tccgaacagc tggccgctta cgcgcaaagc     3060
```

```
ccggaaatga cgaaggaacg ggcctattgg caggccatgg aacaaattgc ggttccggcg    3120
gtgccgaagg atctggatgt ggacgttacg acgcagcagg acagcgaatc gctgttcgtc    3180
cgtttgactc ccgaagaaac ggagctgctg ctgaagcggg ttcaccgggc ctacaacacc    3240
gaaatgaacg atattttggt aacggcgctc ggcatagcca ttcgcaagtg dacgggacac    3300
gaacgggtgc ggatcaatct cgaaggacac ggacgcgaat cgatcggaac ggatatcgac    3360
atcacgcgca cagtcggctg gtttacgacc aagtttccgg tcgtcctgga gccggaaacc    3420
gaccgggatt tggcctatca gattaaacag gtcaaggaaa gcttgcgccg cattccgaac    3480
aaggggcttg ggtacggcgt atgccgctat ctctccaaat cggaggatgg ctttgtttgg    3540
ggcgcagagc cggaaattaa ttttaactac ctccggccagt tcgacgatga tgtcagtcag    3600
gtcgagatcg gcatatcttc ttattccagc ggcagcccgg ccagcgaccg gcaggcccgc    3660
agctttgtgc tggatatcaa cggcatggtg ctggacggcg cttttatcgct cgatctcagc    3720 tacagccgga agcagtatcg caaggaaacg atggaagcct tcgctcagcg gcttgagcaa    3780
agtctgcgag agctcattac ccactgcgca ggcaaagaaa acaccgaatt gacgccgagc    3840
gacgtgcaat ttaaaggctt gaccatcgcg gaattggagc aaatcgccca gcgctcgggc    3900
catctcgggg aaatcgaaaa tatttactcg cttacgccga tgcagaaggg catgtggttc    3960
cacagcgcgc ttgaccggca aactgccgct tacttcgagc agacgcggtt tacgatgcgg    4020
ggagcgctcg acgtccagct tttcgagagg agctggatgg agcttgcgaa acgtcatctg    4080
gtgctgcggg cgaattttgt gaaaggaccg gagggcgagc cgctgcaagt catataccgc    4140
gacaagccgg tcggctttga atatgaagag ctgcttcatt tgcaggcgga cgagaaacaa    4200
gcgtatttgg ataaaaaggc cgaggatgac aagcttcgcg gcttcgacat ggaacatgac    4260
gcgctcgttc gggttacgat cttgcgcacc gaagagcaaa gctatcatgt gctgtggagt    4320
ttccagcata ttttgatgga cggctggtgc ctgccgcagc tgacgcagga gctgtttgag    4380
atgtactcgg ccttggcatc cggcaagcag ccagcgggag ataagggatc ggattatggc    4440
gcttatatcg aatggttgga gaaacaggac gatcaggcgg catccggcta ttggacggca    4500
ttcctggcag attatgaagg gcaaaccgta ctcccgggac aaaaggaacc ggcgccaagc    4560
ggcatattta cggctgatca cgtcaccgcc gagctgggca aggacttgag cgagcggatg    4620
gaccgggtgg cgaaacagcg cctggttacg gtcaatacgc tgctgcaagc cgcttgggc    4680 gtgatgctgc aaaaatataa cggaacaaac gatgccgtat cggcagcgt cgtggccgga    4740 agaccggcgg aaatcccggg cattgagtcc atgatcgggc tgttcatcaa tacggtgccg    4800
gtccgcgtca cgagcgaagc ggacaccgtg ttcgccgacc tgatggcgaa gctccaagag    4860
cgggcgctgg agtccgggcg atatgattac tatccgctgt atgaaattca gcccgcagc    4920 gtgcaaaagc agaacctgat caaccatatc atcgcttttcg agaactatcc ggtggacgag    4980
cagatggagc aggcgggcga ccagcagcac ggcgacctga cgatcgctga cgttcagatg    5040
gaggagcaga cgaactataa cttcaacgtg accgtggtgc cggagtcga gatcgaaatt    5100 cggttcgact ttaacgctga agtgttcgat aaagacagca tcgagcggct caagggacac    5160
ctcgtccatc tgctggagca ggtgacggat aacccgaaa ttacagtggg cgagctggaa    5220
cttgtgacgg aggggggaaaa ggccgacctt tcggacgtt taacgacac caccacggaa    5280 tttccgcgcg ggaagacgct cgttcaattg ttcgaagaac aggcggagct ttacccggac    5340
aacgtggccg ccgtcatgaa cgagcggcaa ctgacctacc gcgagctgaa cgagcgatcc    5400
```

-continued

```
aaccgccttg cgcggaagct gcgagagacg ggagtagaag cggaccagct ggtagcgatt    5460
ctggccgaac gctcgctcga tatggtcgtc ggcattctgg ccattctcaa agcgggcgga    5520
gcctacgtac ctgtcgatcc cgactacccg gaggagcgca tccgcttcat gatcgaggat    5580
tcgggcgcgc cgttattgct gattcaaaag catctgcacg agaagaccga cttcgcagga    5640
acgcgcctcg aattggacga tttcgtttgg ggcgacagag gggcggactc cgccgatgcg    5700
ttggacgctt cgaacctgga gccgatttcc gggccgggca acctggcata tgtcatctac    5760
acgtcgggaa cgaccggcag accgaaagga acgctgatcg agcataagaa cgtcgtgcgg    5820
ctcctgttca cgacaagaa cctgttcgac ttcgggccgt ccgacacgtg gacgctgttc    5880
cactcgttct gcttcgattt ctccgtctgg gaaatgtacg agcgctgct gtacggaggc    5940 aagctggtca tcgtaccgtc gctcacggcg aaaaatccgg ccgatttcct ggcgttgctg    6000
ggccgcgaac aggtcacgat tttgaaccag acgccaacat acttctacca gctgctgcgt    6060
gaggtcttgg cggaccatcc gtacgatctg cggattcgca acgtcatctt tgggggcgaa    6120
gcgctgagtc cgctgctgct caagggcttc aagacgaagt acccggagac gaagctgatc    6180
aatatgtacg gcattaccga gacgacggtt cacgtgacgt ataaggaaat cacgtgggtc    6240
gaaatggagg cggcgaagag caatatcggc aagccgatcc cgacgttgag ggtgtacgtc    6300
ctagatgaaa accgccgccc tgtgccgatc ggcgtagcgg gcgaaatgta cgtggccggg    6360
gaaggccttg cgagaggata cctgaaccgt ccggatctga cggcggagaa gttcgttgat    6420
tccccgtttg cggagggga gaaactgtac cgttcgggcg acttggcggc ttggctgccg    6480
gacggcaaca tcgaatacct gggccggatc gaccaccagg tcaaaatccg tgggtaccgg    6540
atcgagctgg acgaaatcga gacgcagctt ctgaacgtcc ggggtgtgga agaagcggtg    6600
gtgctcgccc gtcaggacgg cgggggcgag aaggcgcttg tcgcctactt tgtggcggac    6660
cggacgctga cggtcagcga aatgagaacc tcgctggccc agggaatgcc ggggtacatg    6720
atcccgtcgt acttcgtgca gttggagcgc atgccgctga cgaccaacgg caaagtggac    6780
cgcaaagcgc tgccggagcc gcaaggcggc atacaaacgg tgtcgaata cgtagcgccg    6840 cgtaactgga cggagtccca gcttgtgaag atctgggagg aagtgctggg ctactccggc    6900
attggagtcc tggacaattt cttcgagctc ggaggccact ccttgcgggc gacgaacctt    6960
gtcagcaaga ttcagaagga aatgaacgtc gagctgcctc tgcgcgacgt attccgctat    7020
tcgacgatcg aagagatggc tcttgccatc tcccggatcg gagagcagtc gttctcgtcg    7080
attccgctgg caggcgcaag agcatattat ccgctttcct cagctcagaa gcggctgttt    7140
atcctgaatc agctggaagg ggccgatcag agctacaaca tgccgggggt gctgctgctg    7200
gaaggatcga ttgaccggag cctgctggag aaggctttcc gcggactgat cgcacggcac    7260
gaaacgctgc gaaccggctt tgagattgta caaggcgaag caatacagcg catttacgag    7320
agcgtcgact ttgccgtcga gtaccgtcat gcgagcgagg aagaagcgcc tgaagtcgtg    7380
caggccttca tccggccttt cgacttggcg aagcccccgt tgctgcgggc ggagctcgta    7440
gagctggcag ccgaacgtta cttgctgatg ttcgacatgc accatatcgt ctccgacggg    7500
gtttcgatgg acgtgttagt cgaggaactc gttcgtctgt acggcggcga gtcattagag    7560
cctttgcgca ttcaatacaa ggactatgcg gtatggcagc agtcggacga gcaaaaagtg    7620
cagttgaaac gcgaggaagc ttactggctg gaccgttacc ggggcgagct gccggttctg    7680
gaaatgccga cggactatcc gcgtcctgcc gtgcagagct ttgagggaca aacgctgacg    7740
tccttcgtgg acgaggcaac gaacgaaggc ttgaagcagc tggccgctca aagaggaacg    7800
```

```
acgctgtata tggtgctgct tgcggcatat accgtgcttt tgcataaata cacaggtcag   7860
gacgatttga tcgtcggaac gtcgattgcg ggcagaacgc acggagacac gcagcctttg   7920
atcggaatgt tcgtcaatac gctggcgctc cgcaattatc cggcttcgaa gaagaccttc   7980
ctgtcgtatc tggaagaagt gaaagaaacg actttaggcg cttacgagca tcagaattat   8040
ccgttcgaag agctcgttga taaagtgcag gtcagccggg atttgagccg caacccgctg   8100
tttgacacga tgttctccct gcaaaacttg gaggataaag agtttgagct ggaagggctg   8160
aaattgtcct cgtaccctag cgaataccgg acggccaagt tcgacctgag tgtggatgtt   8220
acggaagaaa acggcggcct ggagtgcagc tttgaattcg caacggctct ttataaagaa   8280
agcacgatcc ggcggctgtc gactcatttc ggacatttgc ttgcggcgat cgcaagccgt   8340
ccggatgcga agattgccga gctgaacttg ctgacggcag aggaaaaaga gcaaattctc   8400
ggcgcgttca acccgcgcag ctggaagcg gctcctgcgg ccgcgttcca ccggctgttt   8460
gaggaacagg tggagcgcac gccggaagag gcggccgtcg tgtacgagaa tgagcggctg   8520
acgtatgcgg agctgaacga gcgggcgaac cgcttggcgg ctacgctgcg cgcaagcggc   8580
atcggccggg agacgatcgt cggcattctc gccgagcgtt cggtggactt gctggtggcc   8640 gtgctgccg tctggaaagc gggcggggcg tatgtgccgc tcgacccgga ttatccggca   8700
gaccgcgtgc ggttcatgct tgaagacagc ggagcgaagg tgctgctgac gcaaacggcg   8760
ctgcgagagc gtgccgaagc ctggctcggc gaagaggagc tggcgctggc ggcggtgctg   8820
tacctggacg acgaagcgtc gtacaacgag gagcgggcga atgcgccggt tggctccggc   8880
atggtctccg gcaagctgac ggatgctgtg gacgacggcg atgagagcca tcagaatgtc   8940
gacaccgacg gcttccatga agcccgtcca gaggacctgg cgtacgtgat ctacacgtcg   9000
ggaacgacgg gcaagccgaa gggcgtgatg atcgagcacc gcagcctggt gaacacggcg   9060
gcgggctacc ggcgggaata ccggttggat cagttcccgg tgcggctgct gcagctcgca   9120
agcttctcgt tcgacgtgtt cgtgggagat atcgcgcgga cgctgtacaa cggaggtacg   9180
atggtgattg tgccgaagga cgatcggatt gatccgtctc gtctgcacca ctggatggag   9240
cgggagcggg tcaccatctt cgaatcgacg ccggcgctga tcgtgccatt cctggagtac   9300
gtgcacgagc agcggctgga tatgagctgg atggagctgt tgatcacgag ctcggacagc   9360
tgcagcgtgg cggattaccg gaccttgcag gaacgcttcg gctcgttgtt ccggatcatc   9420
aacgcctacg gcgtgacgga agcggcgatc gactccagct tctacgacga ggagctgacg   9480
aagctgccgc agacaggtca tgtgccgatc ggcaaagcgt ggctgaatgc gaaattctac   9540
atcgtggacg cgcatctgaa cccggtgccg gtcggggtgc tggcgagct ggtcatcggc   9600 ggagtcggag tggcgcgcgg gtacttgaac cgtccggagc tgacggaaga gaagttcgta   9660
gacagtccgt tcgccgcggg cgagcggctg taccgcacgg gagacttggc gcggtggatg   9720
gaggacggga acgtggactt catcggccgg atcgacaacc aggcgaaaat ccggggggtac   9780 cggatcgaga cgggcgagat cgagtcgcag ctgctgcggg tggaaggcgt gcgcgaagca   9840
gtggtgctgg ttcgaagtga cgcgaacggg cagaaggcgc tatgcgcgta ttacacgccg   9900
gataccggag cggagctggc ggtgaacgat ttgcgcggcg cgctggcgca ggagctgccg   9960
ggctacatga tcccgtcgta cttcgtggag ctggagcgtc tacctctgac gccgaacgga  10020
aagattgacc ggaaggcgct gccggcgccg gaaagggaag cgggaagcgg aacggagtac  10080
gtcgcaccgc gcaatgagct ggaaacgaag ctgacggcga tttggcagga ggtgctgggg  10140
```

```
cttgcgaagg agattggcgt tcacgacaac ttcttcgaca tcggcggcca ctccctgcga   10200
gcgacgacgc tggtcagcaa gattcataaa gagttgaacg tggatctgcc gctgcgcgac   10260
gtgttccgcc attccactat cgagagcatg cggccgcca tttcccggct ggatgagcag   10320
acattcgttg ccattccggt ggcggatgac cgagaggtgt acccgcaatc ttttgctcaa   10380
aaacgtctct ttatcctgaa tcaactggaa ggcgcagagc ttagctacaa catgccggaa   10440
gcgatgctgc tggagggtgc tttggaccgg acaaggttcg aagaagcgtt ccgtaagctc   10500
gtggcgcggc atgaaacgct gcgcaccggg ttcgaaatgg tggatggcga agcatcgcag   10560
cggatttacc aggacgtgaa ttttgccgtg gagttctatc gagtggatga gcaagaggcc   10620
gaagagacgg ttcaccgttt cgtccgtccg tttgacttgg cgaagcctcc gctgctgagg   10680
gtaggccttg tcgagctggc tccggaacgc catattctaa tgtacgacat gcatcatatt   10740
atttccgacg gcgtctcgat ggaaatcttt gttgaagaat tcgtccgctt gtacggcggc   10800
gagcaattgg agcctctgcg cattcagtac aaagactaca ccgtttggca gcattcacag   10860
gagcagaaag aacggcttca gcgtcaggag gcgtactggc tggacatgtt ccaaggcgag   10920
cttccggtgc tggaaatgcc gaccgactat ccgcgtccgg ccgtgcagag ctacgaaggc   10980
caaacgctgg agttttcctt cgacgcttcg aaaaccgacg gcctgaagca gctggcctcg   11040
gaaacgggca cgacgctgtt tatggtgctg cttgcgcgct ataacgtcct tctgcataaa   11100
tattcaggtc aggaagacgt gatcgtcggt acgccgattg ccggaaggaa tcatggagat   11160
gtgcagccgt tgatcgggat tttcttaaac acgctggcta tccgcagtta tccggcttcg   11220
gagaagacat tcctgtcata cctgaacgaa gtcaaagaaa cgaccctcca cgccttcgag   11280
catcaaaact atccgttcga agaattggtg gacaaggtgc aagtcacccg tgatttaagc   11340
cgcaatccac tcttcgacac gctgtttacg atgcagaata cggagaacga ggaatttgag   11400
ctggaagggc ttcgcctgat tccttatccg agcgcactgg ataccgcgaa gtttgatatc   11460
agcttggatg tgggcgagga gaacggcggc ttggattaca gcttcgaata tgcgacggct   11520
ctctacaaaa gggagacgat cgaacggctg gcgaaacatt acgagcagct gctcgtaacg   11580
atcgtaagcc gtccggatgc gaagatcgcc gagctgaact tgctgacggc agaggaaaaa   11640
ggacaaattc tcggcgcgtt ccacccggcg cagctcctgc cggctcctgc ggccgcgttc   11700
caccggctgt tcgaggaaca ggcggagcgc acgccggaag cggtagccgt cgtgtacgag   11760
aatgaccggc tgacgtatgc ggagctgaac gagcgggcga accgcttggc ggctacgctg   11820
cgcgcaagcg gcatcggccg ggagacgatc gtcggcattc tggccgagcg ttcggtggac   11880
ttgctagtgg ccgtgctggc cgtctggaaa gcgggcgggg cgtatgtgcc gctcgacccg   11940
gattatccgg cagagcgcgt gcggttcatg ctcgaagaca cgcgagcgaa ggtgctgctg   12000
acgcaaacgc cgctgcgaga gcgtgccaaa gcctggctcg gcgaagagga gctggcgctg   12060
gcggcggtgc tgtacctgga cgacgaagcg tcgtacagcg aggagcgggc gaatgccgac   12120
agcttccatg aagcccgtcc agaggacctg gcgtacgtga tctatacgtc gggaacgacg   12180
ggcaagccga agggcgtgat gatcgagcac cgcagcctgg tgaacacggc ggcgagctac   12240
cggcgggaat accggttgga tcagttcccg gtgcggctgc tgcaactcgc cagcttctcg   12300
ttcgacgtgt tcgtgggaga tatcgcgcgg acgctgtata acggaggtac gatggtgatc   12360
gtgccgaagg acgaccggat cgatccgtct cgtctgcact actggatgga gcgggagcaa   12420
gtgacgatct ttgaatcaac gccggcgctg atcgtgccgt ttatggaata cgtgcacgag   12480
caagggctgg atatgagctg gatggaactg ttgatcacga gctcggacag ctgcagcgtg   12540
```

-continued

```
gcggattacc ggaccttgca ggaacgcttc ggctcgttgt tccggatcat caacgcctac    12600
ggcgtgacgg aagcggcgat cgactccagc ttctacgacg aggagctggc gaagctgccg    12660
cagacaggcc atgtgccgat cggcaaagcg tggctgaatg cgaaattcta catcgtggac    12720
gcgcatctga acccggtgcc ggtcggggtg ctgggcgagc tggtcatcgg cggagtcgga    12780
gtggcgcgcg ggtacttgaa ccgtccggaa ctgacgggag agaagttcgt agacagcccg    12840
ttcgccgcgg gcgagcggct gtaccgcacg ggagacttgg cgcggtggat ggaggacggg    12900
aacgtggact tcatcggccg gatcgacaac caggcgaaaa tccggggcta ccggattgag    12960
acgggcgaga tcgagtcgca gctactgcag gtggaaggcg tgcgcgaagc ggtggtgctg    13020
gttcgaagtg acgcgaacgg gcagaaggcg ctatgcgcgt attacacgcc ggataccgga    13080
gcggagctgg cggtgaacga tttgcgcggc gcgctggcgc aggagctgcc gggctacatg    13140
atcccgtcgt acttcgtgga gatggagcgc ctgcctctga cgccaacgg aaagattgac    13200 cggaaggcgc tgccggcgcc ggaaggggaa gcgggaagcg gaacggagta cgtcgcaccg    13260
cgcaatgagc tggaaacgaa gctgacggcg atttggcagg aggtgctggg gcttgcgaag    13320
gagattggcg ttcacgacaa cttcttcgac atcgcggcc actccctgcg agcgacgacg    13380
ctggcgggca aggtatttaa ggaattaaac gtcaacctgc cgctgcgcga cgtattccgt    13440
cactcgacga ttgcggcgat ggccgaggcg atcgcccgga tggaacggcg ggagcatgag    13500
gccattcctc aagcggagga gagagagtac taccctctgt cctccgcgca gaaacggctg    13560
ttcattcagc acacgctgga tggagcggat cagctttaca acatgccgga gctggtgcag    13620
gtggaaggcg agtttgattt agaacggttg gaagccgcct tgcggaaatt gataacacgg    13680
catgaatcgc tgcgcaccgg ttttgaaatc gtgaagggcg aagcggttca gcggatttac    13740
ccgcaggtcg attttgctat cgagcattat caagcggata agaggatgc ggctcaaatc    13800 gagcagatcg tccgcagctt cgttcgtccg tttgatctcg gcaagccgcc gctgctgcgc    13860
gccggggtca tcgagctgga gccgaacctg catattctcc ttttcgacat gcaccatatg    13920
gtgtccgacg gcgtatcgat ggcgattgtg atcgatgagt tctcgagttt ctacgccggg    13980
gaagaactgc cgccactgcg cattcaatac aaggattatg ccgtttggca gcagtcgaag    14040
gcccaccgag agcggatcgg gcggcaggaa gcgtactggc tgcaaaacctt cgaaggcgag    14100 ctgccgacgg cagacctgcc gatggactac gaacggtctg cggctcgcag ctacgaaggc    14160
gcgcatctga gttcgacgt cgaagcttct ctctctgcgc agctgcgcga attggcggcc    14220
gagcgtgaaa gcacgctgtt catggtgctg cttgcggctt ataccgtgct gctgtccaag    14280
tacagcgggc aggaggactt ggtcgtgggc accccggtgg cgggaagaac gaacgccgat    14340
ttggaaccga tcatcgggat gtttgtcaat acgctggcga tccgcaatcg tccgtcgggc    14400
gacaaaacgt tcttgtccta cctggaagaa gtgaaggaaa cggctttggg tgcttttcgag   14460 aaccaggatt atccattcga ggagcttgtg gagcgtttga atgtgaagcg ggaaccgggc    14520
cgcttcccgc tgttcgatgc cgttttcgac ttgcaaaata tcgaagaacg agacgccgag    14580
ctggaagggg tcagcctgaa gacttacgag cttgaccatt tggaagaagc gaagttcgat    14640
ctgacgctgt ttatgtatga aaacaatggg gcgctgagcg ggggcttctt ctacgccacc    14700
aagctgttca aagaagcgat gatccgcacc ttgaccgagg attacctgcg ggtactgtct    14760
caaattgcga aaatccaca actcgagcta agccggatag aatgtcataa accggcggca    14820
ggcgcaaaga gtgccgtcga tacgatcgaa ttcgcgttct aa                      14862
```

<210> SEQ ID NO 2
<211> LENGTH: 3309
<212> TYPE: DNA
<213> ORGANISM: Polymyxa betae

<400> SEQUENCE: 2

```
atgaaatctt tgtttgaaaa ggaagaacag tactggagcg gtaagtttga cgccgatgac      60
agcctgagct tccttcccta cagtcaatcc tccaaattat ccgcccacgg ggaagctgcg     120
gccgagccgg gcttgcttca ccgtactctg ccgagtcaac tctcggagag aatcattagc     180
ctcgccaacg gttcggattt ggctttgtac atgattgttt tggcaggagt aaaaagcctg     240
ctgttcaaat ataccgggcg ggaccaagtg ctggtcggca tgccttctta tagcgcagac     300
cccgacggga ctccgccgcc gcatgacatc ttggtgatca agacgtccgt aagccgccag     360
actacgctga aaacgctgct cgggggcatc aaagcctcca tcggcgaggc gctggagcat     420
cagcacctgc cttttcggaa aatggtggag ccactccatc tggactatac ggggacggc      480
ctcccggtcg ttaacaccgt cgtatccttc gccccgattc atccggaacc gcaaggtaat     540
cgggtggcgg ccgatacggt ttttcgcttc gaccgccaaa accactccat cgagctggaa     600
ataagctttg acgggcagcg gtacgagcgg gcatttgtgg aacaggcggc cgaccatctt     660
gttcggctgc tgtccgtgct tttatttcag ccggatctga agctgggaca agccgatgtg     720
ctgtcaccag acgagaggga gacgctgctg aaacgattta atgacaccga aaccgagttc     780
gagcggggga aaacgattta cggcttgttc gaagagcagg cggagcttta cccggacaac     840
gtggccgccg tcatgaacga gcggcagctg acctaccgcg agctgaacga gcgatccaac     900
cgccttgcgc ggaagctgcg tgaggcggga gtagaagcgg accagctggt agcgattctg     960
gccgaacgct cgctcgatat ggtcgtcggc attctggcga ttctcaaagc gggcggagca    1020
tacgtgcctg tcgatcccga ctacccggag gagcgtatcc gcttcatgat cgaggattcg    1080
ggcgcgccgt tattgctgat tcaaaagcat ctgcacgaga agaccgactt cgcaggaacg    1140
cgcctcgaat tggacgattt cgtttggggc gacagagggg cgaactccgc cgaagcgctg    1200
gacgcttcga acctggagcc gatttccggg ccgggcaacc tggcatatgt catctacacg    1260
tcgggaacga ccggcagacc gaaaggaacg ctgatcgagc ataagaacgt cgtgcggctc    1320
ctgttcaacg acaagaatct gtttgacttc gggccgtccg acacgtggac gctgttccac    1380
tcgttctgct tcgatttctc cgtctgggaa atgtacggag cgctgctgta cggaggcaag    1440
ctggtcatcg taccgccgct cacggcgaaa atccggccg  atttcctggc gctgctgggc    1500
cgcgaacagg ttaccatttt gaaccagacg ccaacgtact tctaccagct gctgcgtaag    1560
gtcttggcga ccatccgta  cgatctgcgg attcgcaacg tcatcttcgg gggcgaagcg    1620
ctgagtccgc tgttgctcaa gggcttcaag acgaagtacc cggagacgaa gctgattaat    1680
atgtacggca ttaccgagac gacggttcac gtgacgtata aggaaatcac gtgggtcgaa    1740
atggaggcgg cgaagagcaa tatcggcaag ccgatcccga cgttgagggt gtacgtcctg    1800
gatgaaaacc gccgccttgt gccgatcggc gtagcgggcg aaatgtacgt ggccggggaa    1860
ggccttgcga gaggatacct gaaccgtccg gatctgacgg cggagaagtt cgtcgattcc    1920
ccgtttgcgc aggggagag  actataccgc tcgggcgact ggcggcttg gctgccggac    1980
ggcaacatcg aatacctggg ccggatcgac caccaggtca aaatccgcgg gtaccggatc    2040
gagctggacag aaatcgagac gcagcttctg aacgcccggg gcgtgaaaga agcggtggtg    2100
ctcgcccgcg acgacgcgca cggccataag cagcttgtcg cttattacgt cgcggaaacg    2160
```

```
aggctggcgg cgaatgaact caaggaggag ctcgccaagc agcttccagg gtatatgatt    2220
ccttcgcacc tcgtgcagct ttcgcggatg ccgctgaccc cgaacgggaa aatcgaccgc    2280
aaagcgctgc ccgcgccgga ggaagccgcg gccggaggag cggaatatgt cgcgccgaga    2340
acgctgctcg aaatgaagat cgtccgcgtc tggcaggata cgcttggcgt tccgcaggtc    2400
ggcgtaaagg ataactttt  tgagttgggt ggcaattcgt taagtctgat gaggctcgtt    2460
caagccgttt acgatgaaac gggcattgag ataccactga accgccaatt ccataatgta    2520
acagttgaag ccatggcttt cggagagggg gatctgggcc tggataaagg gggagactcc    2580
ttcattaagc tgaataaagc aggagatctg aacgtgttct gcttccctcc gggcagcggc    2640
ttcggcatcg gttaccggga gctcgcaagc aggctcgacg gccggttcgt gctctacggc    2700
attgatttta tcgacgatgc cgccgattac gaagccatgc tgaaccgtta tgtggacgag    2760
atcgtccgca tccagccgga aggaccttac gtgctgctcg gctactgctt tggaggcaac    2820
ctgatgttcg aggtagccaa acgatggag  aaaagagagt attccgtaac ggacgtgctc    2880
atggtggact cgtggattaa ggacacgctg acgccttccg aaacgtcgga gaaagagctt    2940
gaagaaacgc ttgccgattt cgacgaagaa gagaaggaat taatgagcaa cccgctcgtg    3000
cgggagcgtg ttcatcggaa ggtcaaagcg accttggcgt acgaagcgca gcttatgaat    3060
tccggcacga tcccggccag gatttacgaa ctgattgcga aggacagcga agcgttccgc    3120
ctggagcacc aattgccgtc ctggcggggg gcaacgacgc aagcttacgc cgattaccgg    3180
ctggagggcg cgcacgagga attgctggaa ctcgcgcgcg tggacgaaac ggccgttgtc    3240
atccgggaca tcttagaaca agtcaagcgg cagatcgaag cggaggccgg ggtactgcat    3300
ggaagctga                                                            3309

<210> SEQ ID NO 3
<211> LENGTH: 18939
<212> TYPE: DNA
<213> ORGANISM: Polymyxa betae

<400> SEQUENCE: 3
gtgagagaga ataccaaaga gcaatatgga ttaacgcaag cccagcgccg aatatggttc      60
atggaaatta tgaatccggg aacgtccatc acgatgcttt ccgcgaccta ccagattacg     120
ggcgagatca acacacagct tctggagcaa gcggcagcag agatcgtcaa aacctatgac     180
gttttccgaa tccgcattag cggggatttg caaaatccaa cgcagtggtt cgaagagccg     240
gagaatgtcc aggctaggat aagccgcctc gaaataggca caaccgaaca attctatgct     300
tgggtgaaag aagtaagcga aaaccggcc  agcgtgttcg acgaacacct ccaccaattt     360
acgattatcc attttgtgaa cggccaagta tggctcaatt tgacggtaaa tcatattatc     420
gccgacggct tgtccgtcaa tgctttgctg catgcggtga tggaaaaata cctgaactg      480 cgcaaaggca tctccagcag ttaccaggcc ccttcctatc tggattatat tccgcggag      540 cgtgaatatg agcaatcgca gcgttatcaa aaaggcaagg aatactggct gacgaagtac     600
aacactttgc ctgaaacgac cggcattaaa tcgtatccgc cattctcgat cggcagcgaa     660
tccaataaac tgtccatcac tttggacggt tccggtatg  aacgcattct gaccttcagc     720
gaacaatatc aggtcagctt atatacgtta tttctgtccg ccatgtacgc cttattgtac     780
aagctgaccg acagcatcga tgttccggtc ggcacggttt tcgccaatcg caccagcaag     840
aaggaaaaag aaacgattgg catgttcgtc agcaccgtgg ctacgcggat tcgtctgaat     900
```

```
ccagacagga acgtgctttc cttgatccaa acggtttcca aggaaaatac ggcggatctg      960
cggtatcaga ataccctta taaccaattg atccaggatt tacgtgaaca acacggccgc     1020
aacgatcttt cggggctgtt ccgcacgtct ctggaatatc tgcctttgaa aatcgtggag     1080
tacgaagaaa tcaaggtacg cctggaggct cactttgcta ggcacgagat ggacgatttg     1140
ctgctgcgct tcgaccatat gctgaatgaa ggccatgtca ttctccatgc ttcctatcgt     1200
accggcttgt tcgagacggc cgagattgat cggattatgg aacagtatgt aaccgttctg     1260
gaccagtttc ttcagactcc cgaactgccg atacgcgaga tttctctgct gagcgatgag     1320
gagagacacc gcattctcaa cgtttttaac ccgccggtgg cagggctgag cgagggagaa     1380
gcgtttcatc ggtatgttga aagtttgct cgagaaattc cagatcatcc ggcagtcgtc     1440
tacatggaca aacagctgac ctacggcgaa ttgaacgaac gcgccgagcg gctggcttct     1500
ctccttcgcg aacagggcgt gggaaaggag acgattacgg ggatctgggc ggagcgttca     1560
gtggaactgc tggtcgggt gctcgccgtt tggaaagccg gcggagccta tgtaccgctg     1620
gaccccgatt atccggcgga gcggattgag tacatgctca gcgatagcga tgcatcggtg     1680
ctgcttacgc agcgtcatct gttggagcgg gccgaggtt ggttggccga tgaccggctg     1740
aagcttcaag ctgtctatgc catggacgat gaacagattt ataacgggga tgccttagcc     1800
gtggaatttg aatctgccgg cagcgccccg caagacttgg cttatgtgat ttacacctcg     1860
ggtacgacgg gacgcccgaa aggtgtcatg atcgagcatg gtagtctcgt gaatacggcg     1920
gatgcgtacc gtcgcgagta ccggttggat cagtttccgg tgcggctgct gcagctggcc     1980
agcttctcgt ttgacgtgtt cgtcggagac atcgcgcgga cgctgtataa cggaggcacg     2040
atggtgattg tgccgaagga tgaccggatt gatccgaacc tcttatacgg ctggattcgg     2100
gaccaaaaca ttacggtatt cgaatcgacg cctgcgctca tcctgccgtt catgcagcat     2160
atttatgaag aagggctgga cgttagctcc atgcagttgc tgattaccag ctcggatgct     2220
tgcagtgtca ccgattaccg attgctgcag gaaagattcg gcggacaatt ccgcatcatc     2280
aacagctatg gcgttaccga agcggccatt gacagcagct tttacggtga gccgctggat     2340
aagctgccgc cgtcgggtca tgtgccgatc ggcaaagctt ggctgaacgc ccggttttac     2400
attgtcgatg ccgcgttaaa gccggttcct gtaggggttc cgggcgagct tgtcatcggc     2460
ggcgccgggg tggcgcgcgg gtactggaac cgtccagacc taaccgccga gaagtttgcg     2520
gacagcccgt ttgtgccggg cgaacgtctg taccggacag gcgatttggc ccgctggctg     2580
gaagacggca acgtcgactt catcggccgg atcgactatc aggtgaaaat tcgcgggttc     2640
cggatcgaac tcggcgaaat tgaaacggcc ctgctgcgtt tcccgggcgt caagcaggct     2700
gtggtgaccg accgtacgga tgagcagggg gaaaagtatt tgtgcggcta cgtggcggcg     2760
gatgcttcct tgcagctgag cgatttgctg tcccaattga agcaagagct gccggcccat     2820
atggtcccgg cccggctggt gtctcttgat aagcttccgc tcacgccgaa cggcaaaatt     2880
gaccgtaaag cgctgcctga accgaccgga gaggtagaag caggccgtga gtatgtggct     2940
cctcgcacaa cgctggaaac aagacttgct ctcatttggc agcaggtgct gggtattgcg     3000
cgagttggag tccaagacga ttttttgac ttgggtggtc attccttgcg ggcctccacg     3060
ctggtttcca agattcggaa agagctgcaa gtcgaggttc cgctgcgcga gttttccgc     3120
tacaccacga tcgaacagct ggcccaaaga atcggcggtt taaggcagca ggagacgtat     3180
gagattacaa aggcggctga ggccgagtac tatccggttt catccgagca aaagcgtctg     3240
tacgtcctgc gccagcttga cggggccgag cgcagctaca atatgtcggc ggcgcttctt     3300
```

-continued

```
ctcgaaggca agctggaccg catgcgcgtc gagcacgcgt tccgggcgct gattcagcgc    3360
catgagacgc tgcgtacggg aatcgagcag gttcaaggcg agcttgtcca gcgcatctat    3420
gacgaggtcg agtttgctgt ggattatttc caggcgagcg agcgggaagt ggagcaagtg    3480
gtggaagctt actatcaccc gtttgatctg accaagccgc cacttctccg catcggcctg    3540
atcgaagtcg ccgaggatcg ccacattctg ctgttcgata tgcaccatat cgtctcggat    3600
ggcatttcga cagcgctgct cttcgacgag ttcagccgcc tgtatcgggg cgaggagctg    3660
ggcccgctgc gcattcaata caaagattat gccgtttggc agcattccga agcttacggg    3720
cagatgctcc agccgcagaa ggagtattgg ctggaacagc tgtcgggcga gctgccggtc    3780
ttggagctac cgacggactt cccgcggcct gcggtgcaaa gctttgacgg tcgaaccgtg    3840
aagtttata tcgagaaaga tcggacggag aagctgaaag agctggcggc acggacaggg    3900
acgaccctgt acatggtgct gctgtcggct tacaccatcc ttatgcataa atattcgggt    3960
caggaagatc tgatcgtagg aacgccgatt gccggaagaa cgcaggaaga agtgcagccg    4020
atcgtaggga tgtttatcaa cacgctggcc attcgcagcc gtccggagcg ttccaagccg    4080
taccttcgt acctggaaga aatcaaggac atcacgctcg gggctttcga acaccaaaat    4140
tatttgttcg aagacttggt ggaaagtctt catattccac gcgcgaccgg ccggaatccg    4200
ctctttgaca cgttcttctc cctacaaaat acggagaacg agcaaattgt catcgagggg    4260
ctggagcaat cgtttatcc gctggaaaac caaacatcca agttcgagct gctcctggat    4320
atttcggagc tggacggtca gctcgaatgc cggttagagt acgctacggc tttgtataaa    4380
caggagaccg cggagcggtt cgccagacat tatgacaagc tgcttgaaac catcgcagca    4440
gcgccggacg gggatattgc ctcgctggaa atgctcaagg aggaggaaat ccgcgagctg    4500
gtgcgcggtt tcaacgattc ggaggcggac tacccgcggc agcagacgat tcacggcttg    4560
ttcgaagaac aggcggagct ttacccggac aacgtggccg ccgtcatgaa cgagcggcaa    4620
ctgacctacc gcgagctgaa cgagcgatcc aaccgccttg cgcggaagct gcgagagacg    4680
ggagtagaag cggaccagct ggtagcgatt ctggccgaac gctcgctcga tatggtcgtc    4740
ggcattctgg cgattctcaa agcgggcgga gcctacgtgc ctgtcgatcc cgactacccg    4800
gaggagcgca tccgcttcat gatcgaggat tcgggcgcgc cgttattgct gattcaaaag    4860
catctgcacg agaagaccga cttcgcagga acgcgcctcg aattggacga tttcgtttgg    4920
ggcgacagag gggcgaactc cgccgaagcg ctggacgctt cgaacctgga gccaatttcc    4980
gggccgggca acctggcata tgtcatctac acgtcgggaa cgaccggcag accgaaagga    5040
acgctgatcg agcataagaa cgtcgtgcgg ctcctgttca acgacaagaa cctgttcgac    5100
ttcgggccgt ccgacacgtg gacgctgttc cactcgttct gcttcgattt ctccgtctgg    5160
gaaatgtacg gagcgctgct gtacggaggc aagctggtca tcgtaccgcc gctcacggcg    5220
aaaaatccgg ccgatttcct ggcgctgctg ggccgcgaac aggttaccat tttgaaccag    5280
acgccaacat acttctacca gctgctgcgt gaggtcttgg cggaccatcc gtacgatctg    5340
cggattcgca acgtcatctt cgggggcgaa gcgctgagtc cgctgctgct caagggcttc    5400
aagacgaagt acccggagac gaagctgatc aatatgtacg gcattaccga cgacggtt    5460
cacgtgacgt ataaggaaat cacgtgggtc gaaatggagg cggcgaagag caatatcggc    5520
aagccgatcc cgacgttgag ggtgtacgtc ctagatgaaa accgccgccc tgtgccgatc    5580
ggcgtagcgg gcgaaatgta cgtggccggg gaaggccttg cgagaggata cctgaaccgt    5640
```

```
ccggatctga cggcggagaa gttcgttgat tccccgtttg cggaggggga gaaactgtac   5700
cgttcgggcg acttggcggc ttggctgccg gacggcaaca tcgaatacct gggccggatc   5760
gaccaccagg tcaaaatccg tgggtaccgg atcgagctgg acgaaatcga acgcagctt    5820 ctgaacgtcc ggggtgtgga agaagcggtg gtgctcgccc gtcaggacgg cggggggcgag   5880 aaggcgcttg tcgcctactt tgtggcggac cggacgctga cggtcagcga atgagaacc    5940 tcgctggccc agggaatgcc ggggtacatg atcccgtcgt acttcgtgca gttggagcgc   6000
atgccgctga cgaccaacgg caaagtggac cgcaaagcgc tgccggagcc gcaaggcggc   6060
atacaaacgg gtgtcgaata cgtagcgccg cgtaactgga cggagtccca gcttgtgaag   6120
atctgggagg aagtgctggg ttactccggc attggagtcc tggacaattt cttcgagctc   6180
ggaggccact ccttgcgggc gacgaacctt gtcagcaaga ttcggaagga aatgaacgtc   6240
gaacttccac tgcgtgatgt gttccgctat acgacggtag agtcgatggc cggggctatt   6300
gccagcttgg aagaaacaca gcacagctcg attccgaaag cggaagagaa agcgtactat   6360
ccggtttcct ccgcgcaaaa aaggctgtac gtcctgcacc agctggatag ctcggagctg   6420
aattacaacc tcccaagcgc cttgcaattg aagggggctt tgaacgaggc caaagtggaa   6480
aaggcactga ctactttggt ggcccggcac gatatgctgc gcaccggttt tgaaatcgtg   6540
aatggggagc cggttcagcg tattcatccg ctcgtagctt tcaaggtcga gaagcttcaa   6600
gcaagcgaag atcaggttgc ggccattctt gaaggcttca ttcagccttt tgacttgacc   6660
cagccgcctt tgctgcgcgc cctgctgatc gaactggaga aagagaaatt tctgctcgcg   6720
ctggatattc atcatattgg ttccgacggc ctttccatgg acgtgctgct gcgcgaattc   6780
gtgcggcttt acaatgggga ggaattgccg gagctgcgga ttcaatacaa ggattacgcc   6840
gtttggcagc aatccgagga gcagcgccag cgcatcaaac ggcaggagga atactggcgc   6900
ggggtattca gctccgagct tccggttctt gagctgcctc tcgacttctc ccgcccggcc   6960
gttcagcagt ttgacggtca aacgctcacg tttacgctgg atgcggagaa aagcgaagct   7020
ctcaaacggc ttgccggcga ttcggggcg acgctgtaca tgcttctgct ggctgcgtac   7080
tccgtattgc ttcataaata cgcgggacag gaagatatag tggtcggcac tccgattgcc   7140
gcccgttctc acgccgacct gcagccgatt atcggcatgt tcgtcaatac gctggccctt   7200
cgtttgcgtc cggcggcgga gcggacgttc ctggattact tgcaggaagt gaaggaaacg   7260
acgcttggag cctacgagca ccaggactat ccgttcgagg agttggtgga agctcttcag   7320
gtgagccggg atttaagccg gaatcctctg tttgacacca tgttttcttt gcaaaagcac   7380
gaaagcttgg atttaaccct ggaaggcttg caatggtcgc tgttcgacat cgaggaaaag   7440
acggccaagt ttgatcttag ctttgatatc gtggaagccg ataacgagct ggtttgcaag   7500
attgagtacg ctacctcgtt gtttagacag gaaacgatgg tacggctggc gggacattat   7560
gagcagcttt tggcgtccat cctggctcag ccgggtgcgc ggattcgga tttggatatc    7620 ttgacggaca gcgaaaagca tgatttgctg gtcgggtttg acgtgtcgtc ttcggctctt   7680
gcgaagcaac ccgccgcaga aggtacaggt ttggaagcgg atgagtcgtg gagagagaga   7740
acgttccacg agctgttcga ggagcaggcg gagcgcactc cgggagcgct ggcggttgtc   7800
tacgaagaca gcaagctgac gtatgcggag ctgaacgcca aagcgaatcg tctggcgtat   7860
gcactgcggg cgcgcggtgt gaagccggag caggtggtcg gcattctggc cggccgttca   7920
gcagagctgt tggttggtgt gcttgccgta tggaaagcgg cggcgctta tgtgccgctc    7980 gaccccggatt atccggcgga acggatcgaa tatatgctcg cggacagcgg ggcgtcggtg   8040
```

```
ctgctcacgc agacctgcct gctggagcag gcggaagctt ggcgcagcga cggagctcta    8100
gtgctgcaaa cggtgcttgc gcttgacgac gccgcgacgt acagcctcgg agcggcggaa    8160
gcggctgtgg gcgtacaagc tttgggtgaa gcaggcgcag aggcggaggc tttggcgcaa    8220
gcggaaacgg ctgctgccga aaaatccgcc acggcagaag ccgagaagaa cgtactagcg    8280
gcggatctcg catcgaatcc ggcgaatgtg aacaagccga gcgatttggc ttacgtcatc    8340
tacacctccg gtacgacggg ccgtccgaag ggcgtggcgg tggaacaccg cagcttggtg    8400
aacacgcgg cgggctaccg gcgggactac cgcctggatc agttcccgat ccggctgctg    8460
cagctcgcca gcttctcgtt tgatgtgttc gtcggtgata ttgcgcggac gctgtacaac    8520
ggcggcacta tggtcatcgt gccgaaggac gaccggattg atccaacccg cctctacggc    8580
tggattcgcg actacgccgt gacggtgttc gaatcgactc cggcgctgat cgtgccgttc    8640
atggagcatg tgcatgccga gggtctggat ctcagctcga tgcagctgct gatcacaagc    8700
tcggatgcgt gcagcgtagc ggattaccgc accttgcagg agcgcttcgg ctcgcagttc    8760
cgtattatta acagctacgg cgtaacggaa gcggcgattg actccagctt ctatgacgag    8820
ccgctggaga agctgccgaa gacgggcagc gtgccgatcg ggaaagcgtg gctgaacgcc    8880
aagttctaca tcgtggatgc gaatctgaag ccggtgccga tcggggtgtt gggcgagctg    8940
gttatcggcg gagcgggtgt ggcccgcggt tacttgaacc gcccggattt gacggcggag    9000
aaattcgtag acagcccgtt cgccgctggg gagcggctgt accggacggg cgacctggct    9060
cgctggatgc cggacggcaa cgtggacttc atcggccgga tcgacaacca ggtgaaaatt    9120
cgcggctatc ggatcgagct tggtgaaatt gaagcggcca tgaaaaattt tgccggcgtg    9180
cgtcaagcgc ttgtcatcga ccggacggac gagcgggggc agaaatattt gtgcgggtat    9240
gtcgtagcgg attccagctt cgatctggaa gggcttgtgg cccatctcga cgccgcgctg    9300
ccttcccata tggtgccttc gcgcatcatg cgcctggatc aaatgccgct tacgccgaac    9360
gggaagatcg accgtaaagc gctgcctgta ccggaaggaa gcattcgtgc cgaggctgca    9420
tacacggcgc ctcgtactcc tgccgagcaa gcacttgcgt cggtctggca gtcggtgctg    9480
ggcgtggacc aggtcggcac gatggacaat ttctttgcgc tcggcggcga ttcgatcaag    9540
gccttgcagg tatcgtcccg tcttttgcaa acggggtaca agctggtcat gaaagatttg    9600
ttccattacc cgacgatttc cgcccttagt ttgcagctgc aaacggcgga gagaacggca    9660
agccaggcca aagtgacggg agaggtcatc ttgaccccga ttcagcgctg gttcttgaa    9720
caaaatccgg ccgacgtgca tcacagcaac caggcgttca tgcagttctc caaggaaggc    9780
tttgacgaag aagctttacg ccaagcggtg cgtcagattg tcgtgcatca cgatgctctc    9840
cgtacggttt accgccaagc cgacaacggc tataccgcct ggaaccgcgg cgccggggag    9900
aacgaagcgc tgttcgatct ggaagttgtc gatttcaagg gagtcggcga cgtgaaagaa    9960
gcggtagagg ctaaggcgaa tgacattcaa gcgagcatcg atctggaaaa cggtccgctg    10020
gtgaagctcg gcttgttccg ctgcgacgac ggcgaccacc tactcatcgc gatccatcac    10080
ttggtcgtag acggcgtatc ctggcggatt ctgcttgagg attttgctgc cggctatgag    10140
caggcgctgc aagggcagcc gatccgtctg ccgctcaaaa cggattcatt ccaaacgtgg    10200
gcgaaacagc tcgctgatta tgcgaacagc ccggcgatgg aaagcgagag agagtattgg    10260
cagcatatcg agcaattgac ctatgagccg cttccgaaag attttgaaca aggcagatcc    10320
aagctgaagg acagcgggct cgtgaccgtt cgctggacgg cggaggaaac cgaacagctg    10380
```

-continued

```
ctgaagcagg cacaccgtgc ttaccatacg gaaatgaacg atttgctgct tgccgcgctt    10440
ggcctcgctt tacaagcttg gagcggccgg gaacgcgtgc tggtgaatct cgaaggccac    10500
ggccgggaag atattttgcc ggatgtggac attacgcgca cggtaggctg gtttacaagc    10560
caattccctg tcgttctgga gccgggtcac gcccaggcgc tcggtcatca ggtgaaacag    10620
gttaaagaaa gcttgcgccg cattccgaac aaaggaatcg gctacggcat cctgcgttat    10680
ttgtcggcgc cgcgtgaagg cgagtacttc gttttagagc cggagatcag ctttaactac    10740
ctgggtcagt tcgaccatga ttacgaaagc agcagctcgc agccgtcccc gttcagcccg    10800
ggctccgact caagcccgaa tgctgtgatg gattatgtcc ttgatatcaa cggtatggtg    10860
tcggaaggag cgttggaact cacgatccgt tatggggaaa cccagtataa acgggaaacg    10920
gtggagcgtc tgggcaccct gcttcaatcg agcttgcgtg aagtcatcag ccattgctta    10980
tcaaaagagc ggccggagct tacgcctagc gacgtactgc ttcaagatgt gacggtggag    11040
gaactggagc ggctgtccga acatacggtg gcgctcggcg aactggagaa tgtatacacc    11100
ctgactccac tgcaaaaagg gatgttgttc cacagcttgc tggatgccga ttcggaagct    11160
tacttcgaac aggtgacctt cgatctgtac ggaagcctga atgtggaagc cttcaccccga   11220
ggattggata cgctggtgca gcggaatgag cgctgcgga ccaactttat taccggctgg     11280
agagacgagc cgattcaagt ggtattccgc gagcggaagt gtgaagtgta cttcgaagat    11340
attcgttcgg taagcgatga acacccggag aagacgatag ccgattttgt cagcgcggat    11400
aaagcgaaca agttcgatct ggcccgaggt cctcttatgc gtgtgaccgt tgtgcgcaca    11460
ggcgacgagt cctaccatgt gatctggagt catcatcaca tttttgatgga cggctggtgt   11520
atgtccttca tgatcaagga agtgttcgac acctacttcg cgttccagga gaagcggacg    11580
ctggagcttc ctccggttac ctcgtactcc cggtatatcg aatggctgga agctcaagat    11640
gccgcgaaag cttcgcgtta ctggtccgag tatttggcgg gttacgatca gcagaccaag    11700
ctgccccagg agaaaacgca gctgaagcag gcgcttttg aagcggctga aatcgatgtg     11760
gaactcagca aggaactgac cgggcaaatc gagcgggtgg cgcgccagca gcaggtgaca    11820
ctcaatacgt ttatgcagac tgtatgggga ctggttctac agatatacaa caacagcgag    11880
gatgtcgtat tcggctccgt tgtatccggg cgtccggcgg aaattccggg catcgaaagc    11940
atgattggcc tgtttattaa tacgatcccg gtccgtattc aaggtaaagc cgaggagagg    12000
gtagccgata tcttgagaaa aacccaggat caagcgctgg catcgggagc atatgaaacg    12060
ttcccactgt tcgaaattca gtccctgagc gagcaaaagc gcgacctgat caaccatatt    12120
atggtctttg aaaattatcc gatggaagaa cagatcgagc aggtcgtcgg tggaggccga    12180
gaagcgctga aaatcgctaa tatccagtcg ccggagcaaa cgaactacga cctggacatt    12240
accgtcattc cggaagagca tattttgctg cggtttacgt acaatgcgct aacgttcaga    12300
gaggatgaca ttaggcagat ccacagtcat tttgcctggg cactggagaa ggttgcggct    12360
aaccccgaaca tcctcgtgaa tcagttggag cttttgacgg cggcggaaaa agagcaaatt    12420
ctcggcgcgt ttaacccggc gcagccgaa gcggctcctg cggccgcgtt ccaccggctg     12480
ttcgaggaac aggtggagcg cacgccggaa gaggcggccg tcgtgtacga gaatgaccgg    12540
ctgacgtatg cggagctgaa cgagcgggcg aaccgcttgg cggctacgct gcgcgcaagc    12600
ggcatcggcc gggagacgat cgtcggcatt ctcgccgagc gttcggtgga cttgctggtg    12660
gccgtgctgg ccgtctggaa agcgggcggg gcgtatgtgc cgctcgaccc ggattatccg    12720
gcagaccgcg tgcggttcat gcttgaagac agcggagcga aggtgctgct gacgcaaacg    12780
```

```
gcgctgcgag agcgtgccga agcctggctc ggcgaagagg agctggcgct ggcggcggtg   12840
ctgtacctgg acgacgaagc gtcgtacaac gaggagcggg cgaatgcgcc ggttggctcc   12900
ggcatggtct ccggcaagct gacggatgct gtggacgacg cgatgagag ccatcagaat    12960 gttggcaccg acggcttcca tgaagcccgt ccggaggacc tggcgtacgt gatctatacg   13020
tcgggaacga cgggcaagcc gaagggcgtg atgatcgagc accgcagcct ggtgaacacg   13080
gcggcgggct accggcggga ataccggttg gatcagttcc cggtgcggct gctgcagctc   13140
gcaagcttct cgttcgacgt gttcgtggga gatatcgcgc ggacgctgta caacggaggt   13200
acgatggtga ttgtgccgaa ggacgatcgg attgatccgt ctcgtctgca ccactggatg   13260
gagcgggagc gggtcaccat cttcgaatcg acgccggcgc tgatcgtgcc gttcctggag   13320
tacgtgcacg atcagcagct ggatatgagc tggatggagc tgttgatcac gagctcggac   13380
agctgcagcg tggcggatta ccggaccttg caggaacgct tcggctcgtt gttccgaatc   13440
atcaacgcct acggcgtgac ggaagcggcg atcgactcca gcttctacga cgaggagctg   13500
gcgaagctgc cgcagacagg ccatgtgccg atcggcaaag cgtggctgaa tgcgaaattc   13560
tacatcgtgg acgcgcatct gaacccggtg ccagtcgggg tgctgggcga gctggtcatc   13620
ggcggagtcg gagtggcgcg cgggtacttg aaccgtccgg aactgacggg agagaagttc   13680
gtagacagcc cgttcgccgc gggcgagcgg ctgtaccgca cgggagactt ggcgcggtgg   13740
atggaggacg ggaacgtgga cttcatcggc cggatcgaca accaggcgaa aatccggggg   13800
taccggattg agacgggcga agtcgaagca aagctgctga gtgtaggtgg cgtgaaggaa   13860
gcggtcgtcg tcgtcaggga agatcaagaa ggtcagaaag ctttgtgcgc ttattataca   13920
gcggaagaag gcttgacggc ggcggatctg aagcgggcga ttgccagcga gctgccgggg   13980
tacatgatcc cgtcgtactt cgtggagctg gagcgcctgc ctctgacgcc gaacggaaag   14040
atcgaccgga aggcgctgcc ggcaccggaa gggggagcag gcggaggccg cgaatacgtg   14100
gcgccgcgca ccgaacttga ggcgaagctg ccgccatttt ggcaggatgt gcttgttcgg   14160 gagaaggcg taggcgtaac ggacaacttc ttcgacctcg gcggacactc cctgcgggca    14220
acgacgcttg tcagcaaaat gcataaggag ctaggcgttg aattcccgct tcgcgacgta   14280
ttccgctacc cgacggttga ggaaatggcc gcggctatgg agcggctgga gatcggctcg   14340
ttcatggcta ttccggctgc ggaacctagc gagtattatc cgctctcttc cgctcagaaa   14400
cgtctctata tcttgaacca gctggaagga gccgagctga gctacaacat accgggagct   14460
atgctgctcg aaggggagct cgaccggcag cggtttgaag aagcgttccg cgggctcgta   14520
gctcgccatg aaaacgctgcg taccggcttt gagatggtaa aaggcgaagc ggttcagcgg   14580
atttacgaag aagccgcctt ccaggtggaa tatgtgcaga tcagcgcgga gcaggcggaa   14640
gaaacggtgc gccaattcgt tcgtccgttt gatctagcga agccgccact tctgcgggta   14700
ggccttgccg aactggcgcc ggaccggcac attctaatgt tcgatacgca tcatatcgta   14760
tctgacggcg tttcgattga tgtactgatc gaagagttgg tccgcttgta cagcggggag   14820
cagttggagc cgctccgcat tcagtacaaa gattatgcgg tatggcagca atcggacgag   14880
cagaaagctc agcttgccaa gcaggaagcc tactggctcg acatgttccg cggagagctg   14940
ccggttttgg aattgccgac ggactatccg cgcccggcta tgcagagcta cgagggccgc   15000
acgctgcaat tgtttatgca tagcgagaaa agcgagggtc tgaaacggct tgcagccgag   15060
aacggcgcaa cgctttacat ggttctgctt gctggttata caatattatt gcataaatat   15120
```

```
acaggacaag aagacgtggt ggtcggtacg ccgattgcgg gaagaaatca cagcgatgtt   15180
cagccgctga tcgggatgtt cgtcaatacc ctggccatcc gcagttatcc ggctgccgat   15240
aagacgttcc ttgagtactt gaaggaaatc aaggagacga cgctgggcgc ttttgaacat   15300
cagaattatc cgtttgagga actggtggat aaggtgaacg tggctcgtga tttacgccgc   15360
aatccgctgt tcgatacgat gtttgctttg cagaatacag agaatttgga aatccagctt   15420
cccggactcc atttgtcgac gtatgccagc gaagaaattg tttctaaatt cgatctcagc   15480
ttggacgtca cggagatcga ggaaggcttg gaatatctgt ttgaatacgc cactgctctt   15540
tataaaaccg aaacggtgga gaaattggcc gctcactact tgcagctgct tgaatccatt   15600
ctccgcaacc catcggcgac tattgccgag ctgggcattt tgacaccggc ggaaaaagag   15660
caaattctcg gcgcgtttaa cccggcgcag ccggaagcgg ctcctgcgac cgcgttccac   15720
cggctgtttg aggaacaggt ggagcgcacg ccggaagagg cggccgtcgt gtacgagaat   15780
gaccggctga cgtatgcgga gctgaacaag cgggcgaacc gcttggcggc tacgctgcgc   15840
gcaggcggca tcggccggga gacgatcgtc ggcattcttg ccgagcgttc ggtggacttg   15900
ctggtggccg tgctggctat ctggaaagcg gcgggggcgt atgtgccgct cgacccggat   15960
tatccggcag accgcgtgcg gttcatgctt gaagacagcg gagcgaaggt gctgctgacg   16020
caaacgccgc tgccgagagcg tgccgaagcc tggctcggcg aagaggagct ggcgctggcg   16080
gcggtgctgt acctcgatga cgaaacgtcg tacagcgagg agcgggcgaa tgcgccgatt   16140
ggctccggca tggtctccgg caagctgacg gatgctgtga acgacggcga tgagagccat   16200
cagaatgttg gcaccgacag cttccatgaa gcccgtccgg agaacctggc gtacgtgatc   16260
tatacgtcgg gaacgacggg caagccgaag ggcgtgatga tcgagcaccg cagcctggtg   16320
aacacggcgg tgggctaccg gcgggaatac cggttggatc agttcccggt gcggttgctg   16380
cagctcgcaa gcttctcgtt cgacgtgttc gtgggagata tcgcgcggac gctgtacaac   16440
ggaggtacga tggtgattgt gccgaaggac gatcggattg atccgtctcg tctgcaccac   16500
tggatggagc gggagcgggt caccatcttc gaatcgacgc cggcgctgat cgtgccgttc   16560
ctggagtacg tgcacgatca gcagctggat atgagctgga tggagctgtt gatcacgagc   16620
tcggacagct gcagcgtggc ggattaccgg accttgcagg aacgcttcgg ctcgttgttc   16680
cgaatcatca acgcctacgg cgtgacggaa gcggcgatcg actccagctt ctacgacgag   16740
gagctggcga agctgccgca gacaggccat gtgccgatcg gcaaagcgtg gctgaatgcg   16800
aaattctaca tcgtggacgc gcatctgaac ccggtgccag tcggggtgat gggcgagctg   16860
gtcatcggcg gagtcggggt agcgcgcggg tacttgaacc gtccggaact gacggaagag   16920
aagttcgtag acagtccgtt cgccgcgggc gagcggctgt accgcacggg agacttggcg   16980
cggtggatgg aggacgggaa cgtggacttc atcggccgga tcgacaacca ggcgaaaatc   17040
cggggctacc ggatcgagac gggcgagatc gagtcgcagc tgctgcgggt ggaaggcgtg   17100
cgcgaagcgg tggtgctggt tcgaagtgac tcgaacgggc agaaagcgct gagcgcgtac   17160
tacacaattg atggcgaact gacgcgcgca gacctgaaac gggcgatctc cagcgagctg   17220
ccgggttaca tgatcccgtc gtacttcgtg gagctggagc gcctgcctct gacgccgaac   17280
gggaaaatcg accggaagga gctgccggcg ccggaagggg gagcaagcgc aggccgcgaa   17340
tacgtggcgc cgcgcaccga actggaggcg aaactggtcg ccatctggca ggacgtgctc   17400
gggccgatca cgattggcgt gacggacaac ttcttcgacc tcggcgggca ctccctgcgg   17460
gcgacgacgc tggtcagcaa ggtgcacaag gagctgagcg tggacctgcc gctgcgcgat   17520
```

```
gtgttccggc actcgaccat cgaagcgatg gccgaagcga tcagccaatt ggagcggcag    17580
gaacacctct ccattccggt tctggataag agggattact atccgctttc ctccgtgcag    17640
aaacggctgt atatccagca gcagatggaa ggcgccgagc ttagctacaa tatgtccggc    17700
atgacggttc tcgtcgggcg tttggaacgg aatcaattcg aggcggcgct caaaggattg    17760
atagctcgtc acgaaatttt gcgaaccggc ttcgaaatgg tcgacggcga accggtacaa    17820
cggatttatc cggacttgaa gtttgccgtc gagtatacga aagcgatgga aagtgaaacg    17880
aagagcatcg tagacggctt tgtacgcgtc tttgatttgg agcggccgcc gctgctgcgt    17940
gtgggcttag tcgaaatgga agcggaacgg catctgctca tgctggacat tcatcatatc    18000
gtcacggatg gcatgtcgat gggcatcttc gtcgaagagc tactgcgcct gtataacggc    18060
gagactctgg aaccgcttcg gattcaatac aaggaattcg ccgcttggca gcagtccgaa    18120
cctgtaaaag agcggctgaa acgtcaggaa gcctactggc tggacgtgct ggaaggcgaa    18180
ttgccgacgc ttgaactgcc tacggacttt gtcagacctg ccgctcgcag ctttgaggga    18240
gatgtgctgc ctttcagcat cgacaagcag atgaccgaca gcttgcagcg catcgccgat    18300
gagaacggtg ccacccttta tatggtgtta ttggcggcct attcaatcct gctcagcaag    18360
tactcgggac aagaagactt cattgtaggc acgccggttt cgggccgcac acatgccgac    18420
ctggagccgc tcataggaat gtttgtcaac actttggcga ttcgccatta tccgtccggg    18480
gagaagacgt tcctcgctta cttgaacgaa gtcaaagaaa caatgctggg ggcctacgag    18540
caccaggatt atccgttcga ggagcttgtg aaaaagctgc aggcaccgcg agatcaaagc    18600
cgcaatcctg tattcgatgt catgtttgct ctggaaacca aggaagataa cgttcaaagc    18660
ttcggggata tcaagatcga atcttatccg gaaactcata cggtttccca atttgatctt    18720
accttggtca tttcgttgct ggatgaggga atgaacgggc agtttgaata tgccaccaag    18780
ttgtttacgc gcaatctgat cgacaatttc gctcaggacc tgctcgtgat catcacccaa    18840
atttgcgaac agccttcggc gctgttgaag gatatttccc tgaacgggca atccgaacag    18900
gagcaagatg tgctagaggc cattgatatt attttctaa                          18939
```

<210> SEQ ID NO 4
<211> LENGTH: 4953
<212> TYPE: PRT
<213> ORGANISM: Polymyxa betae

<400> SEQUENCE: 4

```
Met Ala Phe Glu Lys Glu Thr Leu Phe Trp Asn Glu Lys Phe Gly Asn
1               5                   10                  15

Asp Asp Tyr Thr Leu Thr Arg Leu Pro Tyr Ser Lys Ala Pro Ser Ser
            20                  25                  30

Leu Ala Pro Ile Met Thr Thr Val Gly Gly Ser Leu Ser Glu Glu Ala
        35                  40                  45

Ala Gln Arg Val Leu Gln Met Ser Lys Gly Ala Pro Leu Ala Ala Phe
    50                  55                  60

Met Ile Leu Leu Ala Gly Val Gln Ser Leu Leu His Lys Tyr Thr Gly
65                  70                  75                  80

Ala Ser Asp Ile Leu Val Gly Met Pro Val Val Arg Lys Pro Thr Glu
                85                  90                  95

Thr Arg Arg Ser Val Asn His Thr Val Ile Leu Lys Asn Ser Leu Ser
            100                 105                 110

Ala Gly Ala Thr Phe Lys Thr Leu Leu Asn Glu Leu Arg Thr Ser Leu
```

-continued

```
            115                 120                 125
Pro Arg Ala Ile Gln His Gln His Ile Pro Phe Leu Lys Met Thr Glu
    130                 135                 140

Lys Leu Asp Leu Gln Tyr Ala Asp Gly Ile Pro Val Val His Thr Leu
145                 150                 155                 160

Val Ser Leu Lys Glu Leu His Leu Asp Glu Ile Gly Gln Asn Val Val
                165                 170                 175

Thr Asp Cys Ser Phe Glu Phe Ser Leu Thr Gly Gly Thr Ile Gln Leu
            180                 185                 190

Ala Leu Ser Tyr Asn Glu His Leu Tyr Asp Ser Glu Phe Met Thr Arg
        195                 200                 205

Val Val Gly His Leu Asn Arg Leu Leu Val Val Gly Leu His Glu Leu
    210                 215                 220

Glu Leu Asp Ile Val Arg Ala Asp Met Leu Ser Glu Asp Glu Lys Phe
225                 230                 235                 240

Gln Leu Leu Gln Ser Phe Asn Asp Thr Glu Lys Asp Tyr Pro Arg Asp
                245                 250                 255

Arg Thr Ile His Gln Leu Val Glu Glu Gln Ala Lys Arg Val Pro Glu
            260                 265                 270

Ala Thr Ala Val Val Phe Glu Gly Arg Arg Leu Ser Tyr Ala Glu Leu
        275                 280                 285

Asn Glu Arg Ala Asn Arg Leu Ala Arg Thr Leu Arg Ser Ile Gly Val
    290                 295                 300

Leu Pro Asn Gln Leu Val Gly Leu Met Val Arg Arg Ser Leu Glu Thr
305                 310                 315                 320

Val Val Gly Ile Leu Ala Val Leu Lys Ala Gly Gly Ala Tyr Val Pro
                325                 330                 335

Ile Asp Pro Glu Tyr Pro Glu Glu Arg Ile Arg Tyr Ile Leu Glu Asn
            340                 345                 350

Ser Asn Ala Gln Leu Leu Leu Thr Gln Arg Glu Leu Leu Gln Leu Gln
        355                 360                 365

Val Pro Phe Glu Gly Thr Val Val Ala Leu Asp Asp Glu Gln Ala Tyr
    370                 375                 380

Ser Asp Asp Gly Ser Asn Leu Glu Pro Ala Ser Gly Pro Asn Asp Leu
385                 390                 395                 400

Ala Tyr Val Ile Tyr Thr Ser Gly Thr Thr Gly Asn Pro Lys Gly Val
                405                 410                 415

Met Leu Glu His His Gly Leu Val Ser Leu Lys Leu Met Phe Ala Asp
            420                 425                 430

Arg Leu Gly Ile Thr Glu His Asp Arg Ile Val Gln Phe Ala Ser Leu
        435                 440                 445

Ser Phe Asp Ala Ser Cys Trp Glu Val Phe Lys Ala Leu Tyr Phe Gly
    450                 455                 460

Ala Ala Leu Tyr Ile Pro Thr Ala Glu Thr Ile Leu Asp Asn Arg Leu
465                 470                 475                 480

Phe Glu Ser Tyr Met Asn Glu His Ala Ile Thr Ala Ile Leu Pro
                485                 490                 495

Pro Thr Tyr Ser Ala Tyr Leu Asn Pro Asp Arg Leu Pro Ser Leu Thr
            500                 505                 510

Lys Leu Val Thr Gly Gly Ser Ala Val Ser Ala Glu Phe Val Gln Gln
        515                 520                 525

Trp Lys Arg Lys Val His Tyr Phe Asn Ala Tyr Gly Pro Thr Glu Ala
    530                 535                 540
```

```
Ser Ile Val Thr Thr Leu Trp Asp Ala Asp Glu Glu Gln Pro Glu Gly
545                 550                 555                 560

Arg Val Ile Pro Ile Gly Arg Pro Leu Ala Asn His Arg Ile Phe Ile
                565                 570                 575

Leu Asp Ala His Leu Gln Leu Val Pro Pro Gly Val Asp Gly Glu Leu
            580                 585                 590

Cys Val Ala Gly Val Gly Leu Ala Arg Gly Tyr Leu Asn His Pro Glu
        595                 600                 605

Leu Thr Ala Glu Lys Phe Val Glu His Pro Phe Ala Pro Gly Glu Arg
    610                 615                 620

Leu Tyr Arg Thr Gly Asp Leu Ala Arg Trp Leu Pro Asp Gly Asn Val
625                 630                 635                 640

Glu Tyr Leu Gly Arg Ile Asp His Gln Val Lys Ile Arg Gly Phe Arg
                645                 650                 655

Ile Glu Ile Gly Glu Ile Glu Glu Gln Leu Leu Lys Ile Asp Ser Val
            660                 665                 670

Gln Glu Thr Ile Val Ile Ala Arg Glu Gly Lys Ser Gly Gln Glu Leu
        675                 680                 685

Cys Ala Tyr Leu Val Ala Gly Arg Pro Leu Thr Leu Gly Glu Leu Arg
690                 695                 700

Ser Ala Leu Ala Gln Lys Leu Pro Asn Tyr Met Ile Pro Ala His Phe
705                 710                 715                 720

Val Gln Leu Pro Gln Met Pro Leu Thr Pro Asn Asp Lys Ile Asp Arg
                725                 730                 735

Lys Ala Leu Pro Ala Pro Glu Gly Asn Ala Leu Thr Gly Gly Ala Tyr
            740                 745                 750

Val Ala Pro Arg Asn Glu Ala Glu Arg Thr Leu Ala Asp Val Trp Gln
        755                 760                 765

Ala Val Leu Asn Ala Asp Arg Val Gly Val Thr Asp His Phe Phe Glu
770                 775                 780

Leu Gly Gly Asp Ser Ile Lys Ser Ile Gln Val Ser Ser Arg Leu His
785                 790                 795                 800

Gln Ala Gly Tyr Lys Leu Glu Ile Arg Asp Leu Phe Lys Tyr Pro Thr
                805                 810                 815

Ile Ser Gln Leu Ser Leu His Val Lys Pro Ile Gly Arg Thr Ile Asp
            820                 825                 830

Gln Gly Glu Ile Thr Gly Glu Thr Ala Leu Thr Pro Ile Gln His Trp
        835                 840                 845

Phe Phe Glu Ser Ser Phe Ala Asp Pro His His Phe Asn Gln Ser Val
850                 855                 860

Met Leu Tyr Arg Lys Glu Arg Phe Asp Glu Thr Val Arg Gln Val
865                 870                 875                 880

Leu Gln Lys Leu Ala Glu His His Asp Ala Leu Arg Met Val Phe Arg
                885                 890                 895

Lys Thr Glu Gln Gly Phe Ser Ala Arg Asn Arg Ala Ile Gln Asp Gly
            900                 905                 910

Gly Leu Phe Thr Leu Asp Val Phe Asp Phe Lys Asp Ala Glu Asn Thr
        915                 920                 925

Glu Gln Ala Val Glu Ala Lys Ala Thr Asp Ile Gln Ala Gly Ile Asp
930                 935                 940

Leu Glu Asn Gly Leu Leu Leu Lys Ala Gly Leu Phe Arg Cys Ala Asp
945                 950                 955                 960
```

```
Gly Asp His Leu Leu Ala Val His His Ala Val Val Asp Gly Val
            965                 970                 975

Ser Trp Arg Ile Leu Met Glu Asp Phe Ala Leu Gly Tyr Glu Gln Ala
            980                 985                 990

Gly Lys Ser Glu Glu Ile Arg Phe Pro Ala Lys Thr Asp Ala Tyr Arg
        995                 1000                1005

Thr Trp Ser Glu Gln Leu Ala Ala Tyr Ala Gln Ser Pro Glu Met
        1010                1015                1020

Thr Lys Glu Arg Ala Tyr Trp Gln Ala Met Glu Gln Ile Ala Val
        1025                1030                1035

Pro Ala Val Pro Lys Asp Leu Asp Val Asp Val Thr Thr Gln Gln
        1040                1045                1050

Asp Ser Glu Ser Leu Phe Val Arg Leu Thr Pro Glu Glu Thr Glu
        1055                1060                1065

Leu Leu Leu Lys Arg Val His Arg Ala Tyr Asn Thr Glu Met Asn
        1070                1075                1080

Asp Ile Leu Val Thr Ala Leu Gly Ile Ala Ile Arg Lys Trp Thr
        1085                1090                1095

Gly His Glu Arg Val Arg Ile Asn Leu Glu Gly His Gly Arg Glu
        1100                1105                1110

Ser Ile Gly Thr Asp Ile Asp Ile Thr Arg Thr Val Gly Trp Phe
        1115                1120                1125

Thr Thr Lys Phe Pro Val Val Leu Glu Pro Glu Thr Asp Arg Asp
        1130                1135                1140

Leu Ala Tyr Gln Ile Lys Gln Val Lys Glu Ser Leu Arg Arg Ile
        1145                1150                1155

Pro Asn Lys Gly Leu Gly Tyr Gly Val Cys Arg Tyr Leu Ser Lys
        1160                1165                1170

Ser Glu Asp Gly Phe Val Trp Gly Ala Glu Pro Glu Ile Asn Phe
        1175                1180                1185

Asn Tyr Leu Gly Gln Phe Asp Asp Val Ser Gln Val Glu Ile
        1190                1195                1200

Gly Ile Ser Ser Tyr Ser Ser Gly Ser Pro Ala Ser Asp Arg Gln
        1205                1210                1215

Ala Arg Ser Phe Val Leu Asp Ile Asn Gly Met Val Leu Asp Gly
        1220                1225                1230

Ala Leu Ser Leu Asp Leu Ser Tyr Ser Arg Lys Gln Tyr Arg Lys
        1235                1240                1245

Glu Thr Met Glu Ala Phe Ala Gln Arg Leu Glu Gln Ser Leu Arg
        1250                1255                1260

Glu Leu Ile Thr His Cys Ala Gly Lys Glu Asn Thr Glu Leu Thr
        1265                1270                1275

Pro Ser Asp Val Gln Phe Lys Gly Leu Thr Ile Ala Glu Leu Glu
        1280                1285                1290

Gln Ile Ala Gln Arg Ser Gly His Leu Gly Glu Ile Glu Asn Ile
        1295                1300                1305

Tyr Ser Leu Thr Pro Met Gln Lys Gly Met Trp Phe His Ser Ala
        1310                1315                1320

Leu Asp Arg Gln Thr Ala Ala Tyr Phe Glu Gln Thr Arg Phe Thr
        1325                1330                1335

Met Arg Gly Ala Leu Asp Val Gln Leu Phe Glu Arg Ser Trp Met
        1340                1345                1350

Glu Leu Ala Lys Arg His Leu Val Leu Arg Ala Asn Phe Val Lys
```

-continued

```
            1355                1360                1365

Gly Pro Glu Gly Glu Pro Leu Gln Val Ile Tyr Arg Asp Lys Pro
        1370                1375                1380

Val Gly Phe Glu Tyr Glu Glu Leu Leu His Leu Gln Ala Asp Glu
        1385                1390                1395

Lys Gln Ala Tyr Leu Asp Lys Lys Ala Glu Asp Asp Lys Leu Arg
        1400                1405                1410

Gly Phe Asp Met Glu His Asp Ala Leu Val Arg Val Thr Ile Leu
        1415                1420                1425

Arg Thr Glu Glu Gln Ser Tyr His Val Leu Trp Ser Phe Gln His
        1430                1435                1440

Ile Leu Met Asp Gly Trp Cys Leu Pro Gln Leu Thr Gln Glu Leu
        1445                1450                1455

Phe Glu Met Tyr Ser Ala Leu Ala Ser Gly Lys Gln Pro Ala Gly
        1460                1465                1470

Asp Lys Gly Ser Asp Tyr Gly Ala Tyr Ile Glu Trp Leu Glu Lys
        1475                1480                1485

Gln Asp Asp Gln Ala Ala Ser Gly Tyr Trp Thr Ala Phe Leu Ala
        1490                1495                1500

Asp Tyr Glu Gly Gln Thr Val Leu Pro Gly Gln Lys Glu Pro Ala
        1505                1510                1515

Pro Ser Gly Ile Phe Thr Ala Asp His Val Thr Ala Glu Leu Gly
        1520                1525                1530

Lys Asp Leu Ser Glu Arg Met Asp Arg Val Ala Lys Gln Arg Leu
        1535                1540                1545

Val Thr Val Asn Thr Leu Leu Gln Ala Ala Trp Gly Val Met Leu
        1550                1555                1560

Gln Lys Tyr Asn Gly Thr Asn Asp Ala Val Phe Gly Ser Val Val
        1565                1570                1575

Ala Gly Arg Pro Ala Glu Ile Pro Gly Ile Glu Ser Met Ile Gly
        1580                1585                1590

Leu Phe Ile Asn Thr Val Pro Val Arg Val Thr Ser Glu Ala Asp
        1595                1600                1605

Thr Val Phe Ala Asp Leu Met Ala Lys Leu Gln Glu Arg Ala Leu
        1610                1615                1620

Glu Ser Gly Arg Tyr Asp Tyr Tyr Pro Leu Tyr Glu Ile Gln Ala
        1625                1630                1635

Arg Ser Val Gln Lys Gln Asn Leu Ile Asn His Ile Ile Ala Phe
        1640                1645                1650

Glu Asn Tyr Pro Val Asp Glu Gln Met Glu Gln Ala Gly Asp Gln
        1655                1660                1665

Gln His Gly Asp Leu Thr Ile Ala Asp Val Gln Met Glu Glu Gln
        1670                1675                1680

Thr Asn Tyr Asn Phe Asn Val Thr Val Val Pro Gly Val Glu Ile
        1685                1690                1695

Glu Ile Arg Phe Asp Phe Asn Ala Glu Val Phe Asp Lys Asp Ser
        1700                1705                1710

Ile Glu Arg Leu Lys Gly His Leu Val His Leu Leu Glu Gln Val
        1715                1720                1725

Thr Asp Asn Pro Glu Ile Thr Val Gly Glu Leu Glu Leu Val Thr
        1730                1735                1740

Glu Gly Glu Lys Ala Asp Leu Leu Gly Arg Phe Asn Asp Thr Thr
        1745                1750                1755
```

-continued

```
Thr Glu Phe Pro Arg Gly Lys Thr Leu Val Gln Leu Phe Glu Glu
    1760                1765                1770

Gln Ala Glu Leu Tyr Pro Asp Asn Val Ala Ala Val Met Asn Glu
    1775                1780                1785

Arg Gln Leu Thr Tyr Arg Glu Leu Asn Glu Arg Ser Asn Arg Leu
    1790                1795                1800

Ala Arg Lys Leu Arg Glu Thr Gly Val Gly Ala Asp Gln Leu Val
    1805                1810                1815

Ala Ile Leu Ala Glu Arg Ser Leu Asp Met Val Val Gly Ile Leu
    1820                1825                1830

Ala Ile Leu Lys Ala Gly Gly Ala Tyr Val Pro Val Asp Pro Asp
    1835                1840                1845

Tyr Pro Glu Glu Arg Ile Arg Phe Met Ile Glu Asp Ser Gly Ala
    1850                1855                1860

Pro Leu Leu Leu Ile Gln Lys His Leu His Glu Lys Thr Asp Phe
    1865                1870                1875

Ala Gly Thr Arg Leu Glu Leu Asp Asp Phe Val Trp Gly Asp Arg
    1880                1885                1890

Gly Ala Asp Ser Ala Asp Ala Leu Asp Ala Ser Asn Leu Glu Pro
    1895                1900                1905

Ile Ser Gly Pro Gly Asn Leu Ala Tyr Val Ile Tyr Thr Ser Gly
    1910                1915                1920

Thr Thr Gly Arg Pro Lys Gly Thr Leu Ile Glu His Lys Asn Val
    1925                1930                1935

Val Arg Leu Leu Phe Asn Asp Lys Asn Leu Phe Asp Phe Gly Pro
    1940                1945                1950

Ser Asp Thr Trp Thr Leu Phe His Ser Phe Cys Phe Asp Phe Ser
    1955                1960                1965

Val Trp Glu Met Tyr Gly Ala Leu Leu Tyr Gly Gly Lys Leu Val
    1970                1975                1980

Ile Val Pro Ser Leu Thr Ala Lys Asn Pro Ala Asp Phe Leu Ala
    1985                1990                1995

Leu Leu Gly Arg Glu Gln Val Thr Ile Leu Asn Gln Thr Pro Thr
    2000                2005                2010

Tyr Phe Tyr Gln Leu Leu Arg Glu Val Leu Ala Asp His Pro Tyr
    2015                2020                2025

Asp Leu Arg Ile Arg Asn Val Ile Phe Gly Gly Glu Ala Leu Ser
    2030                2035                2040

Pro Leu Leu Leu Lys Gly Phe Lys Thr Lys Tyr Pro Glu Thr Lys
    2045                2050                2055

Leu Ile Asn Met Tyr Gly Ile Thr Glu Thr Thr Val His Val Thr
    2060                2065                2070

Tyr Lys Glu Ile Thr Trp Val Glu Met Glu Ala Ala Lys Ser Asn
    2075                2080                2085

Ile Gly Lys Pro Ile Pro Thr Leu Arg Val Tyr Val Leu Asp Glu
    2090                2095                2100

Asn Arg Arg Pro Val Pro Ile Gly Val Ala Gly Glu Met Tyr Val
    2105                2110                2115

Ala Gly Glu Gly Leu Ala Arg Gly Tyr Leu Asn Arg Pro Asp Leu
    2120                2125                2130

Thr Ala Glu Lys Phe Val Asp Ser Pro Phe Ala Glu Gly Glu Lys
    2135                2140                2145
```

-continued

```
Leu Tyr Arg Ser Gly Asp Leu Ala Ala Trp Leu Pro Asp Gly Asn
2150                2155                2160

Ile Glu Tyr Leu Gly Arg Ile Asp His Gln Val Lys Ile Arg Gly
2165                2170                2175

Tyr Arg Ile Glu Leu Asp Glu Ile Glu Thr Gln Leu Leu Asn Val
2180                2185                2190

Arg Gly Val Glu Glu Ala Val Val Leu Ala Arg Gln Asp Gly Gly
2195                2200                2205

Gly Glu Lys Ala Leu Val Ala Tyr Phe Val Ala Asp Arg Thr Leu
2210                2215                2220

Thr Val Ser Glu Met Arg Thr Ser Leu Ala Gln Gly Met Pro Gly
2225                2230                2235

Tyr Met Ile Pro Ser Tyr Phe Val Gln Leu Glu Arg Met Pro Leu
2240                2245                2250

Thr Thr Asn Gly Lys Val Asp Arg Lys Ala Leu Pro Glu Pro Gln
2255                2260                2265

Gly Gly Ile Gln Thr Gly Val Glu Tyr Val Ala Pro Arg Asn Trp
2270                2275                2280

Thr Glu Ser Gln Leu Val Lys Ile Trp Glu Glu Val Leu Gly Tyr
2285                2290                2295

Ser Gly Ile Gly Val Leu Asp Asn Phe Phe Glu Leu Gly Gly His
2300                2305                2310

Ser Leu Arg Ala Thr Asn Leu Val Ser Lys Ile Gln Lys Glu Met
2315                2320                2325

Asn Val Glu Leu Pro Leu Arg Asp Val Phe Arg Tyr Ser Thr Ile
2330                2335                2340

Glu Glu Met Ala Leu Ala Ile Ser Arg Ile Gly Glu Gln Ser Phe
2345                2350                2355

Ser Ser Ile Pro Leu Ala Gly Ala Arg Ala Tyr Tyr Pro Leu Ser
2360                2365                2370

Ser Ala Gln Lys Arg Leu Phe Ile Leu Asn Gln Leu Glu Gly Ala
2375                2380                2385

Asp Gln Ser Tyr Asn Met Pro Gly Val Leu Leu Leu Glu Gly Ser
2390                2395                2400

Ile Asp Arg Ser Leu Leu Glu Lys Ala Phe Arg Gly Leu Ile Ala
2405                2410                2415

Arg His Glu Thr Leu Arg Thr Gly Phe Glu Ile Val Gln Gly Glu
2420                2425                2430

Ala Ile Gln Arg Ile Tyr Glu Ser Val Asp Phe Ala Val Glu Tyr
2435                2440                2445

Arg His Ala Ser Glu Glu Ala Pro Glu Val Val Gln Ala Phe
2450                2455                2460

Ile Arg Pro Phe Asp Leu Ala Lys Pro Pro Leu Leu Arg Ala Glu
2465                2470                2475

Leu Val Glu Leu Ala Ala Glu Arg Tyr Leu Leu Met Phe Asp Met
2480                2485                2490

His His Ile Val Ser Asp Gly Val Ser Met Asp Val Leu Val Glu
2495                2500                2505

Glu Leu Val Arg Leu Tyr Gly Gly Glu Ser Leu Glu Pro Leu Arg
2510                2515                2520

Ile Gln Tyr Lys Asp Tyr Ala Val Trp Gln Gln Ser Asp Glu Gln
2525                2530                2535

Lys Val Gln Leu Lys Arg Glu Glu Ala Tyr Trp Leu Asp Arg Tyr
```

-continued

```
                    2540                2545                2550

Arg Gly Glu Leu Pro Val Leu Glu Met Pro Thr Asp Tyr Pro Arg
    2555                2560                2565

Pro Ala Val Gln Ser Phe Glu Gly Gln Thr Leu Thr Ser Phe Val
    2570                2575                2580

Asp Glu Ala Thr Asn Glu Gly Leu Lys Gln Leu Ala Ala Gln Arg
    2585                2590                2595

Gly Thr Thr Leu Tyr Met Val Leu Leu Ala Ala Tyr Thr Val Leu
    2600                2605                2610

Leu His Lys Tyr Thr Gly Gln Asp Asp Leu Ile Val Gly Thr Ser
    2615                2620                2625

Ile Ala Gly Arg Thr His Gly Asp Thr Gln Pro Leu Ile Gly Met
    2630                2635                2640

Phe Val Asn Thr Leu Ala Leu Arg Asn Tyr Pro Ala Ser Lys Lys
    2645                2650                2655

Thr Phe Leu Ser Tyr Leu Glu Glu Val Lys Glu Thr Thr Leu Gly
    2660                2665                2670

Ala Tyr Glu His Gln Asn Tyr Pro Phe Glu Glu Leu Val Asp Lys
    2675                2680                2685

Val Gln Val Ser Arg Asp Leu Ser Arg Asn Pro Leu Phe Asp Thr
    2690                2695                2700

Met Phe Ser Leu Gln Asn Leu Glu Asp Lys Glu Phe Glu Leu Glu
    2705                2710                2715

Gly Leu Lys Leu Ser Ser Tyr Pro Ser Glu Tyr Gly Thr Ala Lys
    2720                2725                2730

Phe Asp Leu Ser Val Asp Val Thr Glu Glu Asn Gly Gly Leu Glu
    2735                2740                2745

Cys Ser Phe Glu Phe Ala Thr Ala Leu Tyr Lys Glu Ser Thr Ile
    2750                2755                2760

Arg Arg Leu Ser Thr His Phe Gly His Leu Leu Ala Ala Ile Ala
    2765                2770                2775

Ser Arg Pro Asp Ala Lys Ile Ala Glu Leu Asn Leu Leu Thr Ala
    2780                2785                2790

Glu Glu Lys Glu Gln Ile Leu Gly Ala Phe Asn Pro Ala Gln Leu
    2795                2800                2805

Glu Ala Ala Pro Ala Ala Ala Phe His Arg Leu Phe Glu Glu Gln
    2810                2815                2820

Val Glu Arg Thr Pro Glu Glu Ala Ala Val Val Tyr Glu Asn Glu
    2825                2830                2835

Arg Leu Thr Tyr Ala Glu Leu Asn Glu Arg Ala Asn Arg Leu Ala
    2840                2845                2850

Ala Thr Leu Arg Ala Ser Gly Ile Gly Arg Glu Thr Ile Val Gly
    2855                2860                2865

Ile Leu Ala Glu Arg Ser Val Asp Leu Leu Val Ala Val Leu Ala
    2870                2875                2880

Val Trp Lys Ala Gly Gly Ala Tyr Val Pro Leu Asp Pro Asp Tyr
    2885                2890                2895

Pro Ala Asp Arg Val Arg Phe Met Leu Glu Asp Ser Gly Ala Lys
    2900                2905                2910

Val Leu Leu Thr Gln Thr Ala Leu Arg Glu Arg Ala Glu Ala Trp
    2915                2920                2925

Leu Gly Glu Glu Glu Leu Ala Leu Ala Ala Val Leu Tyr Leu Asp
    2930                2935                2940
```

-continued

```
Asp Glu Ala Ser Tyr Asn Glu Arg Ala Asn Ala Pro Val Gly
    2945                2950                2955

Ser Gly Met Val Ser Gly Lys Leu Thr Asp Ala Val Asp Asp Gly
    2960                2965                2970

Asp Glu Ser His Gln Asn Val Asp Thr Asp Gly Phe His Glu Ala
    2975                2980                2985

Arg Pro Glu Asp Leu Ala Tyr Val Ile Tyr Thr Ser Gly Thr Thr
    2990                2995                3000

Gly Lys Pro Lys Gly Val Met Ile Glu His Arg Ser Leu Val Asn
    3005                3010                3015

Thr Ala Ala Gly Tyr Arg Arg Glu Tyr Arg Leu Asp Gln Phe Pro
    3020                3025                3030

Val Arg Leu Leu Gln Leu Ala Ser Phe Ser Phe Asp Val Phe Val
    3035                3040                3045

Gly Asp Ile Ala Arg Thr Leu Tyr Asn Gly Gly Thr Met Val Ile
    3050                3055                3060

Val Pro Lys Asp Asp Arg Ile Asp Pro Ser Arg Leu His His Trp
    3065                3070                3075

Met Glu Arg Glu Arg Val Thr Ile Phe Glu Ser Thr Pro Ala Leu
    3080                3085                3090

Ile Val Pro Phe Leu Glu Tyr Val His Glu Gln Arg Leu Asp Met
    3095                3100                3105

Ser Trp Met Glu Leu Leu Ile Thr Ser Ser Asp Ser Cys Ser Val
    3110                3115                3120

Ala Asp Tyr Arg Thr Leu Gln Glu Arg Phe Gly Ser Leu Phe Arg
    3125                3130                3135

Ile Ile Asn Ala Tyr Gly Val Thr Glu Ala Ala Ile Asp Ser Ser
    3140                3145                3150

Phe Tyr Asp Glu Glu Leu Thr Lys Leu Pro Gln Thr Gly His Val
    3155                3160                3165

Pro Ile Gly Lys Ala Trp Leu Asn Ala Lys Phe Tyr Ile Val Asp
    3170                3175                3180

Ala His Leu Asn Pro Val Pro Val Gly Val Leu Gly Glu Leu Val
    3185                3190                3195

Ile Gly Gly Val Gly Val Ala Arg Gly Tyr Leu Asn Arg Pro Glu
    3200                3205                3210

Leu Thr Glu Glu Lys Phe Val Asp Ser Pro Phe Ala Ala Gly Glu
    3215                3220                3225

Arg Leu Tyr Arg Thr Gly Asp Leu Ala Arg Trp Met Glu Asp Gly
    3230                3235                3240

Asn Val Asp Phe Ile Gly Arg Ile Asp Asn Gln Ala Lys Ile Arg
    3245                3250                3255

Gly Tyr Arg Ile Glu Thr Gly Glu Ile Glu Ser Gln Leu Leu Arg
    3260                3265                3270

Val Glu Gly Val Arg Glu Ala Val Val Leu Val Arg Ser Asp Ala
    3275                3280                3285

Asn Gly Gln Lys Ala Leu Cys Ala Tyr Tyr Thr Pro Asp Thr Gly
    3290                3295                3300

Ala Glu Leu Ala Val Asn Asp Leu Arg Gly Ala Leu Ala Gln Glu
    3305                3310                3315

Leu Pro Gly Tyr Met Ile Pro Ser Tyr Phe Val Glu Leu Glu Arg
    3320                3325                3330
```

-continued

```
Leu Pro Leu Thr Pro Asn Gly Lys Ile Asp Arg Lys Ala Leu Pro
    3335            3340                3345
Ala Pro Glu Arg Glu Ala Gly Ser Gly Thr Glu Tyr Val Ala Pro
    3350            3355                3360
Arg Asn Glu Leu Glu Thr Lys Leu Thr Ala Ile Trp Gln Glu Val
    3365            3370                3375
Leu Gly Leu Ala Lys Glu Ile Gly Val His Asp Asn Phe Phe Asp
    3380            3385                3390
Ile Gly Gly His Ser Leu Arg Ala Thr Thr Leu Val Ser Lys Ile
    3395            3400                3405
His Lys Glu Leu Asn Val Asp Leu Pro Leu Arg Asp Val Phe Arg
    3410            3415                3420
His Ser Thr Ile Glu Ser Met Ala Ala Ile Ser Arg Leu Asp
    3425            3430                3435
Glu Gln Thr Phe Val Ala Ile Pro Val Ala Asp Arg Glu Val
    3440            3445                3450
Tyr Pro Gln Ser Phe Ala Gln Lys Arg Leu Phe Ile Leu Asn Gln
    3455            3460                3465
Leu Glu Gly Ala Glu Leu Ser Tyr Asn Met Pro Glu Ala Met Leu
    3470            3475                3480
Leu Glu Gly Ala Leu Asp Arg Thr Arg Phe Glu Glu Ala Phe Arg
    3485            3490                3495
Lys Leu Val Ala Arg His Glu Thr Leu Arg Thr Gly Phe Glu Met
    3500            3505                3510
Val Asp Gly Glu Ala Ser Gln Arg Ile Tyr Gln Asp Val Asn Phe
    3515            3520                3525
Ala Val Glu Phe Tyr Arg Val Asp Glu Gln Glu Ala Glu Glu Thr
    3530            3535                3540
Val His Arg Phe Val Arg Pro Phe Asp Leu Ala Lys Pro Pro Leu
    3545            3550                3555
Leu Arg Val Gly Leu Val Glu Leu Ala Pro Glu Arg His Ile Leu
    3560            3565                3570
Met Tyr Asp Met His His Ile Ile Ser Asp Gly Val Ser Met Glu
    3575            3580                3585
Ile Phe Val Glu Glu Phe Val Arg Leu Tyr Gly Gly Glu Gln Leu
    3590            3595                3600
Glu Pro Leu Arg Ile Gln Tyr Lys Asp Tyr Thr Val Trp Gln His
    3605            3610                3615
Ser Gln Glu Gln Lys Glu Arg Leu Gln Arg Gln Glu Ala Tyr Trp
    3620            3625                3630
Leu Asp Met Phe Gln Gly Glu Leu Pro Val Leu Glu Met Pro Thr
    3635            3640                3645
Asp Tyr Pro Arg Pro Ala Val Gln Ser Tyr Glu Gly Gln Thr Leu
    3650            3655                3660
Glu Phe Phe Phe Asp Ala Ser Lys Thr Asp Gly Leu Lys Gln Leu
    3665            3670                3675
Ala Ser Glu Thr Gly Thr Thr Leu Phe Met Val Leu Leu Ala Ala
    3680            3685                3690
Tyr Asn Val Leu Leu His Lys Tyr Ser Gly Gln Glu Asp Val Ile
    3695            3700                3705
Val Gly Thr Pro Ile Ala Gly Arg Asn His Gly Asp Val Gln Pro
    3710            3715                3720
Leu Ile Gly Ile Phe Leu Asn Thr Leu Ala Ile Arg Ser Tyr Pro
```

-continued

```
                 3725                3730                3735

Ala  Ser  Glu  Lys  Thr  Phe  Leu  Ser  Tyr  Leu  Asn  Glu  Val  Lys  Glu
     3740                3745                3750

Thr  Thr  Leu  His  Ala  Phe  Glu  His  Gln  Asn  Tyr  Pro  Phe  Glu  Glu
     3755                3760                3765

Leu  Val  Asp  Lys  Val  Gln  Val  Thr  Arg  Asp  Leu  Ser  Arg  Asn  Pro
     3770                3775                3780

Leu  Phe  Asp  Thr  Leu  Phe  Thr  Met  Gln  Asn  Thr  Glu  Asn  Glu  Glu
     3785                3790                3795

Phe  Glu  Leu  Glu  Gly  Leu  Arg  Leu  Ile  Pro  Tyr  Pro  Ser  Ala  Leu
     3800                3805                3810

Asp  Thr  Ala  Lys  Phe  Asp  Ile  Ser  Leu  Asp  Val  Gly  Glu  Glu  Asn
     3815                3820                3825

Gly  Gly  Leu  Asp  Tyr  Ser  Phe  Glu  Tyr  Ala  Thr  Ala  Leu  Tyr  Lys
     3830                3835                3840

Arg  Glu  Thr  Ile  Glu  Arg  Leu  Ala  Lys  His  Tyr  Glu  Gln  Leu  Leu
     3845                3850                3855

Val  Thr  Ile  Val  Ser  Arg  Pro  Asp  Ala  Lys  Ile  Ala  Glu  Leu  Asn
     3860                3865                3870

Leu  Leu  Thr  Ala  Glu  Glu  Lys  Gly  Gln  Ile  Leu  Gly  Ala  Phe  His
     3875                3880                3885

Pro  Ala  Gln  Leu  Glu  Ala  Ala  Pro  Ala  Ala  Ala  Phe  His  Arg  Leu
     3890                3895                3900

Phe  Glu  Glu  Gln  Ala  Glu  Arg  Thr  Pro  Glu  Ala  Val  Ala  Val  Val
     3905                3910                3915

Tyr  Glu  Asn  Asp  Arg  Leu  Thr  Tyr  Ala  Glu  Leu  Asn  Glu  Arg  Ala
     3920                3925                3930

Asn  Arg  Leu  Ala  Ala  Thr  Leu  Arg  Ala  Ser  Gly  Ile  Gly  Arg  Glu
     3935                3940                3945

Thr  Ile  Val  Gly  Ile  Leu  Ala  Glu  Arg  Ser  Val  Asp  Leu  Leu  Val
     3950                3955                3960

Ala  Val  Leu  Ala  Val  Trp  Lys  Ala  Gly  Gly  Ala  Tyr  Val  Pro  Leu
     3965                3970                3975

Asp  Pro  Asp  Tyr  Pro  Ala  Glu  Arg  Val  Arg  Phe  Met  Leu  Glu  Asp
     3980                3985                3990

Ser  Gly  Ala  Lys  Val  Leu  Leu  Thr  Gln  Thr  Pro  Leu  Arg  Glu  Arg
     3995                4000                4005

Ala  Lys  Ala  Trp  Leu  Gly  Glu  Glu  Glu  Leu  Ala  Leu  Ala  Ala  Val
     4010                4015                4020

Leu  Tyr  Leu  Asp  Asp  Glu  Ala  Ser  Tyr  Ser  Glu  Glu  Arg  Ala  Asn
     4025                4030                4035

Ala  Asp  Ser  Phe  His  Glu  Ala  Arg  Pro  Glu  Asp  Leu  Ala  Tyr  Val
     4040                4045                4050

Ile  Tyr  Thr  Ser  Gly  Thr  Thr  Gly  Lys  Pro  Lys  Gly  Val  Met  Ile
     4055                4060                4065

Glu  His  Arg  Ser  Leu  Val  Asn  Thr  Ala  Ala  Ser  Tyr  Arg  Arg  Glu
     4070                4075                4080

Tyr  Arg  Leu  Asp  Gln  Phe  Pro  Val  Arg  Leu  Leu  Gln  Leu  Ala  Ser
     4085                4090                4095

Phe  Ser  Phe  Asp  Val  Phe  Val  Gly  Asp  Ile  Ala  Arg  Thr  Leu  Tyr
     4100                4105                4110

Asn  Gly  Gly  Thr  Met  Val  Ile  Val  Pro  Lys  Asp  Asp  Arg  Ile  Asp
     4115                4120                4125
```

-continued

```
Pro Ser Arg Leu His Tyr Trp Met Glu Arg Glu Gln Val Thr Ile
    4130            4135                4140
Phe Glu Ser Thr Pro Ala Leu Ile Val Pro Phe Met Glu Tyr Val
    4145            4150                4155
His Glu Gln Gly Leu Asp Met Ser Trp Met Glu Leu Leu Ile Thr
    4160            4165                4170
Ser Ser Asp Ser Cys Ser Val Ala Asp Tyr Arg Thr Leu Gln Glu
    4175            4180                4185
Arg Phe Gly Ser Leu Phe Arg Ile Ile Asn Ala Tyr Gly Val Thr
    4190            4195                4200
Glu Ala Ala Ile Asp Ser Ser Phe Tyr Asp Glu Glu Leu Ala Lys
    4205            4210                4215
Leu Pro Gln Thr Gly His Val Pro Ile Gly Lys Ala Trp Leu Asn
    4220            4225                4230
Ala Lys Phe Tyr Ile Val Asp Ala His Leu Asn Pro Val Pro Val
    4235            4240                4245
Gly Val Leu Gly Glu Leu Val Ile Gly Gly Val Gly Val Ala Arg
    4250            4255                4260
Gly Tyr Leu Asn Arg Pro Glu Leu Thr Gly Glu Lys Phe Val Asp
    4265            4270                4275
Ser Pro Phe Ala Ala Gly Glu Arg Leu Tyr Arg Thr Gly Asp Leu
    4280            4285                4290
Ala Arg Trp Met Glu Asp Gly Asn Val Asp Phe Ile Gly Arg Ile
    4295            4300                4305
Asp Asn Gln Ala Lys Ile Arg Gly Tyr Arg Ile Glu Thr Gly Glu
    4310            4315                4320
Ile Glu Ser Gln Leu Leu Gln Val Glu Gly Val Arg Glu Ala Val
    4325            4330                4335
Val Leu Val Arg Ser Asp Ala Asn Gly Gln Lys Ala Leu Cys Ala
    4340            4345                4350
Tyr Tyr Thr Pro Asp Thr Gly Ala Glu Leu Ala Val Asn Asp Leu
    4355            4360                4365
Arg Gly Ala Leu Ala Gln Glu Leu Pro Gly Tyr Met Ile Pro Ser
    4370            4375                4380
Tyr Phe Val Glu Met Glu Arg Leu Pro Leu Thr Pro Asn Gly Lys
    4385            4390                4395
Ile Asp Arg Lys Ala Leu Pro Ala Pro Glu Gly Glu Ala Gly Ser
    4400            4405                4410
Gly Thr Glu Tyr Val Ala Pro Arg Asn Glu Leu Glu Thr Lys Leu
    4415            4420                4425
Thr Ala Ile Trp Gln Glu Val Leu Gly Leu Ala Lys Glu Ile Gly
    4430            4435                4440
Val His Asp Asn Phe Phe Asp Ile Gly Gly His Ser Leu Arg Ala
    4445            4450                4455
Thr Thr Leu Ala Gly Lys Val Phe Lys Glu Leu Asn Val Asn Leu
    4460            4465                4470
Pro Leu Arg Asp Val Phe His Ser Thr Ile Ala Ala Met Ala
    4475            4480                4485
Glu Ala Ile Ala Arg Met Glu Arg Arg Glu His Glu Ala Ile Pro
    4490            4495                4500
Gln Ala Glu Glu Arg Glu Tyr Tyr Pro Leu Ser Ser Ala Gln Lys
    4505            4510                4515
```

-continued

```
Arg Leu Phe Ile Gln His Thr Leu Asp Gly Ala Asp Gln Leu Tyr
4520                4525                4530

Asn Met Pro Glu Leu Val Gln Val Glu Gly Glu Phe Asp Leu Glu
4535                4540                4545

Arg Leu Glu Ala Ala Leu Arg Lys Leu Ile Thr Arg His Glu Ser
4550                4555                4560

Leu Arg Thr Gly Phe Glu Ile Val Lys Gly Glu Ala Val Gln Arg
4565                4570                4575

Ile Tyr Pro Gln Val Asp Phe Ala Ile Glu His Tyr Gln Ala Asp
4580                4585                4590

Lys Glu Asp Ala Ala Gln Ile Glu Gln Ile Val Arg Ser Phe Val
4595                4600                4605

Arg Pro Phe Asp Leu Gly Lys Pro Pro Leu Leu Arg Ala Gly Val
4610                4615                4620

Ile Glu Leu Glu Pro Asn Leu His Ile Leu Leu Phe Asp Met His
4625                4630                4635

His Met Val Ser Asp Gly Val Ser Met Ala Ile Val Ile Asp Glu
4640                4645                4650

Phe Ser Ser Phe Tyr Ala Gly Glu Glu Leu Pro Pro Leu Arg Ile
4655                4660                4665

Gln Tyr Lys Asp Tyr Ala Val Trp Gln Gln Ser Lys Ala His Arg
4670                4675                4680

Glu Arg Ile Gly Arg Gln Glu Ala Tyr Trp Leu Gln Thr Phe Glu
4685                4690                4695

Gly Glu Leu Pro Thr Ala Asp Leu Pro Met Asp Tyr Glu Arg Ser
4700                4705                4710

Ala Ala Arg Ser Tyr Glu Gly Ala His Leu Glu Phe Asp Val Glu
4715                4720                4725

Ala Ser Leu Ser Ala Gln Leu Arg Glu Leu Ala Ala Glu Arg Glu
4730                4735                4740

Ser Thr Leu Phe Met Val Leu Leu Ala Ala Tyr Thr Val Leu Leu
4745                4750                4755

Ser Lys Tyr Ser Gly Gln Glu Asp Leu Val Val Gly Thr Pro Val
4760                4765                4770

Ala Gly Arg Thr Asn Ala Asp Leu Glu Pro Ile Ile Gly Met Phe
4775                4780                4785

Val Asn Thr Leu Ala Ile Arg Asn Arg Pro Ser Gly Asp Lys Thr
4790                4795                4800

Phe Leu Ser Tyr Leu Glu Glu Val Lys Glu Thr Ala Leu Gly Ala
4805                4810                4815

Phe Glu Asn Gln Asp Tyr Pro Phe Glu Glu Leu Val Glu Arg Leu
4820                4825                4830

Asn Val Lys Arg Glu Pro Gly Arg Phe Pro Leu Phe Asp Ala Val
4835                4840                4845

Phe Asp Leu Gln Asn Ile Glu Glu Arg Asp Ala Glu Leu Glu Gly
4850                4855                4860

Val Ser Leu Lys Thr Tyr Glu Leu Asp His Leu Glu Glu Ala Lys
4865                4870                4875

Phe Asp Leu Thr Leu Phe Met Tyr Glu Asn Asn Gly Ala Leu Ser
4880                4885                4890

Gly Gly Phe Phe Tyr Ala Thr Lys Leu Phe Lys Glu Ala Met Ile
4895                4900                4905

Arg Thr Leu Thr Glu Asp Tyr Leu Arg Val Leu Ser Gln Ile Ala
```

-continued

```
              4910                4915                4920
Lys Asn Pro Gln Leu Glu Leu Ser Arg Ile Glu Cys His Lys Pro
          4925                4930                4935

Ala Ala Gly Ala Lys Ser Ala Val Asp Thr Ile Glu Phe Ala Phe
          4940                4945                4950

<210> SEQ ID NO 5
<211> LENGTH: 1102
<212> TYPE: PRT
<213> ORGANISM: Polymyxa betae

<400> SEQUENCE: 5

Met Lys Ser Leu Phe Glu Lys Glu Gln Tyr Trp Ser Gly Lys Phe
1               5                  10                  15

Asp Ala Asp Asp Ser Leu Ser Phe Leu Pro Tyr Ser Gln Ser Ser Lys
             20                  25                  30

Leu Ser Ala His Gly Glu Ala Ala Glu Pro Gly Leu Leu His Arg
         35                  40                  45

Thr Leu Pro Ser Gln Leu Ser Glu Arg Ile Ile Ser Leu Ala Asn Gly
     50                  55                  60

Ser Asp Leu Ala Leu Tyr Met Ile Val Leu Ala Gly Val Lys Ser Leu
65                  70                  75                  80

Leu Phe Lys Tyr Thr Gly Arg Asp Gln Val Leu Val Gly Met Pro Ser
                 85                  90                  95

Tyr Ser Ala Asp Pro Asp Gly Thr Pro Pro His Asp Ile Leu Val
             100                 105                 110

Ile Lys Thr Ser Val Ser Arg Gln Thr Thr Leu Lys Thr Leu Leu Gly
         115                 120                 125

Gly Ile Lys Ala Ser Ile Gly Glu Ala Leu Glu His Gln His Leu Pro
     130                 135                 140

Phe Arg Lys Met Val Glu Pro Leu His Leu Asp Tyr Thr Gly Asp Gly
145                 150                 155                 160

Leu Pro Val Val Asn Thr Val Val Ser Phe Ala Pro Ile His Pro Glu
                 165                 170                 175

Pro Gln Gly Asn Arg Val Ala Ala Asp Thr Val Phe Arg Phe Asp Arg
             180                 185                 190

Gln Asn His Ser Ile Glu Leu Glu Ile Ser Phe Asp Gly Gln Arg Tyr
         195                 200                 205

Glu Arg Ala Phe Val Glu Gln Ala Ala Asp His Leu Val Arg Leu Leu
     210                 215                 220

Ser Val Leu Leu Phe Gln Pro Asp Leu Lys Leu Gly Gln Ala Asp Val
225                 230                 235                 240

Leu Ser Pro Asp Glu Arg Glu Thr Leu Leu Lys Arg Phe Asn Asp Thr
                 245                 250                 255

Glu Thr Glu Phe Glu Arg Gly Lys Thr Ile Tyr Gly Leu Phe Glu Glu
             260                 265                 270

Gln Ala Glu Leu Tyr Pro Asp Asn Val Ala Ala Val Met Asn Glu Arg
         275                 280                 285

Gln Leu Thr Tyr Arg Glu Leu Asn Glu Arg Ser Asn Arg Leu Ala Arg
     290                 295                 300

Lys Leu Arg Glu Ala Gly Val Glu Ala Asp Gln Leu Val Ala Ile Leu
305                 310                 315                 320

Ala Glu Arg Ser Leu Asp Met Val Val Gly Ile Leu Ala Ile Leu Lys
                 325                 330                 335
```

```
Ala Gly Gly Ala Tyr Val Pro Val Asp Pro Asp Tyr Pro Glu Glu Arg
            340                 345                 350

Ile Arg Phe Met Ile Glu Asp Ser Gly Ala Pro Leu Leu Leu Ile Gln
        355                 360                 365

Lys His Leu His Glu Lys Thr Asp Phe Ala Gly Thr Arg Leu Glu Leu
    370                 375                 380

Asp Asp Phe Val Trp Gly Asp Arg Gly Ala Asn Ser Ala Glu Ala Leu
385                 390                 395                 400

Asp Ala Ser Asn Leu Glu Pro Ile Ser Gly Pro Gly Asn Leu Ala Tyr
                405                 410                 415

Val Ile Tyr Thr Ser Gly Thr Thr Gly Arg Pro Lys Gly Thr Leu Ile
            420                 425                 430

Glu His Lys Asn Val Val Arg Leu Leu Phe Asn Asp Lys Asn Leu Phe
        435                 440                 445

Asp Phe Gly Pro Ser Asp Thr Trp Thr Leu Phe His Ser Phe Cys Phe
    450                 455                 460

Asp Phe Ser Val Trp Glu Met Tyr Gly Ala Leu Leu Tyr Gly Gly Lys
465                 470                 475                 480

Leu Val Ile Val Pro Pro Leu Thr Ala Lys Asn Pro Ala Asp Phe Leu
                485                 490                 495

Ala Leu Leu Gly Arg Glu Gln Val Thr Ile Leu Asn Gln Thr Pro Thr
            500                 505                 510

Tyr Phe Tyr Gln Leu Leu Arg Lys Val Leu Ala Asp His Pro Tyr Asp
        515                 520                 525

Leu Arg Ile Arg Asn Val Ile Phe Gly Gly Glu Ala Leu Ser Pro Leu
    530                 535                 540

Leu Leu Lys Gly Phe Lys Thr Lys Tyr Pro Glu Thr Lys Leu Ile Asn
545                 550                 555                 560

Met Tyr Gly Ile Thr Glu Thr Thr Val His Val Thr Tyr Lys Glu Ile
                565                 570                 575

Thr Trp Val Glu Met Glu Ala Ala Lys Ser Asn Ile Gly Lys Pro Ile
            580                 585                 590

Pro Thr Leu Arg Val Tyr Val Leu Asp Glu Asn Arg Arg Leu Val Pro
        595                 600                 605

Ile Gly Val Ala Gly Glu Met Tyr Val Ala Gly Glu Gly Leu Ala Arg
    610                 615                 620

Gly Tyr Leu Asn Arg Pro Asp Leu Thr Ala Glu Lys Phe Val Asp Ser
625                 630                 635                 640

Pro Phe Ala Glu Gly Glu Arg Leu Tyr Arg Ser Gly Asp Leu Ala Ala
                645                 650                 655

Trp Leu Pro Asp Gly Asn Ile Glu Tyr Leu Gly Arg Ile Asp His Gln
            660                 665                 670

Val Lys Ile Arg Gly Tyr Arg Ile Glu Leu Asp Glu Ile Glu Thr Gln
        675                 680                 685

Leu Leu Asn Ala Arg Gly Val Glu Glu Ala Val Val Leu Ala Arg Asp
    690                 695                 700

Asp Ala His Gly His Lys Gln Leu Val Ala Tyr Val Ala Glu Thr
705                 710                 715                 720

Arg Leu Ala Ala Asn Glu Leu Lys Glu Leu Ala Lys Gln Leu Pro
                725                 730                 735

Gly Tyr Met Ile Pro Ser His Leu Val Gln Leu Ser Arg Met Pro Leu
            740                 745                 750

Thr Pro Asn Gly Lys Ile Asp Arg Lys Ala Leu Pro Ala Pro Glu Glu
```

755                 760                 765
Ala Ala Ala Gly Gly Ala Glu Tyr Val Ala Pro Arg Thr Leu Leu Glu
            770                 775                 780

Met Lys Ile Val Arg Val Trp Gln Asp Thr Leu Gly Val Pro Gln Val
785                 790                 795                 800

Gly Val Lys Asp Asn Phe Phe Glu Leu Gly Asn Ser Leu Ser Leu
                805                 810                 815

Met Arg Leu Val Gln Ala Val Tyr Asp Glu Thr Gly Ile Glu Ile Pro
            820                 825                 830

Leu Asn Arg Gln Phe His Asn Val Thr Val Glu Ala Met Ala Phe Gly
            835                 840                 845

Glu Gly Asp Leu Gly Leu Asp Lys Gly Gly Asp Ser Phe Ile Lys Leu
        850                 855                 860

Asn Lys Ala Gly Asp Leu Asn Val Phe Cys Phe Pro Pro Gly Ser Gly
865                 870                 875                 880

Phe Gly Ile Gly Tyr Arg Glu Leu Ala Ser Arg Leu Asp Gly Arg Phe
                885                 890                 895

Val Leu Tyr Gly Ile Asp Phe Ile Asp Asp Ala Ala Asp Tyr Glu Ala
            900                 905                 910

Met Leu Asn Arg Tyr Val Asp Glu Ile Val Arg Ile Gln Pro Glu Gly
            915                 920                 925

Pro Tyr Val Leu Leu Gly Tyr Cys Phe Gly Gly Asn Leu Met Phe Glu
        930                 935                 940

Val Ala Lys Thr Met Glu Lys Arg Glu Tyr Ser Val Thr Asp Val Leu
945                 950                 955                 960

Met Val Asp Ser Trp Ile Lys Asp Thr Leu Thr Pro Ser Glu Thr Ser
                965                 970                 975

Glu Lys Glu Leu Glu Glu Thr Leu Ala Asp Phe Asp Glu Glu Lys
            980                 985                 990

Glu Leu Met Ser Asn Pro Leu Val Arg Glu Arg Val His Arg Lys Val
            995                 1000                1005

Lys Ala Thr Leu Ala Tyr Glu Ala Gln Leu Met Asn Ser Gly Thr
        1010                1015                1020

Ile Pro Ala Arg Ile Tyr Glu Leu Ile Ala Lys Asp Ser Glu Ala
        1025                1030                1035

Phe Arg Leu Glu His Gln Leu Pro Ser Trp Arg Gly Ala Thr Thr
        1040                1045                1050

Gln Ala Tyr Ala Asp Tyr Arg Leu Glu Gly Ala His Glu Glu Leu
        1055                1060                1065

Leu Glu Leu Ala Arg Val Asp Glu Thr Ala Val Val Ile Arg Asp
        1070                1075                1080

Ile Leu Glu Gln Val Lys Arg Gln Ile Glu Ala Glu Ala Gly Val
        1085                1090                1095

Leu His Gly Ser
        1100

<210> SEQ ID NO 6
<211> LENGTH: 6312
<212> TYPE: PRT
<213> ORGANISM: Polymyxa betae

<400> SEQUENCE: 6

Met Arg Glu Asn Thr Lys Glu Gln Tyr Gly Leu Thr Gln Ala Gln Arg
1               5                   10                  15

-continued

```
Arg Ile Trp Phe Met Glu Ile Met Asn Pro Gly Thr Ser Ile Thr Met
             20                  25                  30

Leu Ser Ala Thr Tyr Gln Ile Thr Gly Glu Ile Asn Thr Gln Leu Leu
             35                  40                  45

Glu Gln Ala Ala Ala Glu Ile Val Lys Thr Tyr Asp Val Phe Arg Ile
 50                  55                  60

Arg Ile Ser Gly Asp Leu Gln Asn Pro Thr Gln Trp Phe Glu Pro
 65                  70                  75                  80

Glu Asn Val Gln Ala Arg Ile Ser Arg Leu Glu Ile Gly Thr Thr Glu
                 85                  90                  95

Gln Phe Tyr Ala Trp Val Lys Glu Val Ser Glu Lys Pro Ala Ser Val
                100                 105                 110

Phe Asp Glu His Leu His Gln Phe Thr Ile Ile His Phe Val Asn Gly
                115                 120                 125

Gln Val Trp Leu Asn Leu Thr Val Asn His Ile Ile Ala Asp Gly Leu
130                 135                 140

Ser Val Asn Ala Leu Leu His Ala Val Met Glu Lys Tyr Leu Glu Leu
145                 150                 155                 160

Arg Lys Gly Ile Ser Ser Tyr Gln Ala Pro Ser Tyr Leu Asp Tyr
                165                 170                 175

Ile Ser Ala Glu Arg Glu Tyr Glu Gln Ser Gln Arg Tyr Gln Lys Gly
                180                 185                 190

Lys Glu Tyr Trp Leu Thr Lys Tyr Asn Thr Leu Pro Glu Thr Thr Gly
                195                 200                 205

Ile Lys Ser Tyr Pro Pro Phe Ser Ile Gly Ser Glu Ser Asn Lys Leu
210                 215                 220

Ser Ile Thr Leu Asp Gly Ser Arg Tyr Glu Arg Ile Leu Thr Phe Ser
225                 230                 235                 240

Glu Gln Tyr Gln Val Ser Leu Tyr Thr Leu Phe Leu Ser Ala Met Tyr
                245                 250                 255

Ala Leu Leu Tyr Lys Leu Thr Asp Ser Ile Asp Val Pro Val Gly Thr
                260                 265                 270

Val Phe Ala Asn Arg Thr Ser Lys Lys Glu Lys Glu Thr Ile Gly Met
                275                 280                 285

Phe Val Ser Thr Val Ala Thr Arg Ile Arg Leu Asn Pro Asp Arg Asn
                290                 295                 300

Val Leu Ser Leu Ile Gln Thr Val Ser Lys Glu Asn Thr Ala Asp Leu
305                 310                 315                 320

Arg Tyr Gln Lys Tyr Pro Tyr Asn Gln Leu Ile Gln Asp Leu Arg Glu
                325                 330                 335

Gln His Gly Arg Asn Asp Leu Ser Gly Leu Phe Arg Thr Ser Leu Glu
                340                 345                 350

Tyr Leu Pro Leu Lys Ile Val Glu Tyr Glu Glu Ile Lys Val Arg Leu
                355                 360                 365

Glu Ala His Phe Ala Arg His Glu Met Asp Asp Leu Leu Leu Arg Phe
                370                 375                 380

Asp His Met Leu Asn Glu Gly His Val Ile Leu His Ala Ser Tyr Arg
385                 390                 395                 400

Thr Gly Leu Phe Glu Thr Ala Glu Ile Asp Arg Ile Met Glu Gln Tyr
                405                 410                 415

Val Thr Val Leu Asp Gln Phe Leu Gln Thr Pro Glu Leu Pro Ile Arg
                420                 425                 430

Glu Ile Ser Leu Leu Ser Asp Glu Glu Arg His Arg Ile Leu Asn Val
```

-continued

```
            435                 440                 445
Phe Asn Pro Pro Val Ala Gly Leu Ser Glu Gly Glu Ala Phe His Arg
    450                 455                 460
Tyr Val Glu Lys Phe Ala Arg Glu Ile Pro Asp His Pro Ala Val Val
465                 470                 475                 480
Tyr Met Asp Lys Gln Leu Thr Tyr Gly Glu Leu Asn Glu Arg Ala Glu
                485                 490                 495
Arg Leu Ala Ser Leu Leu Arg Glu Gln Gly Val Gly Lys Glu Thr Ile
                500                 505                 510
Thr Gly Ile Trp Ala Glu Arg Ser Val Glu Leu Val Gly Val Leu
            515                 520                 525
Ala Val Trp Lys Ala Gly Gly Ala Tyr Val Pro Leu Asp Pro Asp Tyr
    530                 535                 540
Pro Ala Glu Arg Ile Glu Tyr Met Leu Ser Asp Ser Asp Ala Ser Val
545                 550                 555                 560
Leu Leu Thr Gln Arg His Leu Leu Glu Arg Ala Gly Gly Trp Leu Ala
                565                 570                 575
Asp Asp Arg Leu Lys Leu Gln Ala Val Tyr Ala Met Asp Asp Glu Gln
                580                 585                 590
Ile Tyr Asn Gly Asp Ala Leu Ala Val Glu Phe Glu Ser Ala Gly Ser
            595                 600                 605
Ala Pro Gln Asp Leu Ala Tyr Val Ile Tyr Thr Ser Gly Thr Thr Gly
    610                 615                 620
Arg Pro Lys Gly Val Met Ile Glu His Gly Ser Leu Val Asn Thr Ala
625                 630                 635                 640
Asp Ala Tyr Arg Arg Glu Tyr Arg Leu Asp Gln Phe Pro Val Arg Leu
                645                 650                 655
Leu Gln Leu Ala Ser Phe Ser Phe Asp Val Phe Val Gly Asp Ile Ala
                660                 665                 670
Arg Thr Leu Tyr Asn Gly Gly Thr Met Val Ile Val Pro Lys Asp Asp
            675                 680                 685
Arg Ile Asp Pro Asn Leu Leu Tyr Gly Trp Ile Arg Asp Gln Asn Ile
    690                 695                 700
Thr Val Phe Glu Ser Thr Pro Ala Leu Ile Leu Pro Phe Met Gln His
705                 710                 715                 720
Ile Tyr Glu Glu Gly Leu Asp Val Ser Ser Met Gln Leu Leu Ile Thr
                725                 730                 735
Ser Ser Asp Ala Cys Ser Val Thr Asp Tyr Arg Leu Leu Gln Glu Arg
                740                 745                 750
Phe Gly Gly Gln Phe Arg Ile Ile Asn Ser Tyr Gly Val Thr Glu Ala
            755                 760                 765
Ala Ile Asp Ser Ser Phe Tyr Gly Glu Pro Leu Asp Lys Leu Pro Pro
    770                 775                 780
Ser Gly His Val Pro Ile Gly Lys Ala Trp Leu Asn Ala Arg Phe Tyr
785                 790                 795                 800
Ile Val Asp Ala Ala Leu Lys Pro Val Pro Val Gly Val Pro Gly Glu
                805                 810                 815
Leu Val Ile Gly Gly Ala Gly Val Ala Arg Gly Tyr Trp Asn Arg Pro
            820                 825                 830
Asp Leu Thr Ala Glu Lys Phe Ala Asp Ser Pro Phe Val Pro Gly Glu
                835                 840                 845
Arg Leu Tyr Arg Thr Gly Asp Leu Ala Arg Trp Leu Glu Asp Gly Asn
    850                 855                 860
```

```
Val Asp Phe Ile Gly Arg Ile Asp Tyr Gln Val Lys Ile Arg Gly Phe
865                 870                 875                 880

Arg Ile Glu Leu Gly Glu Ile Glu Thr Ala Leu Leu Arg Phe Pro Gly
                885                 890                 895

Val Lys Gln Ala Val Val Thr Asp Arg Thr Asp Glu Gln Gly Glu Lys
                900                 905                 910

Tyr Leu Cys Gly Tyr Val Ala Ala Asp Ala Ser Leu Gln Leu Ser Asp
                915                 920                 925

Leu Leu Ser Gln Leu Lys Gln Glu Leu Pro Ala His Met Val Pro Ala
            930                 935                 940

Arg Leu Val Ser Leu Asp Lys Leu Pro Leu Thr Pro Asn Gly Lys Ile
945                 950                 955                 960

Asp Arg Lys Ala Leu Pro Glu Pro Thr Gly Glu Val Glu Ala Gly Arg
                965                 970                 975

Glu Tyr Val Ala Pro Arg Thr Thr Leu Glu Thr Arg Leu Ala Leu Ile
            980                 985                 990

Trp Gln Gln Val Leu Gly Ile Ala  Arg Val Gly Val Gln  Asp Asp Phe
            995                 1000                1005

Phe Asp  Leu Gly Gly His  Ser Leu Arg Ala Ser  Thr Leu Val Ser
    1010                1015                1020

Lys Ile  Arg Lys Glu Leu Gln  Val Glu Val Pro Leu  Arg Glu Val
    1025                1030                1035

Phe Arg  Tyr Thr Thr Ile Glu  Gln Leu Ala Gln Arg  Ile Gly Gly
    1040                1045                1050

Leu Arg  Gln Gln Glu Thr Tyr  Glu Ile Thr Lys Ala  Ala Glu Ala
    1055                1060                1065

Glu Tyr  Tyr Pro Val Ser Ser  Glu Gln Lys Arg Leu  Tyr Val Leu
    1070                1075                1080

Arg Gln  Leu Asp Gly Ala Glu  Arg Ser Tyr Asn Met  Ser Ala Ala
    1085                1090                1095

Leu Leu  Leu Glu Gly Lys Leu  Asp Arg Met Arg Val  Glu His Ala
    1100                1105                1110

Phe Arg  Ala Leu Ile Gln Arg  His Glu Thr Leu Arg  Thr Gly Ile
    1115                1120                1125

Glu Gln  Val Gln Gly Glu Leu  Val Gln Arg Ile Tyr  Asp Glu Val
    1130                1135                1140

Glu Phe  Ala Val Asp Tyr Phe  Gln Ala Ser Glu Arg  Glu Val Glu
    1145                1150                1155

Gln Val  Val Glu Ala Tyr Tyr  His Pro Phe Asp Leu  Thr Lys Pro
    1160                1165                1170

Pro Leu  Leu Arg Ile Gly Leu  Ile Glu Val Ala Glu  Asp Arg His
    1175                1180                1185

Ile Leu  Leu Phe Asp Met His  His Ile Val Ser Asp  Gly Ile Ser
    1190                1195                1200

Thr Ala  Leu Leu Phe Asp Glu  Phe Ser Arg Leu Tyr  Arg Gly Glu
    1205                1210                1215

Glu Leu  Gly Pro Leu Arg Ile  Gln Tyr Lys Asp Tyr  Ala Val Trp
    1220                1225                1230

Gln His  Ser Glu Ala Tyr Gly  Gln Met Leu Gln Pro  Gln Lys Glu
    1235                1240                1245

Tyr Trp  Leu Glu Gln Leu Ser  Gly Glu Leu Pro Val  Leu Glu Leu
    1250                1255                1260
```

-continued

Pro Thr Asp Phe Pro Arg Pro Ala Val Gln Ser Phe Asp Gly Arg
1265                1270                1275

Thr Val Lys Phe Tyr Ile Glu Lys Asp Arg Thr Glu Lys Leu Lys
    1280                1285                1290

Glu Leu Ala Ala Arg Thr Gly Thr Thr Leu Tyr Met Val Leu Leu
    1295                1300                1305

Ser Ala Tyr Thr Ile Leu Met His Lys Tyr Ser Gly Gln Glu Asp
    1310                1315                1320

Leu Ile Val Gly Thr Pro Ile Ala Gly Arg Thr Gln Glu Glu Val
    1325                1330                1335

Gln Pro Ile Val Gly Met Phe Ile Asn Thr Leu Ala Ile Arg Ser
    1340                1345                1350

Arg Pro Glu Arg Ser Lys Pro Tyr Leu Ser Tyr Leu Glu Glu Ile
    1355                1360                1365

Lys Asp Ile Thr Leu Gly Ala Phe Glu His Gln Asn Tyr Leu Phe
    1370                1375                1380

Glu Asp Leu Val Glu Ser Leu His Ile Pro Arg Ala Thr Gly Arg
    1385                1390                1395

Asn Pro Leu Phe Asp Thr Phe Phe Ser Leu Gln Asn Thr Glu Asn
    1400                1405                1410

Glu Gln Ile Val Ile Glu Gly Leu Glu Gln Ser Phe Tyr Pro Leu
    1415                1420                1425

Glu Asn Gln Thr Ser Lys Phe Glu Leu Leu Leu Asp Ile Ser Glu
    1430                1435                1440

Leu Asp Gly Gln Leu Glu Cys Arg Leu Glu Tyr Ala Thr Ala Leu
    1445                1450                1455

Tyr Lys Gln Glu Thr Ala Glu Arg Phe Ala Arg His Tyr Asp Lys
    1460                1465                1470

Leu Leu Glu Thr Ile Ala Ala Ala Pro Asp Gly Asp Ile Ala Ser
    1475                1480                1485

Leu Glu Met Leu Lys Glu Glu Glu Ile Arg Glu Leu Val Arg Gly
    1490                1495                1500

Phe Asn Asp Ser Glu Ala Asp Tyr Pro Arg Gln Gln Thr Ile His
    1505                1510                1515

Gly Leu Phe Glu Glu Gln Ala Glu Leu Tyr Pro Asp Asn Val Ala
    1520                1525                1530

Ala Val Met Asn Glu Arg Gln Leu Thr Tyr Arg Glu Leu Asn Glu
    1535                1540                1545

Arg Ser Asn Arg Leu Ala Arg Lys Leu Arg Glu Thr Gly Val Glu
    1550                1555                1560

Ala Asp Gln Leu Val Ala Ile Leu Ala Glu Arg Ser Leu Asp Met
    1565                1570                1575

Val Val Gly Ile Leu Ala Ile Leu Lys Ala Gly Gly Ala Tyr Val
    1580                1585                1590

Pro Val Asp Pro Asp Tyr Pro Glu Glu Arg Ile Arg Phe Met Ile
    1595                1600                1605

Glu Asp Ser Gly Ala Pro Leu Leu Leu Ile Gln Lys His Leu His
    1610                1615                1620

Glu Lys Thr Asp Phe Ala Gly Thr Arg Leu Glu Leu Asp Asp Phe
    1625                1630                1635

Val Trp Gly Asp Arg Gly Ala Asn Ser Ala Glu Ala Leu Asp Ala
    1640                1645                1650

Ser Asn Leu Glu Pro Ile Ser Gly Pro Gly Asn Leu Ala Tyr Val

-continued

```
            1655                1660                1665

Ile Tyr Thr Ser Gly Thr Thr Gly Arg Pro Lys Gly Thr Leu Ile
    1670                1675                1680

Glu His Lys Asn Val Val Arg Leu Leu Phe Asn Asp Lys Asn Leu
    1685                1690                1695

Phe Asp Phe Gly Pro Ser Asp Thr Trp Thr Leu Phe His Ser Phe
    1700                1705                1710

Cys Phe Asp Phe Ser Val Trp Glu Met Tyr Gly Ala Leu Leu Tyr
    1715                1720                1725

Gly Gly Lys Leu Val Ile Val Pro Pro Leu Thr Ala Lys Asn Pro
    1730                1735                1740

Ala Asp Phe Leu Ala Leu Leu Gly Arg Glu Gln Val Thr Ile Leu
    1745                1750                1755

Asn Gln Thr Pro Thr Tyr Phe Tyr Gln Leu Leu Arg Glu Val Leu
    1760                1765                1770

Ala Asp His Pro Tyr Asp Leu Arg Ile Arg Asn Val Ile Phe Gly
    1775                1780                1785

Gly Glu Ala Leu Ser Pro Leu Leu Leu Lys Gly Phe Lys Thr Lys
    1790                1795                1800

Tyr Pro Glu Thr Lys Leu Ile Asn Met Tyr Gly Ile Thr Glu Thr
    1805                1810                1815

Thr Val His Val Thr Tyr Lys Glu Ile Thr Trp Val Glu Met Glu
    1820                1825                1830

Ala Ala Lys Ser Asn Ile Gly Lys Pro Ile Pro Thr Leu Arg Val
    1835                1840                1845

Tyr Val Leu Asp Glu Asn Arg Arg Pro Val Pro Ile Gly Val Ala
    1850                1855                1860

Gly Glu Met Tyr Val Ala Gly Glu Gly Leu Ala Arg Gly Tyr Leu
    1865                1870                1875

Asn Arg Pro Asp Leu Thr Ala Glu Lys Phe Val Asp Ser Pro Phe
    1880                1885                1890

Ala Glu Gly Glu Lys Leu Tyr Arg Ser Gly Asp Leu Ala Ala Trp
    1895                1900                1905

Leu Pro Asp Gly Asn Ile Glu Tyr Leu Gly Arg Ile Asp His Gln
    1910                1915                1920

Val Lys Ile Arg Gly Tyr Arg Ile Glu Leu Asp Glu Ile Glu Thr
    1925                1930                1935

Gln Leu Leu Asn Val Arg Gly Val Glu Glu Ala Val Val Leu Ala
    1940                1945                1950

Arg Gln Asp Gly Gly Glu Lys Ala Leu Val Ala Tyr Phe Val
    1955                1960                1965

Ala Asp Arg Thr Leu Thr Val Ser Glu Met Arg Thr Ser Leu Ala
    1970                1975                1980

Gln Gly Met Pro Gly Tyr Met Ile Pro Ser Tyr Phe Val Gln Leu
    1985                1990                1995

Glu Arg Met Pro Leu Thr Thr Asn Gly Lys Val Asp Arg Lys Ala
    2000                2005                2010

Leu Pro Glu Pro Gln Gly Gly Ile Gln Thr Gly Val Glu Tyr Val
    2015                2020                2025

Ala Pro Arg Asn Trp Thr Glu Ser Gln Leu Val Lys Ile Trp Glu
    2030                2035                2040

Glu Val Leu Gly Tyr Ser Gly Ile Gly Val Leu Asp Asn Phe Phe
    2045                2050                2055
```

-continued

```
Glu Leu Gly Gly His Ser Leu Arg Ala Thr Asn Leu Val Ser Lys
2060                2065                2070

Ile Arg Lys Glu Met Asn Val Glu Leu Pro Leu Arg Asp Val Phe
2075                2080                2085

Arg Tyr Thr Thr Val Glu Ser Met Ala Gly Ala Ile Ala Ser Leu
2090                2095                2100

Glu Glu Thr Gln His Ser Ser Ile Pro Lys Ala Glu Glu Lys Ala
2105                2110                2115

Tyr Tyr Pro Val Ser Ser Ala Gln Lys Arg Leu Tyr Val Leu His
2120                2125                2130

Gln Leu Asp Ser Ser Glu Leu Asn Tyr Asn Leu Pro Ser Ala Leu
2135                2140                2145

Gln Leu Glu Gly Ala Leu Asn Glu Ala Lys Val Glu Lys Ala Leu
2150                2155                2160

Thr Thr Leu Val Ala Arg His Asp Met Leu Arg Thr Gly Phe Glu
2165                2170                2175

Ile Val Asn Gly Glu Pro Val Gln Arg Ile His Pro Leu Val Ala
2180                2185                2190

Phe Lys Val Glu Lys Leu Gln Ala Ser Glu Asp Gln Val Ala Ala
2195                2200                2205

Ile Leu Glu Gly Phe Ile Gln Pro Phe Asp Leu Thr Gln Pro Pro
2210                2215                2220

Leu Leu Arg Ala Leu Leu Ile Glu Leu Glu Lys Glu Lys Phe Leu
2225                2230                2235

Leu Ala Leu Asp Ile His His Ile Gly Ser Asp Gly Leu Ser Met
2240                2245                2250

Asp Val Leu Leu Arg Glu Phe Val Arg Leu Tyr Asn Gly Glu Glu
2255                2260                2265

Leu Pro Glu Leu Arg Ile Gln Tyr Lys Asp Tyr Ala Val Trp Gln
2270                2275                2280

Gln Ser Glu Glu Gln Arg Gln Arg Ile Lys Arg Gln Glu Glu Tyr
2285                2290                2295

Trp Arg Gly Val Phe Ser Ser Glu Leu Pro Val Leu Glu Leu Pro
2300                2305                2310

Leu Asp Phe Ser Arg Pro Ala Val Gln Gln Phe Asp Gly Gln Thr
2315                2320                2325

Leu Thr Phe Thr Leu Asp Ala Glu Lys Ser Glu Ala Leu Lys Arg
2330                2335                2340

Leu Ala Gly Asp Ser Gly Ala Thr Leu Tyr Met Leu Leu Leu Ala
2345                2350                2355

Ala Tyr Ser Val Leu Leu His Lys Tyr Ala Gly Gln Glu Asp Ile
2360                2365                2370

Val Val Gly Thr Pro Ile Ala Ala Arg Ser His Ala Asp Leu Gln
2375                2380                2385

Pro Ile Ile Gly Met Phe Val Asn Thr Leu Ala Leu Arg Leu Arg
2390                2395                2400

Pro Ala Ala Glu Arg Thr Phe Leu Asp Tyr Leu Gln Glu Val Lys
2405                2410                2415

Glu Thr Thr Leu Gly Ala Tyr Glu His Gln Asp Tyr Pro Phe Glu
2420                2425                2430

Glu Leu Val Glu Ala Leu Gln Val Ser Arg Asp Leu Ser Arg Asn
2435                2440                2445
```

-continued

```
Pro Leu Phe Asp Thr Met Phe Ser Leu Gln Lys His Glu Ser Leu
    2450                2455                2460

Asp Leu Thr Leu Glu Gly Leu Gln Trp Ser Leu Phe Asp Ile Glu
    2465                2470                2475

Glu Lys Thr Ala Lys Phe Asp Leu Ser Phe Asp Ile Val Glu Ala
    2480                2485                2490

Asp Asn Glu Leu Val Cys Lys Ile Glu Tyr Ala Thr Ser Leu Phe
    2495                2500                2505

Arg Gln Glu Thr Met Val Arg Leu Ala Gly His Tyr Glu Gln Leu
    2510                2515                2520

Leu Ala Ser Ile Leu Ala Gln Pro Gly Ala Arg Ile Ser Asp Leu
    2525                2530                2535

Asp Ile Leu Thr Asp Ser Glu Lys His Asp Leu Leu Val Gly Phe
    2540                2545                2550

Asp Val Ser Ser Ser Ala Leu Ala Lys Gln Pro Ala Ala Glu Gly
    2555                2560                2565

Thr Gly Leu Glu Ala Asp Glu Ser Trp Arg Glu Arg Thr Phe His
    2570                2575                2580

Glu Leu Phe Glu Glu Gln Ala Glu Arg Thr Pro Gly Ala Leu Ala
    2585                2590                2595

Val Val Tyr Glu Asp Ser Lys Leu Thr Tyr Ala Glu Leu Asn Ala
    2600                2605                2610

Lys Ala Asn Arg Leu Ala Tyr Ala Leu Arg Ala Arg Gly Val Lys
    2615                2620                2625

Pro Glu Gln Val Val Gly Ile Leu Ala Gly Arg Ser Ala Glu Leu
    2630                2635                2640

Leu Val Gly Val Leu Ala Val Trp Lys Ala Gly Gly Ala Tyr Val
    2645                2650                2655

Pro Leu Asp Pro Asp Tyr Pro Ala Glu Arg Ile Glu Tyr Met Leu
    2660                2665                2670

Ala Asp Ser Gly Ala Ser Val Leu Leu Thr Gln Thr Cys Leu Leu
    2675                2680                2685

Glu Gln Ala Glu Ala Trp Arg Ser Asp Gly Ala Leu Val Leu Gln
    2690                2695                2700

Thr Val Leu Ala Leu Asp Asp Ala Ala Thr Tyr Ser Leu Gly Ala
    2705                2710                2715

Ala Glu Ala Ala Val Gly Val Gln Ala Leu Gly Glu Ala Gly Ala
    2720                2725                2730

Glu Ala Glu Ala Leu Ala Gln Ala Glu Thr Ala Ala Ala Glu Lys
    2735                2740                2745

Ser Ala Thr Ala Glu Ala Glu Lys Asn Val Leu Ala Ala Asp Leu
    2750                2755                2760

Ala Ser Asn Pro Ala Asn Val Asn Lys Pro Ser Asp Leu Ala Tyr
    2765                2770                2775

Val Ile Tyr Thr Ser Gly Thr Thr Gly Arg Pro Lys Gly Val Ala
    2780                2785                2790

Val Glu His Arg Ser Leu Val Asn Thr Ala Ala Gly Tyr Arg Arg
    2795                2800                2805

Asp Tyr Arg Leu Asp Gln Phe Pro Ile Arg Leu Leu Gln Leu Ala
    2810                2815                2820

Ser Phe Ser Phe Asp Val Phe Val Gly Asp Ile Ala Arg Thr Leu
    2825                2830                2835

Tyr Asn Gly Gly Thr Met Val Ile Val Pro Lys Asp Asp Arg Ile
```

-continued

```
                2840                2845                2850
Asp Pro Thr Arg Leu Tyr Gly Trp Ile Arg Asp Tyr Ala Val Thr
2855                2860                2865
Val Phe Glu Ser Thr Pro Ala Leu Ile Val Pro Phe Met Glu His
2870                2875                2880
Val His Ala Glu Gly Leu Asp Leu Ser Ser Met Gln Leu Leu Ile
2885                2890                2895
Thr Ser Ser Asp Ala Cys Ser Val Ala Asp Tyr Arg Thr Leu Gln
2900                2905                2910
Glu Arg Phe Gly Ser Gln Phe Arg Ile Ile Asn Ser Tyr Gly Val
2915                2920                2925
Thr Glu Ala Ala Ile Asp Ser Ser Phe Tyr Asp Glu Pro Leu Glu
2930                2935                2940
Lys Leu Pro Lys Thr Gly Ser Val Pro Ile Gly Lys Ala Trp Leu
2945                2950                2955
Asn Ala Lys Phe Tyr Ile Val Asp Ala Asn Leu Lys Pro Val Pro
2960                2965                2970
Ile Gly Val Leu Gly Glu Leu Val Ile Gly Gly Ala Gly Val Ala
2975                2980                2985
Arg Gly Tyr Leu Asn Arg Pro Asp Leu Thr Ala Glu Lys Phe Val
2990                2995                3000
Asp Ser Pro Phe Ala Ala Gly Glu Arg Leu Tyr Arg Thr Gly Asp
3005                3010                3015
Leu Ala Arg Trp Met Pro Asp Gly Asn Val Asp Phe Ile Gly Arg
3020                3025                3030
Ile Asp Asn Gln Val Lys Ile Arg Gly Tyr Arg Ile Glu Leu Gly
3035                3040                3045
Glu Ile Glu Ala Ala Met Lys Asn Phe Ala Gly Val Arg Gln Ala
3050                3055                3060
Leu Val Ile Asp Arg Thr Asp Glu Arg Gly Gln Lys Tyr Leu Cys
3065                3070                3075
Gly Tyr Val Val Ala Asp Ser Ser Phe Asp Leu Glu Gly Leu Val
3080                3085                3090
Ala His Leu Asp Ala Ala Leu Pro Ser His Met Val Pro Ser Arg
3095                3100                3105
Ile Met Arg Leu Asp Gln Met Pro Leu Thr Pro Asn Gly Lys Ile
3110                3115                3120
Asp Arg Lys Ala Leu Pro Val Pro Glu Gly Ser Ile Arg Ala Glu
3125                3130                3135
Ala Ala Tyr Thr Ala Pro Arg Thr Pro Ala Glu Gln Ala Leu Ala
3140                3145                3150
Ser Val Trp Gln Ser Val Leu Gly Val Asp Gln Val Gly Thr Met
3155                3160                3165
Asp Asn Phe Phe Ala Leu Gly Gly Asp Ser Ile Lys Ala Leu Gln
3170                3175                3180
Val Ser Ser Arg Leu Leu Gln Thr Gly Tyr Lys Leu Val Met Lys
3185                3190                3195
Asp Leu Phe His Tyr Pro Thr Ile Ser Ala Leu Ser Leu Gln Leu
3200                3205                3210
Gln Thr Ala Glu Arg Thr Ala Ser Gln Ala Glu Val Thr Gly Glu
3215                3220                3225
Val Ile Leu Thr Pro Ile Gln Arg Trp Phe Phe Glu Gln Asn Pro
3230                3235                3240
```

```
Ala Asp Val His His Ser Asn Gln Ala Phe Met Gln Phe Ser Lys
3245                3250                3255

Glu Gly Phe Asp Glu Glu Ala Leu Arg Gln Ala Val Arg Gln Ile
3260                3265                3270

Val Val His His Asp Ala Leu Arg Thr Val Tyr Arg Gln Ala Asp
3275                3280                3285

Asn Gly Tyr Thr Ala Trp Asn Arg Gly Ala Gly Glu Asn Glu Ala
3290                3295                3300

Leu Phe Asp Leu Glu Val Val Asp Phe Lys Gly Val Gly Asp Val
3305                3310                3315

Lys Glu Ala Val Glu Ala Lys Ala Asn Asp Ile Gln Ala Ser Ile
3320                3325                3330

Asp Leu Glu Asn Gly Pro Leu Val Lys Leu Gly Leu Phe Arg Cys
3335                3340                3345

Asp Asp Gly Asp His Leu Leu Ile Ala Ile His His Leu Val Val
3350                3355                3360

Asp Gly Val Ser Trp Arg Ile Leu Leu Glu Asp Phe Ala Ala Gly
3365                3370                3375

Tyr Glu Gln Ala Leu Gln Gly Gln Pro Ile Arg Leu Pro Leu Lys
3380                3385                3390

Thr Asp Ser Phe Gln Thr Trp Ala Lys Gln Leu Ala Asp Tyr Ala
3395                3400                3405

Asn Ser Pro Ala Met Glu Ser Glu Arg Glu Tyr Trp Gln His Ile
3410                3415                3420

Glu Gln Leu Thr Tyr Glu Pro Leu Pro Lys Asp Phe Glu Gln Gly
3425                3430                3435

Arg Ser Lys Leu Lys Asp Ser Gly Leu Val Thr Val Arg Trp Thr
3440                3445                3450

Ala Glu Glu Thr Glu Gln Leu Leu Lys Gln Ala His Arg Ala Tyr
3455                3460                3465

His Thr Glu Met Asn Asp Leu Leu Leu Ala Ala Leu Gly Leu Ala
3470                3475                3480

Leu Gln Ala Trp Ser Gly Arg Glu Arg Val Leu Val Asn Leu Glu
3485                3490                3495

Gly His Gly Arg Glu Asp Ile Leu Pro Asp Val Asp Ile Thr Arg
3500                3505                3510

Thr Val Gly Trp Phe Thr Ser Gln Phe Pro Val Val Leu Glu Pro
3515                3520                3525

Gly His Ala Gln Ala Leu Gly His Gln Val Lys Gln Val Lys Glu
3530                3535                3540

Ser Leu Arg Arg Ile Pro Asn Lys Gly Ile Gly Tyr Gly Ile Leu
3545                3550                3555

Arg Tyr Leu Ser Ala Pro Arg Glu Gly Glu Tyr Phe Val Leu Glu
3560                3565                3570

Pro Glu Ile Ser Phe Asn Tyr Leu Gly Gln Phe Asp His Asp Tyr
3575                3580                3585

Glu Ser Ser Ser Ser Gln Pro Ser Pro Phe Ser Pro Gly Ser Asp
3590                3595                3600

Ser Ser Pro Asn Ala Val Met Asp Tyr Val Leu Asp Ile Asn Gly
3605                3610                3615

Met Val Ser Glu Gly Ala Leu Glu Leu Thr Ile Arg Tyr Gly Glu
3620                3625                3630
```

-continued

Thr Gln Tyr Lys Arg Glu Val Glu Arg Leu Gly Thr Leu Leu
3635              3640              3645

Gln Ser Ser Leu Arg Glu Val Ile Ser His Cys Leu Ser Lys Glu
3650              3655              3660

Arg Pro Glu Leu Thr Pro Ser Asp Val Leu Leu Gln Asp Val Thr
3665              3670              3675

Val Glu Glu Leu Glu Arg Leu Ser Glu His Thr Val Ala Leu Gly
3680              3685              3690

Glu Leu Glu Asn Val Tyr Thr Leu Thr Pro Leu Gln Lys Gly Met
3695              3700              3705

Leu Phe His Ser Leu Leu Asp Ala Asp Ser Glu Ala Tyr Phe Glu
3710              3715              3720

Gln Val Thr Phe Asp Leu Tyr Gly Ser Leu Asn Val Glu Ala Phe
3725              3730              3735

Thr Arg Gly Leu Asp Thr Leu Val Gln Arg Asn Glu Ala Leu Arg
3740              3745              3750

Thr Asn Phe Ile Thr Gly Trp Arg Asp Glu Pro Ile Gln Val Val
3755              3760              3765

Phe Arg Glu Arg Lys Cys Glu Val Tyr Phe Glu Asp Ile Arg Ser
3770              3775              3780

Val Ser Asp Glu His Pro Glu Lys Thr Ile Ala Asp Phe Val Ser
3785              3790              3795

Ala Asp Lys Ala Asn Lys Phe Asp Leu Ala Arg Gly Pro Leu Met
3800              3805              3810

Arg Val Thr Val Val Arg Thr Gly Asp Glu Ser Tyr His Val Ile
3815              3820              3825

Trp Ser His His His Ile Leu Met Asp Gly Trp Cys Met Ser Phe
3830              3835              3840

Met Ile Lys Glu Val Phe Asp Thr Tyr Phe Ala Phe Gln Glu Lys
3845              3850              3855

Arg Thr Leu Glu Leu Pro Pro Val Thr Ser Tyr Ser Arg Tyr Ile
3860              3865              3870

Glu Trp Leu Glu Ala Gln Asp Ala Ala Lys Ala Ser Arg Tyr Trp
3875              3880              3885

Ser Glu Tyr Leu Ala Gly Tyr Asp Gln Gln Thr Lys Leu Pro Gln
3890              3895              3900

Glu Lys Thr Gln Leu Lys Gln Gly Ala Phe Glu Ala Ala Glu Ile
3905              3910              3915

Asp Val Glu Leu Ser Lys Glu Leu Thr Gly Gln Ile Glu Arg Val
3920              3925              3930

Ala Arg Gln Gln Gln Val Thr Leu Asn Thr Phe Met Gln Thr Val
3935              3940              3945

Trp Gly Leu Val Leu Gln Ile Tyr Asn Asn Ser Glu Asp Val Val
3950              3955              3960

Phe Gly Ser Val Val Ser Gly Arg Pro Ala Glu Ile Pro Gly Ile
3965              3970              3975

Glu Ser Met Ile Gly Leu Phe Ile Asn Thr Ile Pro Val Arg Ile
3980              3985              3990

Gln Gly Lys Ala Glu Glu Arg Val Ala Asp Ile Leu Arg Lys Thr
3995              4000              4005

Gln Asp Gln Ala Leu Ala Ser Gly Ala Tyr Glu Thr Phe Pro Leu
4010              4015              4020

Phe Glu Ile Gln Ser Leu Ser Glu Gln Lys Arg Asp Leu Ile Asn

-continued

```
            4025                4030                4035
His Ile Met Val Phe Glu Asn Tyr Pro Met Glu Glu Gln Ile Glu
            4040                4045                4050

Gln Val Val Gly Gly Gly Arg Glu Ala Leu Lys Ile Ala Asn Ile
            4055                4060                4065

Gln Ser Pro Glu Gln Thr Asn Tyr Asp Leu Asp Ile Thr Val Ile
            4070                4075                4080

Pro Glu Glu His Ile Leu Leu Arg Phe Thr Tyr Asn Ala Leu Thr
            4085                4090                4095

Phe Arg Glu Asp Asp Ile Arg Gln Ile His Ser His Phe Ala Trp
            4100                4105                4110

Ala Leu Glu Lys Val Ala Ala Asn Pro Asn Ile Leu Val Asn Gln
            4115                4120                4125

Leu Glu Leu Leu Thr Ala Ala Glu Lys Glu Gln Ile Leu Gly Ala
            4130                4135                4140

Phe Asn Pro Ala Gln Pro Glu Ala Ala Pro Ala Ala Ala Phe His
            4145                4150                4155

Arg Leu Phe Glu Glu Gln Val Glu Arg Thr Pro Glu Glu Ala Ala
            4160                4165                4170

Val Val Tyr Glu Asn Asp Arg Leu Thr Tyr Ala Glu Leu Asn Glu
            4175                4180                4185

Arg Ala Asn Arg Leu Ala Ala Thr Leu Arg Ala Ser Gly Ile Gly
            4190                4195                4200

Arg Glu Thr Ile Val Gly Ile Leu Ala Glu Arg Ser Val Asp Leu
            4205                4210                4215

Leu Val Ala Val Leu Ala Val Trp Lys Ala Gly Ala Tyr Val
            4220                4225                4230

Pro Leu Asp Pro Asp Tyr Pro Ala Asp Arg Val Arg Phe Met Leu
            4235                4240                4245

Glu Asp Ser Gly Ala Lys Val Leu Leu Thr Gln Thr Ala Leu Arg
            4250                4255                4260

Glu Arg Ala Glu Ala Trp Leu Gly Glu Glu Leu Ala Leu Ala
            4265                4270                4275

Ala Val Leu Tyr Leu Asp Asp Glu Ala Ser Tyr Asn Glu Glu Arg
            4280                4285                4290

Ala Asn Ala Pro Val Gly Ser Gly Met Val Ser Gly Lys Leu Thr
            4295                4300                4305

Asp Ala Val Asp Asp Gly Asp Glu Ser His Gln Asn Val Gly Thr
            4310                4315                4320

Asp Gly Phe His Glu Ala Arg Pro Glu Asp Leu Ala Tyr Val Ile
            4325                4330                4335

Tyr Thr Ser Gly Thr Thr Gly Lys Pro Lys Gly Val Met Ile Glu
            4340                4345                4350

His Arg Ser Leu Val Asn Thr Ala Ala Gly Tyr Arg Arg Glu Tyr
            4355                4360                4365

Arg Leu Asp Gln Phe Pro Val Arg Leu Leu Gln Leu Ala Ser Phe
            4370                4375                4380

Ser Phe Asp Val Phe Val Gly Asp Ile Ala Arg Thr Leu Tyr Asn
            4385                4390                4395

Gly Gly Thr Met Val Ile Val Pro Lys Asp Asp Arg Ile Asp Pro
            4400                4405                4410

Ser Arg Leu His His Trp Met Glu Arg Glu Arg Val Thr Ile Phe
            4415                4420                4425
```

```
Glu Ser Thr Pro Ala Leu Ile Val Pro Phe Leu Glu Tyr Val His
    4430                4435                4440

Asp Gln Gln Leu Asp Met Ser Trp Met Glu Leu Leu Ile Thr Ser
    4445                4450                4455

Ser Asp Ser Cys Ser Val Ala Asp Tyr Arg Thr Leu Gln Glu Arg
    4460                4465                4470

Phe Gly Ser Leu Phe Arg Ile Ile Asn Ala Tyr Gly Val Thr Glu
    4475                4480                4485

Ala Ala Ile Asp Ser Ser Phe Tyr Asp Glu Leu Ala Lys Leu
    4490                4495                4500

Pro Gln Thr Gly His Val Pro Ile Gly Lys Ala Trp Leu Asn Ala
    4505                4510                4515

Lys Phe Tyr Ile Val Asp Ala His Leu Asn Pro Val Pro Val Gly
    4520                4525                4530

Val Leu Gly Glu Leu Val Ile Gly Gly Val Gly Val Ala Arg Gly
    4535                4540                4545

Tyr Leu Asn Arg Pro Glu Leu Thr Gly Glu Lys Phe Val Asp Ser
    4550                4555                4560

Pro Phe Ala Ala Gly Glu Arg Leu Tyr Arg Thr Gly Asp Leu Ala
    4565                4570                4575

Arg Trp Met Glu Asp Gly Asn Val Asp Phe Ile Gly Arg Ile Asp
    4580                4585                4590

Asn Gln Ala Lys Ile Arg Gly Tyr Arg Ile Glu Thr Gly Glu Val
    4595                4600                4605

Glu Ala Lys Leu Leu Ser Val Gly Gly Val Lys Glu Ala Val Val
    4610                4615                4620

Val Val Arg Glu Asp Gln Glu Gly Gln Lys Ala Leu Cys Ala Tyr
    4625                4630                4635

Tyr Thr Ala Glu Glu Gly Leu Thr Ala Ala Asp Leu Lys Arg Ala
    4640                4645                4650

Ile Ala Ser Glu Leu Pro Gly Tyr Met Ile Pro Ser Tyr Phe Val
    4655                4660                4665

Glu Leu Glu Arg Leu Pro Leu Thr Pro Asn Gly Lys Ile Asp Arg
    4670                4675                4680

Lys Ala Leu Pro Ala Pro Glu Gly Gly Ala Gly Gly Gly Arg Glu
    4685                4690                4695

Tyr Val Ala Pro Arg Thr Glu Leu Glu Ala Lys Leu Ala Ala Ile
    4700                4705                4710

Trp Gln Asp Val Leu Val Arg Glu Lys Ala Val Gly Val Thr Asp
    4715                4720                4725

Asn Phe Phe Asp Leu Gly Gly His Ser Leu Arg Ala Thr Thr Leu
    4730                4735                4740

Val Ser Lys Met His Lys Glu Leu Gly Val Glu Phe Pro Leu Arg
    4745                4750                4755

Asp Val Phe Arg Tyr Pro Thr Val Glu Glu Met Ala Ala Ala Met
    4760                4765                4770

Glu Arg Leu Glu Ile Gly Ser Phe Met Ala Ile Pro Ala Ala Glu
    4775                4780                4785

Pro Ser Glu Tyr Tyr Pro Leu Ser Ser Ala Gln Lys Arg Leu Tyr
    4790                4795                4800

Ile Leu Asn Gln Leu Glu Gly Ala Glu Leu Ser Tyr Asn Ile Pro
    4805                4810                4815
```

```
Gly Ala Met Leu Leu Glu Gly Glu Leu Asp Arg Gln Arg Phe Glu
4820             4825                 4830
Glu Ala Phe Arg Gly Leu Val Ala Arg His Glu Thr Leu Arg Thr
4835             4840                 4845
Gly Phe Glu Met Val Lys Gly Glu Ala Val Gln Arg Ile Tyr Glu
4850             4855                 4860
Glu Ala Ala Phe Gln Val Glu Tyr Val Gln Ile Ser Ala Glu Gln
4865             4870                 4875
Ala Glu Glu Thr Val Arg Gln Phe Val Arg Pro Phe Asp Leu Ala
4880             4885                 4890
Lys Pro Pro Leu Leu Arg Val Gly Leu Ala Glu Leu Ala Pro Asp
4895             4900                 4905
Arg His Ile Leu Met Phe Asp Thr His His Ile Val Ser Asp Gly
4910             4915                 4920
Val Ser Ile Asp Val Leu Ile Glu Glu Leu Val Arg Leu Tyr Ser
4925             4930                 4935
Gly Glu Gln Leu Glu Pro Leu Arg Ile Gln Tyr Lys Asp Tyr Ala
4940             4945                 4950
Val Trp Gln Gln Ser Asp Glu Gln Lys Ala Gln Leu Ala Lys Gln
4955             4960                 4965
Glu Ala Tyr Trp Leu Asp Met Phe Arg Gly Glu Leu Pro Val Leu
4970             4975                 4980
Glu Leu Pro Thr Asp Tyr Pro Arg Pro Ala Met Gln Ser Tyr Glu
4985             4990                 4995
Gly Arg Thr Leu Gln Leu Phe Met His Ser Glu Lys Ser Glu Gly
5000             5005                 5010
Leu Lys Arg Leu Ala Ala Glu Asn Gly Ala Thr Leu Tyr Met Val
5015             5020                 5025
Leu Leu Ala Gly Tyr Thr Ile Leu Leu His Lys Tyr Thr Gly Gln
5030             5035                 5040
Glu Asp Val Val Val Gly Thr Pro Ile Ala Gly Arg Asn His Ser
5045             5050                 5055
Asp Val Gln Pro Leu Ile Gly Met Phe Val Asn Thr Leu Ala Ile
5060             5065                 5070
Arg Ser Tyr Pro Ala Ala Asp Lys Thr Phe Leu Glu Tyr Leu Lys
5075             5080                 5085
Glu Ile Lys Glu Thr Thr Leu Gly Ala Phe Glu His Gln Asn Tyr
5090             5095                 5100
Pro Phe Glu Glu Leu Val Asp Lys Val Asn Val Ala Arg Asp Leu
5105             5110                 5115
Arg Arg Asn Pro Leu Phe Asp Thr Met Phe Ala Leu Gln Asn Thr
5120             5125                 5130
Glu Asn Leu Glu Ile Gln Leu Pro Gly Leu His Leu Ser Thr Tyr
5135             5140                 5145
Ala Ser Glu Glu Ile Val Ser Lys Phe Asp Leu Ser Leu Asp Val
5150             5155                 5160
Thr Glu Ile Glu Glu Gly Leu Glu Tyr Leu Phe Glu Tyr Ala Thr
5165             5170                 5175
Ala Leu Tyr Lys Thr Glu Thr Val Glu Lys Leu Ala Ala His Tyr
5180             5185                 5190
Leu Gln Leu Leu Glu Ser Ile Leu Arg Asn Pro Ser Ala Thr Ile
5195             5200                 5205
Ala Glu Leu Gly Ile Leu Thr Pro Ala Glu Lys Glu Gln Ile Leu
```

-continued

```
                5210                5215                5220
Gly Ala Phe Asn Pro Ala Gln Pro Glu Ala Ala Pro Ala Thr Ala
        5225                5230                5235
Phe His Arg Leu Phe Glu Glu Gln Val Glu Arg Thr Pro Glu Glu
        5240                5245                5250
Ala Ala Val Val Tyr Glu Asn Asp Arg Leu Thr Tyr Ala Glu Leu
        5255                5260                5265
Asn Lys Arg Ala Asn Arg Leu Ala Ala Thr Leu Arg Ala Gly Gly
        5270                5275                5280
Ile Gly Arg Glu Thr Ile Val Gly Ile Leu Ala Glu Arg Ser Val
        5285                5290                5295
Asp Leu Leu Val Ala Val Leu Ala Ile Trp Lys Ala Gly Gly Ala
        5300                5305                5310
Tyr Val Pro Leu Asp Pro Asp Tyr Pro Ala Asp Arg Val Arg Phe
        5315                5320                5325
Met Leu Glu Asp Ser Gly Ala Lys Val Leu Leu Thr Gln Thr Pro
        5330                5335                5340
Leu Arg Glu Arg Ala Glu Ala Trp Leu Gly Glu Glu Leu Ala
        5345                5350                5355
Leu Ala Ala Val Leu Tyr Leu Asp Asp Glu Thr Ser Tyr Ser Glu
        5360                5365                5370
Glu Arg Ala Asn Ala Pro Ile Gly Ser Gly Met Val Ser Gly Lys
        5375                5380                5385
Leu Thr Asp Ala Val Asn Asp Gly Asp Glu Ser His Gln Asn Val
        5390                5395                5400
Gly Thr Asp Ser Phe His Glu Ala Arg Pro Glu Asn Leu Ala Tyr
        5405                5410                5415
Val Ile Tyr Thr Ser Gly Thr Thr Gly Lys Pro Lys Gly Val Met
        5420                5425                5430
Ile Glu His Arg Ser Leu Val Asn Thr Ala Val Gly Tyr Arg Arg
        5435                5440                5445
Glu Tyr Arg Leu Asp Gln Phe Pro Val Arg Leu Leu Gln Leu Ala
        5450                5455                5460
Ser Phe Ser Phe Asp Val Phe Val Gly Asp Ile Ala Arg Thr Leu
        5465                5470                5475
Tyr Asn Gly Gly Thr Met Val Ile Val Pro Lys Asp Asp Arg Ile
        5480                5485                5490
Asp Pro Ser Arg Leu His His Trp Met Glu Arg Glu Arg Val Thr
        5495                5500                5505
Ile Phe Glu Ser Thr Pro Ala Leu Ile Val Pro Phe Leu Glu Tyr
        5510                5515                5520
Val His Asp Gln Gln Leu Asp Met Ser Trp Met Glu Leu Leu Ile
        5525                5530                5535
Thr Ser Ser Asp Ser Cys Ser Val Ala Asp Tyr Arg Thr Leu Gln
        5540                5545                5550
Glu Arg Phe Gly Ser Leu Phe Arg Ile Ile Asn Ala Tyr Gly Val
        5555                5560                5565
Thr Glu Ala Ala Ile Asp Ser Ser Phe Tyr Asp Glu Glu Leu Ala
        5570                5575                5580
Lys Leu Pro Gln Thr Gly His Val Pro Ile Gly Lys Ala Trp Leu
        5585                5590                5595
Asn Ala Lys Phe Tyr Ile Val Asp Ala His Leu Asn Pro Val Pro
        5600                5605                5610
```

-continued

Val Gly Val Met Gly Glu Leu Val Ile Gly Gly Val Gly Val Ala
5615                5620                5625

Arg Gly Tyr Leu Asn Arg Pro Glu Leu Thr Glu Glu Lys Phe Val
5630                5635                5640

Asp Ser Pro Phe Ala Ala Gly Glu Arg Leu Tyr Arg Thr Gly Asp
5645                5650                5655

Leu Ala Arg Trp Met Glu Asp Gly Asn Val Asp Phe Ile Gly Arg
5660                5665                5670

Ile Asp Asn Gln Ala Lys Ile Arg Gly Tyr Arg Ile Glu Thr Gly
5675                5680                5685

Glu Ile Glu Ser Gln Leu Leu Arg Val Glu Gly Val Arg Glu Ala
5690                5695                5700

Val Val Leu Val Arg Ser Asp Ser Asn Gly Gln Lys Ala Leu Ser
5705                5710                5715

Ala Tyr Tyr Thr Ile Asp Gly Glu Leu Thr Ala Ala Asp Leu Lys
5720                5725                5730

Arg Ala Ile Ser Ser Glu Leu Pro Gly Tyr Met Ile Pro Ser Tyr
5735                5740                5745

Phe Val Glu Leu Glu Arg Leu Pro Leu Thr Pro Asn Gly Lys Ile
5750                5755                5760

Asp Arg Lys Glu Leu Pro Ala Pro Glu Gly Gly Ala Ser Ala Gly
5765                5770                5775

Arg Glu Tyr Val Ala Pro Arg Thr Glu Leu Glu Ala Lys Leu Val
5780                5785                5790

Ala Ile Trp Gln Asp Val Leu Gly Pro Ile Thr Ile Gly Val Thr
5795                5800                5805

Asp Asn Phe Phe Asp Leu Gly Gly His Ser Leu Arg Ala Thr Thr
5810                5815                5820

Leu Val Ser Lys Val His Lys Glu Leu Ser Val Asp Leu Pro Leu
5825                5830                5835

Arg Asp Val Phe Arg His Ser Thr Ile Glu Ala Met Ala Glu Ala
5840                5845                5850

Ile Ser Gln Leu Glu Arg Gln Glu His Leu Ser Ile Pro Val Leu
5855                5860                5865

Asp Lys Arg Asp Tyr Tyr Pro Leu Ser Ser Val Gln Lys Arg Leu
5870                5875                5880

Tyr Ile Gln Gln Gln Met Glu Gly Ala Glu Leu Ser Tyr Asn Met
5885                5890                5895

Ser Gly Met Thr Val Leu Val Gly Arg Leu Glu Arg Asn Gln Phe
5900                5905                5910

Glu Ala Ala Leu Lys Gly Leu Ile Ala Arg His Glu Ile Leu Arg
5915                5920                5925

Thr Gly Phe Glu Met Val Asp Gly Glu Pro Val Gln Arg Ile Tyr
5930                5935                5940

Pro Asp Leu Lys Phe Ala Val Glu Tyr Thr Lys Ala Met Glu Ser
5945                5950                5955

Glu Thr Lys Ser Ile Val Asp Gly Phe Val Arg Val Phe Asp Leu
5960                5965                5970

Glu Arg Pro Pro Leu Leu Arg Val Gly Leu Val Glu Met Glu Ala
5975                5980                5985

Glu Arg His Leu Leu Met Leu Asp Ile His His Ile Val Thr Asp
5990                5995                6000

```
Gly Met Ser Met Gly Ile Phe Val Glu Leu Leu Arg Leu Tyr
    6005            6010                6015

Asn Gly Glu Thr Leu Glu Pro Leu Arg Ile Gln Tyr Lys Glu Phe
    6020            6025                6030

Ala Ala Trp Gln Gln Ser Glu Pro Val Lys Glu Arg Leu Lys Arg
    6035            6040                6045

Gln Glu Ala Tyr Trp Leu Asp Val Leu Glu Gly Glu Leu Pro Thr
    6050            6055                6060

Leu Glu Leu Pro Thr Asp Phe Val Arg Pro Ala Ala Arg Ser Phe
    6065            6070                6075

Glu Gly Asp Val Leu Pro Phe Ser Ile Asp Lys Gln Met Thr Asp
    6080            6085                6090

Ser Leu Gln Arg Ile Ala Asp Glu Asn Gly Ala Thr Leu Tyr Met
    6095            6100                6105

Val Leu Leu Ala Ala Tyr Ser Ile Leu Leu Ser Lys Tyr Ser Gly
    6110            6115                6120

Gln Glu Asp Phe Ile Val Gly Thr Pro Val Ser Gly Arg Thr His
    6125            6130                6135

Ala Asp Leu Glu Pro Leu Ile Gly Met Phe Val Asn Thr Leu Ala
    6140            6145                6150

Ile Arg His Tyr Pro Ser Gly Glu Lys Thr Phe Leu Ala Tyr Leu
    6155            6160                6165

Asn Glu Val Lys Glu Thr Met Leu Gly Ala Tyr Glu His Gln Asp
    6170            6175                6180

Tyr Pro Phe Glu Glu Leu Val Lys Lys Leu Gln Ala Pro Arg Asp
    6185            6190                6195

Gln Ser Arg Asn Pro Val Phe Asp Val Met Phe Ala Leu Glu Thr
    6200            6205                6210

Lys Glu Asp Asn Val Gln Ser Phe Gly Asp Ile Lys Ile Glu Ser
    6215            6220                6225

Tyr Pro Glu Thr His Thr Val Ser Gln Phe Asp Leu Thr Leu Val
    6230            6235                6240

Ile Ser Leu Leu Asp Glu Gly Met Asn Gly Gln Phe Glu Tyr Ala
    6245            6250                6255

Thr Lys Leu Phe Thr Arg Asn Leu Ile Asp Asn Phe Ala Gln Asp
    6260            6265                6270

Leu Leu Val Ile Ile Thr Gln Ile Cys Glu Gln Pro Ser Ala Leu
    6275            6280                6285

Leu Lys Asp Ile Ser Leu Asn Gly Gln Ser Glu Gln Glu Gln Asp
    6290            6295                6300

Val Leu Glu Ala Ile Asp Ile Ile Phe
    6305            6310
```

<210> SEQ ID NO 7
<211> LENGTH: 297
<212> TYPE: PRT
<213> ORGANISM: Polymyxa betae

<400> SEQUENCE: 7

```
Met Ala Phe Glu Lys Glu Thr Leu Phe Trp Asn Glu Lys Phe Gly Asn
1               5                   10                  15

Asp Asp Tyr Thr Leu Thr Arg Leu Pro Tyr Ser Lys Ala Pro Ser Ser
                20                  25                  30

Leu Ala Pro Ile Met Thr Thr Val Gly Gly Ser Leu Ser Glu Glu Ala
            35                  40                  45
```

```
Ala Gln Arg Val Leu Gln Met Ser Lys Gly Ala Pro Leu Ala Ala Phe
 50                  55                  60

Met Ile Leu Leu Ala Gly Val Gln Ser Leu Leu His Lys Tyr Thr Gly
 65                  70                  75                  80

Ala Ser Asp Ile Leu Val Gly Met Pro Val Val Arg Lys Pro Thr Glu
                 85                  90                  95

Thr Arg Arg Ser Val Asn His Thr Val Ile Leu Lys Asn Ser Leu Ser
            100                 105                 110

Ala Gly Ala Thr Phe Lys Thr Leu Leu Asn Glu Leu Arg Thr Ser Leu
        115                 120                 125

Pro Arg Ala Ile Gln His Gln His Ile Pro Phe Leu Lys Met Thr Glu
    130                 135                 140

Lys Leu Asp Leu Gln Tyr Ala Asp Gly Ile Pro Val Val His Thr Leu
145                 150                 155                 160

Val Ser Leu Lys Glu Leu His Leu Asp Glu Ile Gly Gln Asn Val Val
                165                 170                 175

Thr Asp Cys Ser Phe Glu Phe Ser Leu Thr Gly Gly Thr Ile Gln Leu
            180                 185                 190

Ala Leu Ser Tyr Asn Glu His Leu Tyr Asp Ser Glu Phe Met Thr Arg
        195                 200                 205

Val Val Gly His Leu Asn Arg Leu Leu Val Val Gly Leu His Glu Leu
    210                 215                 220

Glu Leu Asp Ile Val Arg Ala Asp Met Leu Ser Glu Asp Glu Lys Phe
225                 230                 235                 240

Gln Leu Leu Gln Ser Phe Asn Asp Thr Glu Lys Asp Tyr Pro Arg Asp
                245                 250                 255

Arg Thr Ile His Gln Leu Val Glu Glu Gln Ala Lys Arg Val Pro Glu
            260                 265                 270

Ala Thr Ala Val Val Phe Glu Gly Arg Arg Leu Ser Tyr Ala Glu Leu
        275                 280                 285

Asn Glu Arg Ala Asn Arg Leu Ala Arg
    290                 295

<210> SEQ ID NO 8
<211> LENGTH: 505
<212> TYPE: PRT
<213> ORGANISM: Polymyxa betae

<400> SEQUENCE: 8

Thr Leu Arg Ser Ile Gly Val Leu Pro Asn Gln Leu Val Gly Leu Met
 1               5                  10                  15

Val Arg Arg Ser Leu Glu Thr Val Val Gly Ile Leu Ala Val Leu Lys
                20                  25                  30

Ala Gly Gly Ala Tyr Val Pro Ile Asp Pro Glu Tyr Pro Glu Glu Arg
            35                  40                  45

Ile Arg Tyr Ile Leu Glu Asn Ser Asn Ala Gln Leu Leu Leu Thr Gln
        50                  55                  60

Arg Glu Leu Leu Gln Leu Gln Val Pro Phe Glu Gly Thr Val Val Ala
 65                  70                  75                  80

Leu Asp Asp Glu Gln Ala Tyr Ser Asp Gly Ser Asn Leu Glu Pro
                 85                  90                  95

Ala Ser Gly Pro Asn Asp Leu Ala Tyr Val Ile Tyr Thr Ser Gly Thr
            100                 105                 110

Thr Gly Asn Pro Lys Gly Val Met Leu Glu His His Gly Leu Val Ser
```

```
                 115                 120                 125
Leu Lys Leu Met Phe Ala Asp Arg Leu Gly Ile Thr Glu His Asp Arg
    130                 135                 140

Ile Val Gln Phe Ala Ser Leu Ser Phe Asp Ala Ser Cys Trp Glu Val
145                 150                 155                 160

Phe Lys Ala Leu Tyr Phe Gly Ala Ala Leu Tyr Ile Pro Thr Ala Glu
                165                 170                 175

Thr Ile Leu Asp Asn Arg Leu Phe Glu Ser Tyr Met Asn Glu His Ala
            180                 185                 190

Ile Thr Ala Ala Ile Leu Pro Pro Thr Tyr Ser Ala Tyr Leu Asn Pro
        195                 200                 205

Asp Arg Leu Pro Ser Leu Thr Lys Leu Val Thr Gly Gly Ser Ala Val
    210                 215                 220

Ser Ala Glu Phe Val Gln Gln Trp Lys Arg Lys Val His Tyr Phe Asn
225                 230                 235                 240

Ala Tyr Gly Pro Thr Glu Ala Ser Ile Val Thr Thr Leu Trp Asp Ala
                245                 250                 255

Asp Glu Glu Gln Pro Glu Gly Arg Val Ile Pro Ile Gly Arg Pro Leu
            260                 265                 270

Ala Asn His Arg Ile Phe Ile Leu Asp Ala His Leu Gln Leu Val Pro
        275                 280                 285

Pro Gly Val Asp Gly Glu Leu Cys Val Ala Gly Val Gly Leu Ala Arg
    290                 295                 300

Gly Tyr Leu Asn His Pro Glu Leu Thr Ala Glu Lys Phe Val Glu His
305                 310                 315                 320

Pro Phe Ala Pro Gly Glu Arg Leu Tyr Arg Thr Gly Asp Leu Ala Arg
                325                 330                 335

Trp Leu Pro Asp Gly Asn Val Glu Tyr Leu Gly Arg Ile Asp His Gln
            340                 345                 350

Val Lys Ile Arg Gly Phe Arg Ile Glu Ile Gly Glu Ile Glu Glu Gln
        355                 360                 365

Leu Leu Lys Ile Asp Ser Val Gln Glu Thr Ile Val Ile Ala Arg Glu
    370                 375                 380

Gly Lys Ser Gly Gln Glu Leu Cys Ala Tyr Leu Val Ala Gly Arg Pro
385                 390                 395                 400

Leu Thr Leu Gly Glu Leu Arg Ser Ala Leu Ala Gln Lys Leu Pro Asn
                405                 410                 415

Tyr Met Ile Pro Ala His Phe Val Gln Leu Pro Gln Met Pro Leu Thr
            420                 425                 430

Pro Asn Asp Lys Ile Asp Arg Lys Ala Leu Pro Ala Pro Glu Gly Asn
        435                 440                 445

Ala Leu Thr Gly Gly Ala Tyr Val Ala Pro Arg Asn Glu Ala Glu Arg
    450                 455                 460

Thr Leu Ala Asp Val Trp Gln Ala Val Leu Asn Ala Asp Arg Val Gly
465                 470                 475                 480

Val Thr Asp His Phe Phe Glu Leu Gly Gly Asp Ser Ile Lys Ser Ile
                485                 490                 495

Gln Val Ser Ser Arg Leu His Gln Ala
            500                 505

<210> SEQ ID NO 9
<211> LENGTH: 18
<212> TYPE: PRT
<213> ORGANISM: Polymyxa betae
```

-continued

<400> SEQUENCE: 9

Gly Tyr Lys Leu Glu Ile Arg Asp Leu Phe Lys Tyr Pro Thr Ile Ser
1               5                   10                  15

Gln Leu

<210> SEQ ID NO 10
<211> LENGTH: 64
<212> TYPE: PRT
<213> ORGANISM: Polymyxa betae

<400> SEQUENCE: 10

Ser Leu His Val Lys Pro Ile Gly Arg Thr Ile Asp Gln Gly Glu Ile
1               5                   10                  15

Thr Gly Glu Thr Ala Leu Thr Pro Ile Gln His Trp Phe Glu Ser
            20                  25                  30

Ser Phe Ala Asp Pro His His Phe Asn Gln Ser Val Met Leu Tyr Arg
        35                  40                  45

Lys Glu Arg Phe Asp Glu Glu Thr Val Arg Gln Val Leu Gln Lys Leu
    50                  55                  60

<210> SEQ ID NO 11
<211> LENGTH: 17
<212> TYPE: PRT
<213> ORGANISM: Polymyxa betae

<400> SEQUENCE: 11

Ala Glu His His Asp Ala Leu Arg Met Val Phe Arg Lys Thr Glu Gln
1               5                   10                  15

Gly

<210> SEQ ID NO 12
<211> LENGTH: 460
<212> TYPE: PRT
<213> ORGANISM: Polymyxa betae

<400> SEQUENCE: 12

Phe Ser Ala Arg Asn Arg Ala Ile Gln Asp Gly Gly Leu Phe Thr Leu
1               5                   10                  15

Asp Val Phe Asp Phe Lys Asp Ala Glu Asn Thr Glu Gln Ala Val Glu
            20                  25                  30

Ala Lys Ala Thr Asp Ile Gln Ala Gly Ile Asp Leu Glu Asn Gly Leu
        35                  40                  45

Leu Leu Lys Ala Gly Leu Phe Arg Cys Ala Asp Gly Asp His Leu Leu
    50                  55                  60

Leu Ala Val His His Ala Val Val Asp Gly Val Ser Trp Arg Ile Leu
65                  70                  75                  80

Met Glu Asp Phe Ala Leu Gly Tyr Glu Gln Ala Gly Lys Ser Glu Glu
                85                  90                  95

Ile Arg Phe Pro Ala Lys Thr Asp Ala Tyr Arg Thr Trp Ser Glu Gln
            100                 105                 110

Leu Ala Ala Tyr Ala Gln Ser Pro Glu Met Thr Lys Glu Arg Ala Tyr
        115                 120                 125

Trp Gln Ala Met Glu Gln Ile Ala Val Pro Ala Val Pro Lys Asp Leu
    130                 135                 140

Asp Val Asp Val Thr Thr Gln Gln Asp Ser Glu Ser Leu Phe Val Arg
145                 150                 155                 160

```
Leu Thr Pro Glu Glu Thr Glu Leu Leu Leu Lys Arg Val His Arg Ala
                165                 170                 175

Tyr Asn Thr Glu Met Asn Asp Ile Leu Val Thr Ala Leu Gly Ile Ala
                180                 185                 190

Ile Arg Lys Trp Thr Gly His Glu Arg Val Arg Ile Asn Leu Glu Gly
                195                 200                 205

His Gly Arg Glu Ser Ile Gly Thr Asp Ile Asp Ile Thr Arg Thr Val
                210                 215                 220

Gly Trp Phe Thr Thr Lys Phe Pro Val Val Leu Glu Pro Glu Thr Asp
225                 230                 235                 240

Arg Asp Leu Ala Tyr Gln Ile Lys Gln Val Lys Glu Ser Leu Arg Arg
                245                 250                 255

Ile Pro Asn Lys Gly Leu Gly Tyr Gly Val Cys Arg Tyr Leu Ser Lys
                260                 265                 270

Ser Glu Asp Gly Phe Val Trp Gly Ala Glu Pro Glu Ile Asn Phe Asn
275                 280                 285

Tyr Leu Gly Gln Phe Asp Asp Val Ser Gln Val Glu Ile Gly Ile
                290                 295                 300

Ser Ser Tyr Ser Ser Gly Ser Pro Ala Ser Asp Arg Gln Ala Arg Ser
305                 310                 315                 320

Phe Val Leu Asp Ile Asn Gly Met Val Leu Asp Gly Ala Leu Ser Leu
                325                 330                 335

Asp Leu Ser Tyr Ser Arg Lys Gln Tyr Arg Lys Glu Thr Met Glu Ala
                340                 345                 350

Phe Ala Gln Arg Leu Glu Gln Ser Leu Arg Glu Leu Ile Thr His Cys
                355                 360                 365

Ala Gly Lys Glu Asn Thr Glu Leu Thr Pro Ser Asp Val Gln Phe Lys
370                 375                 380

Gly Leu Thr Ile Ala Glu Leu Glu Gln Ile Ala Gln Arg Ser Gly His
385                 390                 395                 400

Leu Gly Glu Ile Glu Asn Ile Tyr Ser Leu Thr Pro Met Gln Lys Gly
                405                 410                 415

Met Trp Phe His Ser Ala Leu Asp Arg Gln Thr Ala Ala Tyr Phe Glu
                420                 425                 430

Gln Thr Arg Phe Thr Met Arg Gly Ala Leu Asp Val Gln Leu Phe Glu
                435                 440                 445

Arg Ser Trp Met Glu Leu Ala Lys Arg His Leu Val
450                 455                 460

<210> SEQ ID NO 13
<211> LENGTH: 9
<212> TYPE: PRT
<213> ORGANISM: Polymyxa betae

<400> SEQUENCE: 13

Leu Arg Ala Asn Phe Val Lys Gly Pro
1               5

<210> SEQ ID NO 14
<211> LENGTH: 437
<212> TYPE: PRT
<213> ORGANISM: Polymyxa betae

<400> SEQUENCE: 14

Glu Gly Glu Pro Leu Gln Val Ile Tyr Arg Asp Lys Pro Val Gly Phe
1               5                   10                  15
```

-continued

```
Glu Tyr Glu Glu Leu Leu His Leu Gln Ala Asp Glu Lys Gln Ala Tyr
             20                  25                  30
Leu Asp Lys Lys Ala Glu Asp Lys Leu Arg Gly Phe Asp Met Glu
         35                  40                  45
His Asp Ala Leu Val Arg Val Thr Ile Leu Arg Thr Glu Glu Gln Ser
     50                  55                  60
Tyr His Val Leu Trp Ser Phe Gln His Ile Leu Met Asp Gly Trp Cys
 65                  70                  75                  80
Leu Pro Gln Leu Thr Gln Glu Leu Phe Glu Met Tyr Ser Ala Leu Ala
                 85                  90                  95
Ser Gly Lys Gln Pro Ala Gly Asp Lys Gly Ser Asp Tyr Gly Ala Tyr
             100                 105                 110
Ile Glu Trp Leu Glu Lys Gln Asp Asp Gln Ala Ala Ser Gly Tyr Trp
         115                 120                 125
Thr Ala Phe Leu Ala Asp Tyr Glu Gly Gln Thr Val Leu Pro Gly Gln
    130                 135                 140
Lys Glu Pro Ala Pro Ser Gly Ile Phe Thr Ala Asp His Val Thr Ala
145                 150                 155                 160
Glu Leu Gly Lys Asp Leu Ser Glu Arg Met Asp Arg Val Ala Lys Gln
                165                 170                 175
Arg Leu Val Thr Val Asn Thr Leu Leu Gln Ala Ala Trp Gly Val Met
            180                 185                 190
Leu Gln Lys Tyr Asn Gly Thr Asn Asp Ala Val Phe Gly Ser Val Val
        195                 200                 205
Ala Gly Arg Pro Ala Glu Ile Pro Gly Ile Glu Ser Met Ile Gly Leu
    210                 215                 220
Phe Ile Asn Thr Val Pro Val Arg Val Thr Ser Glu Ala Asp Thr Val
225                 230                 235                 240
Phe Ala Asp Leu Met Ala Lys Leu Gln Glu Arg Ala Leu Glu Ser Gly
                245                 250                 255
Arg Tyr Asp Tyr Tyr Pro Leu Tyr Glu Ile Gln Ala Arg Ser Val Gln
            260                 265                 270
Lys Gln Asn Leu Ile Asn His Ile Ile Ala Phe Glu Asn Tyr Pro Val
        275                 280                 285
Asp Glu Gln Met Glu Gln Ala Gly Asp Gln His Gly Asp Leu Thr
    290                 295                 300
Ile Ala Asp Val Gln Met Glu Glu Gln Thr Asn Tyr Asn Phe Asn Val
305                 310                 315                 320
Thr Val Val Pro Gly Val Gly Ile Glu Ile Arg Phe Asp Phe Asn Ala
                325                 330                 335
Glu Val Phe Asp Lys Asp Ser Ile Glu Arg Leu Lys Gly His Leu Val
            340                 345                 350
His Leu Leu Glu Gln Val Thr Asp Asn Pro Glu Ile Thr Val Gly Glu
        355                 360                 365
Leu Glu Leu Val Thr Glu Gly Glu Lys Ala Asp Leu Leu Gly Arg Phe
    370                 375                 380
Asn Asp Thr Thr Thr Glu Phe Pro Arg Gly Lys Thr Leu Val Gln Leu
385                 390                 395                 400
Phe Glu Glu Gln Ala Glu Leu Tyr Pro Asp Asn Val Ala Ala Val Met
                405                 410                 415
Asn Glu Arg Gln Leu Thr Tyr Arg Glu Leu Asn Glu Arg Ser Asn Arg
            420                 425                 430
Leu Ala Arg Lys Leu
```

```
                            435

<210> SEQ ID NO 15
<211> LENGTH: 530
<212> TYPE: PRT
<213> ORGANISM: Polymyxa betae

<400> SEQUENCE: 15

Glu Arg Ser Asn Arg Leu Ala Arg Lys Leu Arg Glu Thr Gly Val Glu
  1               5                  10                  15

Ala Asp Gln Leu Val Ala Ile Leu Ala Glu Arg Ser Leu Asp Met Val
                 20                  25                  30

Val Gly Ile Leu Ala Ile Leu Lys Ala Gly Gly Ala Tyr Val Pro Val
             35                  40                  45

Asp Pro Asp Tyr Pro Glu Glu Arg Ile Arg Phe Met Ile Glu Asp Ser
         50                  55                  60

Gly Ala Pro Leu Leu Leu Ile Gln Lys His Leu His Glu Lys Thr Asp
 65                  70                  75                  80

Phe Ala Gly Thr Arg Leu Glu Leu Asp Asp Phe Val Trp Gly Asp Arg
                 85                  90                  95

Gly Ala Asp Ser Ala Asp Ala Leu Asp Ala Ser Asn Leu Glu Pro Ile
            100                 105                 110

Ser Gly Pro Gly Asn Leu Ala Tyr Val Ile Tyr Thr Ser Gly Thr Thr
        115                 120                 125

Gly Arg Pro Lys Gly Thr Leu Ile Glu His Lys Asn Val Val Arg Leu
    130                 135                 140

Leu Phe Asn Asp Lys Asn Leu Phe Asp Phe Gly Pro Ser Asp Thr Trp
145                 150                 155                 160

Thr Leu Phe His Ser Phe Cys Phe Asp Phe Ser Val Trp Glu Met Tyr
                165                 170                 175

Gly Ala Leu Leu Tyr Gly Gly Lys Leu Val Ile Val Pro Ser Leu Thr
            180                 185                 190

Ala Lys Asn Pro Ala Asp Phe Leu Ala Leu Leu Gly Arg Glu Gln Val
        195                 200                 205

Thr Ile Leu Asn Gln Thr Pro Thr Tyr Phe Tyr Gln Leu Leu Arg Glu
    210                 215                 220

Val Leu Ala Asp His Pro Tyr Asp Leu Arg Ile Arg Asn Val Ile Phe
225                 230                 235                 240

Gly Gly Glu Ala Leu Ser Pro Leu Leu Leu Lys Gly Phe Lys Thr Lys
                245                 250                 255

Tyr Pro Glu Thr Lys Leu Ile Asn Met Tyr Gly Ile Thr Glu Thr Thr
            260                 265                 270

Val His Val Thr Tyr Lys Glu Ile Thr Trp Val Glu Met Glu Ala Ala
        275                 280                 285

Lys Ser Asn Ile Gly Lys Pro Ile Pro Thr Leu Arg Val Tyr Val Leu
    290                 295                 300

Asp Glu Asn Arg Arg Pro Val Pro Ile Gly Val Ala Gly Glu Met Tyr
305                 310                 315                 320

Val Ala Gly Glu Gly Leu Ala Arg Gly Tyr Leu Asn Arg Pro Asp Leu
                325                 330                 335

Thr Ala Glu Lys Phe Val Asp Ser Pro Phe Ala Glu Gly Glu Lys Leu
            340                 345                 350

Tyr Arg Ser Gly Asp Leu Ala Ala Trp Leu Pro Asp Gly Asn Ile Glu
        355                 360                 365
```

-continued

```
Tyr Leu Gly Arg Ile Asp His Gln Val Lys Ile Arg Gly Tyr Arg Ile
            370                 375                 380

Glu Leu Asp Glu Ile Glu Thr Gln Leu Leu Asn Val Arg Gly Val Glu
385                 390                 395                 400

Glu Ala Val Val Leu Ala Arg Gln Asp Gly Gly Glu Lys Ala Leu
                405                 410                 415

Val Ala Tyr Phe Val Ala Asp Arg Thr Leu Thr Val Ser Glu Met Arg
                420                 425                 430

Thr Ser Leu Ala Gln Gly Met Pro Gly Tyr Met Ile Pro Ser Tyr Phe
            435                 440                 445

Val Gln Leu Glu Arg Met Pro Leu Thr Thr Asn Gly Lys Val Asp Arg
        450                 455                 460

Lys Ala Leu Pro Glu Pro Gln Gly Gly Ile Gln Thr Gly Val Glu Tyr
465                 470                 475                 480

Val Ala Pro Arg Asn Trp Thr Glu Ser Gln Leu Val Lys Ile Trp Glu
                485                 490                 495

Glu Val Leu Gly Tyr Ser Gly Ile Gly Val Leu Asp Asn Phe Phe Glu
                500                 505                 510

Leu Gly Gly His Ser Leu Arg Ala Thr Asn Leu Val Ser Lys Ile Gln
            515                 520                 525

Lys Glu
    530

<210> SEQ ID NO 16
<211> LENGTH: 20
<212> TYPE: PRT
<213> ORGANISM: Polymyxa betae

<400> SEQUENCE: 16

Met Asn Val Glu Leu Pro Leu Arg Asp Val Phe Arg Tyr Ser Thr Ile
1               5                   10                  15

Glu Glu Met Ala
            20

<210> SEQ ID NO 17
<211> LENGTH: 63
<212> TYPE: PRT
<213> ORGANISM: Polymyxa betae

<400> SEQUENCE: 17

Leu Ala Ile Ser Arg Ile Gly Glu Gln Ser Phe Ser Ser Ile Pro Leu
1               5                   10                  15

Ala Gly Ala Arg Ala Tyr Tyr Pro Leu Ser Ser Ala Gln Lys Arg Leu
                20                  25                  30

Phe Ile Leu Asn Gln Leu Glu Gly Ala Asp Gln Ser Tyr Asn Met Pro
            35                  40                  45

Gly Val Leu Leu Leu Glu Gly Ser Ile Asp Arg Ser Leu Leu Glu
        50                  55                  60

<210> SEQ ID NO 18
<211> LENGTH: 21
<212> TYPE: PRT
<213> ORGANISM: Polymyxa betae

<400> SEQUENCE: 18

Lys Ala Phe Arg Gly Leu Ile Ala Arg His Glu Thr Leu Arg Thr Gly
1               5                   10                  15

Phe Glu Ile Val Gln
```

<210> SEQ ID NO 19
<211> LENGTH: 425
<212> TYPE: PRT
<213> ORGANISM: Polymyxa betae

<400> SEQUENCE: 19

```
Gly Glu Ala Ile Gln Arg Ile Tyr Glu Ser Val Asp Phe Ala Val Glu
 1               5                  10                  15

Tyr Arg His Ala Ser Glu Glu Ala Pro Glu Val Val Gln Ala Phe
             20                  25                  30

Ile Arg Pro Phe Asp Leu Ala Lys Pro Pro Leu Leu Arg Ala Glu Leu
             35                  40                  45

Val Glu Leu Ala Ala Glu Arg Tyr Leu Leu Met Phe Asp Met His His
         50                  55                  60

Ile Val Ser Asp Gly Val Ser Met Asp Val Leu Val Glu Glu Leu Val
 65                  70                  75                  80

Arg Leu Tyr Gly Gly Glu Ser Leu Glu Pro Leu Arg Ile Gln Tyr Lys
                 85                  90                  95

Asp Tyr Ala Val Trp Gln Ser Asp Glu Gln Lys Val Gln Leu Lys
            100                 105                 110

Arg Glu Glu Ala Tyr Trp Leu Asp Arg Tyr Arg Gly Glu Leu Pro Val
        115                 120                 125

Leu Glu Met Pro Thr Asp Tyr Pro Arg Pro Ala Val Gln Ser Phe Glu
    130                 135                 140

Gly Gln Thr Leu Thr Ser Phe Val Asp Glu Ala Thr Asn Glu Gly Leu
145                 150                 155                 160

Lys Gln Leu Ala Ala Gln Arg Gly Thr Thr Leu Tyr Met Val Leu Leu
                165                 170                 175

Ala Ala Tyr Thr Val Leu Leu His Lys Tyr Thr Gly Gln Asp Asp Leu
            180                 185                 190

Ile Val Gly Thr Ser Ile Ala Gly Arg Thr His Gly Asp Thr Gln Pro
        195                 200                 205

Leu Ile Gly Met Phe Val Asn Thr Leu Ala Leu Arg Asn Tyr Pro Ala
    210                 215                 220

Ser Lys Lys Thr Phe Leu Ser Tyr Leu Glu Glu Val Lys Glu Thr Thr
225                 230                 235                 240

Leu Gly Ala Tyr Glu His Gln Asn Tyr Pro Phe Glu Glu Leu Val Asp
                245                 250                 255

Lys Val Gln Val Ser Arg Asp Leu Ser Arg Asn Pro Leu Phe Asp Thr
            260                 265                 270

Met Phe Ser Leu Gln Asn Leu Glu Asp Lys Glu Phe Glu Leu Glu Gly
        275                 280                 285

Leu Lys Leu Ser Ser Tyr Pro Ser Glu Tyr Gly Thr Ala Lys Phe Asp
    290                 295                 300

Leu Ser Val Asp Val Thr Glu Glu Asn Gly Gly Leu Glu Cys Ser Phe
305                 310                 315                 320

Glu Phe Ala Thr Ala Leu Tyr Lys Glu Ser Thr Ile Arg Arg Leu Ser
                325                 330                 335

Thr His Phe Gly His Leu Leu Ala Ala Ile Ala Ser Arg Pro Asp Ala
            340                 345                 350

Lys Ile Ala Glu Leu Asn Leu Leu Thr Ala Glu Glu Lys Glu Gln Ile
        355                 360                 365
```

Leu Gly Ala Phe Asn Pro Ala Gln Leu Glu Ala Ala Pro Ala Ala Ala
    370                 375                 380

Phe His Arg Leu Phe Glu Glu Gln Val Glu Arg Thr Pro Glu Glu Ala
385                 390                 395                 400

Ala Val Val Tyr Glu Asn Glu Arg Leu Thr Tyr Ala Glu Leu Asn Glu
                405                 410                 415

Arg Ala Asn Arg Leu Ala Ala Thr Leu
            420                 425

<210> SEQ ID NO 20
<211> LENGTH: 557
<212> TYPE: PRT
<213> ORGANISM: Polymyxa betae

<400> SEQUENCE: 20

Thr Leu Arg Ala Ser Gly Ile Gly Arg Glu Thr Ile Val Gly Ile Leu
1               5                   10                  15

Ala Glu Arg Ser Val Asp Leu Leu Val Ala Val Leu Ala Val Trp Lys
                20                  25                  30

Ala Gly Gly Ala Tyr Val Pro Leu Asp Pro Asp Tyr Pro Ala Asp Arg
            35                  40                  45

Val Arg Phe Met Leu Glu Asp Ser Gly Ala Lys Val Leu Leu Thr Gln
    50                  55                  60

Thr Ala Leu Arg Glu Arg Ala Glu Ala Trp Leu Gly Glu Glu Glu Leu
65                  70                  75                  80

Ala Leu Ala Ala Val Leu Tyr Leu Asp Asp Glu Ala Ser Tyr Asn Glu
                85                  90                  95

Glu Arg Ala Asn Ala Pro Val Gly Ser Gly Met Val Ser Gly Lys Leu
                100                 105                 110

Thr Asp Ala Val Asp Asp Gly Asp Glu Ser His Gln Asn Val Asp Thr
            115                 120                 125

Asp Gly Phe His Glu Ala Arg Pro Glu Asp Leu Ala Tyr Val Ile Tyr
    130                 135                 140

Thr Ser Gly Thr Thr Gly Lys Pro Lys Gly Val Met Ile Glu His Arg
145                 150                 155                 160

Ser Leu Val Asn Thr Ala Ala Gly Tyr Arg Arg Glu Tyr Arg Leu Asp
                165                 170                 175

Gln Phe Pro Val Arg Leu Leu Gln Leu Ala Ser Phe Ser Phe Asp Val
                180                 185                 190

Phe Val Gly Asp Ile Ala Arg Thr Leu Tyr Asn Gly Gly Thr Met Val
            195                 200                 205

Ile Val Pro Lys Asp Asp Arg Ile Asp Pro Ser Arg Leu His His Trp
    210                 215                 220

Met Glu Arg Glu Arg Val Thr Ile Phe Glu Ser Thr Pro Ala Leu Ile
225                 230                 235                 240

Val Pro Phe Leu Glu Tyr Val His Glu Gln Arg Leu Asp Met Ser Trp
                245                 250                 255

Met Glu Leu Leu Ile Thr Ser Ser Asp Ser Cys Ser Val Ala Asp Tyr
            260                 265                 270

Arg Thr Leu Gln Glu Arg Phe Gly Ser Leu Phe Arg Ile Ile Asn Ala
    275                 280                 285

Tyr Gly Val Thr Glu Ala Ala Ile Asp Ser Ser Phe Tyr Asp Glu Glu
            290                 295                 300

Leu Thr Lys Leu Pro Gln Thr Gly His Val Pro Ile Gly Lys Ala Trp
305                 310                 315                 320

```
Leu Asn Ala Lys Phe Tyr Ile Val Asp Ala His Leu Asn Pro Val Pro
                325                 330                 335

Val Gly Val Leu Gly Glu Leu Val Ile Gly Val Gly Val Ala Arg
            340                 345                 350

Gly Tyr Leu Asn Arg Pro Glu Leu Thr Glu Glu Lys Phe Val Asp Ser
                355                 360                 365

Pro Phe Ala Ala Gly Glu Arg Leu Tyr Arg Thr Gly Asp Leu Ala Arg
            370                 375                 380

Trp Met Glu Asp Gly Asn Val Asp Phe Ile Gly Arg Ile Asp Asn Gln
385                 390                 395                 400

Ala Lys Ile Arg Gly Tyr Arg Ile Glu Thr Gly Glu Ile Glu Ser Gln
                405                 410                 415

Leu Leu Arg Val Glu Gly Val Arg Glu Ala Val Val Leu Val Arg Ser
            420                 425                 430

Asp Ala Asn Gly Gln Lys Ala Leu Cys Ala Tyr Tyr Thr Pro Asp Thr
                435                 440                 445

Gly Ala Glu Leu Ala Val Asn Asp Leu Arg Gly Ala Leu Ala Gln Glu
            450                 455                 460

Leu Pro Gly Tyr Met Ile Pro Ser Tyr Phe Val Glu Leu Glu Arg Leu
465                 470                 475                 480

Pro Leu Thr Pro Asn Gly Lys Ile Asp Arg Lys Ala Leu Pro Ala Pro
                485                 490                 495

Glu Arg Glu Ala Gly Ser Gly Thr Glu Tyr Val Ala Pro Arg Asn Glu
            500                 505                 510

Leu Glu Thr Lys Leu Thr Ala Ile Trp Gln Glu Val Leu Gly Leu Ala
                515                 520                 525

Lys Glu Ile Gly Val His Asp Asn Phe Phe Asp Ile Gly Gly His Ser
            530                 535                 540

Leu Arg Ala Thr Thr Leu Val Ser Lys Ile His Lys Glu
545                 550                 555

<210> SEQ ID NO 21
<211> LENGTH: 18
<212> TYPE: PRT
<213> ORGANISM: Polymyxa betae

<400> SEQUENCE: 21

Leu Asn Val Asp Leu Pro Leu Arg Asp Val Phe Arg His Ser Thr Ile
1               5                   10                  15

Glu Ser

<210> SEQ ID NO 22
<211> LENGTH: 65
<212> TYPE: PRT
<213> ORGANISM: Polymyxa betae

<400> SEQUENCE: 22

Met Ala Ala Ala Ile Ser Arg Leu Asp Glu Gln Thr Phe Val Ala Ile
1               5                   10                  15

Pro Val Ala Asp Asp Arg Glu Val Tyr Pro Gln Ser Phe Ala Gln Lys
                20                  25                  30

Arg Leu Phe Ile Leu Asn Gln Leu Glu Gly Ala Glu Leu Ser Tyr Asn
            35                  40                  45

Met Pro Glu Ala Met Leu Leu Glu Gly Ala Leu Asp Arg Thr Arg Phe
    50                  55                  60
```

Glu
65

<210> SEQ ID NO 23
<211> LENGTH: 22
<212> TYPE: PRT
<213> ORGANISM: Polymyxa betae

<400> SEQUENCE: 23

Glu Ala Phe Arg Lys Leu Val Ala Arg His Glu Thr Leu Arg Thr Gly
1               5                   10                  15

Phe Glu Met Val Asp Gly
            20

<210> SEQ ID NO 24
<211> LENGTH: 424
<212> TYPE: PRT
<213> ORGANISM: Polymyxa betae

<400> SEQUENCE: 24

Glu Ala Ser Gln Arg Ile Tyr Gln Asp Val Asn Phe Ala Val Glu Phe
1               5                   10                  15

Tyr Arg Val Asp Glu Gln Ala Glu Glu Thr Val His Arg Phe Val
            20                  25                  30

Arg Pro Phe Asp Leu Ala Lys Pro Pro Leu Arg Val Gly Leu Val
            35                  40                  45

Glu Leu Ala Pro Glu Arg His Ile Leu Met Tyr Asp Met His His Ile
    50                  55                  60

Ile Ser Asp Gly Val Ser Met Glu Ile Phe Val Glu Glu Phe Val Arg
65                  70                  75                  80

Leu Tyr Gly Gly Glu Gln Leu Glu Pro Leu Arg Ile Gln Tyr Lys Asp
                85                  90                  95

Tyr Thr Val Trp Gln His Ser Gln Glu Gln Lys Glu Arg Leu Gln Arg
            100                 105                 110

Gln Glu Ala Tyr Trp Leu Asp Met Phe Gln Gly Glu Leu Pro Val Leu
        115                 120                 125

Glu Met Pro Thr Asp Tyr Pro Arg Pro Ala Val Gln Ser Tyr Glu Gly
    130                 135                 140

Gln Thr Leu Glu Phe Phe Phe Asp Ala Ser Lys Thr Asp Gly Leu Lys
145                 150                 155                 160

Gln Leu Ala Ser Glu Thr Gly Thr Thr Leu Phe Met Val Leu Leu Ala
                165                 170                 175

Ala Tyr Asn Val Leu Leu His Lys Tyr Ser Gly Gln Glu Asp Val Ile
            180                 185                 190

Val Gly Thr Pro Ile Ala Gly Arg Asn His Gly Asp Val Gln Pro Leu
        195                 200                 205

Ile Gly Ile Phe Leu Asn Thr Leu Ala Ile Arg Ser Tyr Pro Ala Ser
    210                 215                 220

Glu Lys Thr Phe Leu Ser Tyr Leu Asn Glu Val Lys Glu Thr Thr Leu
225                 230                 235                 240

His Ala Phe Glu His Gln Asn Tyr Pro Phe Glu Glu Leu Val Asp Lys
                245                 250                 255

Val Gln Val Thr Arg Asp Leu Ser Arg Asn Pro Leu Phe Asp Thr Leu
            260                 265                 270

Phe Thr Met Gln Asn Thr Glu Asn Glu Glu Phe Glu Leu Glu Gly Leu
        275                 280                 285

```
Arg Leu Ile Pro Tyr Pro Ser Ala Leu Asp Thr Ala Lys Phe Asp Ile
    290                 295                 300

Ser Leu Asp Val Gly Glu Glu Asn Gly Gly Leu Asp Tyr Ser Phe Glu
305                 310                 315                 320

Tyr Ala Thr Ala Leu Tyr Lys Arg Glu Thr Ile Glu Arg Leu Ala Lys
                325                 330                 335

His Tyr Glu Gln Leu Leu Val Thr Ile Val Ser Arg Pro Asp Ala Lys
            340                 345                 350

Ile Ala Glu Leu Asn Leu Leu Thr Ala Glu Glu Lys Gly Gln Ile Leu
        355                 360                 365

Gly Ala Phe His Pro Ala Gln Leu Glu Ala Ala Pro Ala Ala Ala Phe
    370                 375                 380

His Arg Leu Phe Glu Glu Gln Ala Glu Arg Thr Pro Glu Ala Val Ala
385                 390                 395                 400

Val Val Tyr Glu Asn Asp Arg Leu Thr Tyr Ala Glu Leu Asn Glu Arg
                405                 410                 415

Ala Asn Arg Leu Ala Ala Thr Leu
            420

<210> SEQ ID NO 25
<211> LENGTH: 19
<212> TYPE: PRT
<213> ORGANISM: Polymyxa betae

<400> SEQUENCE: 25

Arg Ala Ser Gly Ile Gly Arg Glu Thr Ile Val Gly Ile Leu Ala Glu
1               5                   10                  15

Arg Ser Val

<210> SEQ ID NO 26
<211> LENGTH: 509
<212> TYPE: PRT
<213> ORGANISM: Polymyxa betae

<400> SEQUENCE: 26

Asp Leu Leu Val Ala Val Leu Ala Val Trp Lys Ala Gly Gly Ala Tyr
1               5                   10                  15

Val Pro Leu Asp Pro Asp Tyr Pro Ala Glu Arg Val Arg Phe Met Leu
            20                  25                  30

Glu Asp Ser Gly Ala Lys Val Leu Leu Thr Gln Thr Pro Leu Arg Glu
        35                  40                  45

Arg Ala Lys Ala Trp Leu Gly Glu Glu Leu Ala Leu Ala Ala Val
    50                  55                  60

Leu Tyr Leu Asp Asp Glu Ala Ser Tyr Ser Glu Glu Arg Ala Asn Ala
65                  70                  75                  80

Asp Ser Phe His Glu Ala Arg Pro Glu Asp Leu Ala Tyr Val Ile Tyr
                85                  90                  95

Thr Ser Gly Thr Thr Gly Lys Pro Lys Gly Val Met Ile Glu His Arg
            100                 105                 110

Ser Leu Val Asn Thr Ala Ala Ser Tyr Arg Arg Glu Tyr Arg Leu Asp
        115                 120                 125

Gln Phe Pro Val Arg Leu Leu Gln Leu Ala Ser Phe Ser Phe Asp Val
    130                 135                 140

Phe Val Gly Asp Ile Ala Arg Thr Leu Tyr Asn Gly Gly Thr Met Val
145                 150                 155                 160

Ile Val Pro Lys Asp Asp Arg Ile Asp Pro Ser Arg Leu His Tyr Trp
```

```
                    165                 170                 175
Met Glu Arg Glu Gln Val Thr Ile Phe Glu Ser Thr Pro Ala Leu Ile
                180                 185                 190

Val Pro Phe Met Glu Tyr Val His Glu Gln Gly Leu Asp Met Ser Trp
            195                 200                 205

Met Glu Leu Leu Ile Thr Ser Ser Asp Ser Cys Ser Val Ala Asp Tyr
        210                 215                 220

Arg Thr Leu Gln Glu Arg Phe Gly Ser Leu Phe Arg Ile Ile Asn Ala
225                 230                 235                 240

Tyr Gly Val Thr Glu Ala Ala Ile Asp Ser Ser Phe Tyr Asp Glu Glu
                245                 250                 255

Leu Ala Lys Leu Pro Gln Thr Gly His Val Pro Ile Gly Lys Ala Trp
            260                 265                 270

Leu Asn Ala Lys Phe Tyr Ile Val Asp Ala His Leu Asn Pro Val Pro
        275                 280                 285

Val Gly Val Leu Gly Glu Leu Val Ile Gly Val Gly Val Ala Arg
                290                 295                 300

Gly Tyr Leu Asn Arg Pro Glu Leu Thr Gly Glu Lys Phe Val Asp Ser
305                 310                 315                 320

Pro Phe Ala Ala Gly Glu Arg Leu Tyr Arg Thr Gly Asp Leu Ala Arg
                325                 330                 335

Trp Met Glu Asp Gly Asn Val Asp Phe Ile Gly Arg Ile Asp Asn Gln
            340                 345                 350

Ala Lys Ile Arg Gly Tyr Arg Ile Glu Thr Gly Glu Ile Glu Ser Gln
        355                 360                 365

Leu Leu Gln Val Glu Gly Val Arg Glu Ala Val Val Leu Val Arg Ser
    370                 375                 380

Asp Ala Asn Gly Gln Lys Ala Leu Cys Ala Tyr Tyr Thr Pro Asp Thr
385                 390                 395                 400

Gly Ala Glu Leu Ala Val Asn Asp Leu Arg Gly Ala Leu Ala Gln Glu
                405                 410                 415

Leu Pro Gly Tyr Met Ile Pro Ser Tyr Phe Val Glu Met Glu Arg Leu
            420                 425                 430

Pro Leu Thr Pro Asn Gly Lys Ile Asp Arg Lys Ala Leu Pro Ala Pro
        435                 440                 445

Glu Gly Glu Ala Gly Ser Gly Thr Glu Tyr Val Ala Pro Arg Asn Glu
    450                 455                 460

Leu Glu Thr Lys Leu Thr Ala Ile Trp Gln Glu Val Leu Gly Leu Ala
465                 470                 475                 480

Lys Glu Ile Gly Val His Asp Asn Phe Phe Asp Ile Gly Gly His Ser
                485                 490                 495

Leu Arg Ala Thr Thr Leu Ala Gly Lys Val Phe Lys Glu
            500                 505

<210> SEQ ID NO 27
<211> LENGTH: 18
<212> TYPE: PRT
<213> ORGANISM: Polymyxa betae

<400> SEQUENCE: 27

Leu Asn Val Asn Leu Pro Leu Arg Asp Val Phe Arg His Ser Thr Ile
  1               5                  10                  15

Ala Ala
```

<210> SEQ ID NO 28
<211> LENGTH: 65
<212> TYPE: PRT
<213> ORGANISM: Polymyxa betae

<400> SEQUENCE: 28

```
Met Ala Glu Ala Ile Ala Arg Met Glu Arg Arg Glu His Glu Ala Ile
 1               5                  10                  15

Pro Gln Ala Glu Glu Arg Glu Tyr Tyr Pro Leu Ser Ser Ala Gln Lys
            20                  25                  30

Arg Leu Phe Ile Gln His Thr Leu Asp Gly Ala Asp Gln Leu Tyr Asn
        35                  40                  45

Met Pro Glu Leu Val Gln Val Glu Gly Glu Phe Asp Leu Glu Arg Leu
    50                  55                  60

Glu
 65
```

<210> SEQ ID NO 29
<211> LENGTH: 21
<212> TYPE: PRT
<213> ORGANISM: Polymyxa betae

<400> SEQUENCE: 29

```
Ala Ala Leu Arg Lys Leu Ile Thr Arg His Glu Ser Leu Arg Thr Gly
 1               5                  10                  15

Phe Glu Ile Val Lys
            20
```

<210> SEQ ID NO 30
<211> LENGTH: 381
<212> TYPE: PRT
<213> ORGANISM: Polymyxa betae

<400> SEQUENCE: 30

```
Gly Glu Ala Val Gln Arg Ile Tyr Pro Gln Val Asp Phe Ala Ile Glu
 1               5                  10                  15

His Tyr Gln Ala Asp Lys Glu Asp Ala Ala Gln Ile Glu Gln Ile Val
            20                  25                  30

Arg Ser Phe Val Arg Pro Phe Asp Leu Gly Lys Pro Pro Leu Leu Arg
        35                  40                  45

Ala Gly Val Ile Glu Leu Glu Pro Asn Leu His Ile Leu Leu Phe Asp
    50                  55                  60

Met His His Met Val Ser Asp Gly Val Ser Met Ala Ile Val Ile Asp
 65                  70                  75                  80

Glu Phe Ser Ser Phe Tyr Ala Gly Glu Glu Leu Pro Pro Leu Arg Ile
                85                  90                  95

Gln Tyr Lys Asp Tyr Ala Val Trp Gln Gln Ser Lys Ala His Arg Glu
            100                 105                 110

Arg Ile Gly Arg Gln Glu Ala Tyr Trp Leu Gln Thr Phe Glu Gly Glu
        115                 120                 125

Leu Pro Thr Ala Asp Leu Pro Met Asp Tyr Glu Arg Ser Ala Ala Arg
    130                 135                 140

Ser Tyr Glu Gly Ala His Leu Glu Phe Asp Val Glu Ala Ser Leu Ser
145                 150                 155                 160

Ala Gln Leu Arg Glu Leu Ala Ala Glu Arg Glu Ser Thr Leu Phe Met
                165                 170                 175

Val Leu Leu Ala Ala Tyr Thr Val Leu Leu Ser Lys Tyr Ser Gly Gln
            180                 185                 190
```

```
Glu Asp Leu Val Val Gly Thr Pro Val Ala Gly Arg Thr Asn Ala Asp
        195                 200                 205

Leu Glu Pro Ile Ile Gly Met Phe Val Asn Thr Leu Ala Ile Arg Asn
    210                 215                 220

Arg Pro Ser Gly Asp Lys Thr Phe Leu Ser Tyr Leu Glu Glu Val Lys
225                 230                 235                 240

Glu Thr Ala Leu Gly Ala Phe Glu Asn Gln Asp Tyr Pro Phe Glu Glu
                245                 250                 255

Leu Val Glu Arg Leu Asn Val Lys Arg Glu Pro Gly Arg Phe Pro Leu
            260                 265                 270

Phe Asp Ala Val Phe Asp Leu Gln Asn Ile Glu Glu Arg Asp Ala Glu
        275                 280                 285

Leu Glu Gly Val Ser Leu Lys Thr Tyr Glu Leu Asp His Leu Glu Glu
    290                 295                 300

Ala Lys Phe Asp Leu Thr Leu Phe Met Tyr Glu Asn Asn Gly Ala Leu
305                 310                 315                 320

Ser Gly Gly Phe Phe Tyr Ala Thr Lys Leu Phe Lys Glu Ala Met Ile
                325                 330                 335

Arg Thr Leu Thr Glu Asp Tyr Leu Arg Val Leu Ser Gln Ile Ala Lys
            340                 345                 350

Asn Pro Gln Leu Glu Leu Ser Arg Ile Glu Cys His Lys Pro Ala Ala
        355                 360                 365

Gly Ala Lys Ser Ala Val Asp Thr Ile Glu Phe Ala Phe
    370                 375                 380

<210> SEQ ID NO 31
<211> LENGTH: 300
<212> TYPE: PRT
<213> ORGANISM: Polymyxa betae

<400> SEQUENCE: 31

Met Lys Ser Leu Phe Glu Lys Glu Gln Tyr Trp Ser Gly Lys Phe
1               5                   10                  15

Asp Ala Asp Ser Leu Ser Phe Leu Pro Tyr Ser Gln Ser Ser Lys
            20                  25                  30

Leu Ser Ala His Gly Glu Ala Ala Glu Pro Gly Leu Leu His Arg
        35                  40                  45

Thr Leu Pro Ser Gln Leu Ser Glu Arg Ile Ile Ser Leu Ala Asn Gly
    50                  55                  60

Ser Asp Leu Ala Leu Tyr Met Ile Val Leu Ala Gly Val Lys Ser Leu
65                  70                  75                  80

Leu Phe Lys Tyr Thr Gly Arg Asp Gln Val Leu Val Gly Met Pro Ser
                85                  90                  95

Tyr Ser Ala Asp Pro Asp Gly Thr Pro Pro His Asp Ile Leu Val
            100                 105                 110

Ile Lys Thr Ser Val Ser Arg Gln Thr Thr Leu Lys Thr Leu Leu Gly
        115                 120                 125

Gly Ile Lys Ala Ser Ile Gly Glu Ala Leu Glu His Gln His Leu Pro
    130                 135                 140

Phe Arg Lys Met Val Glu Pro Leu His Leu Asp Tyr Thr Gly Asp Gly
145                 150                 155                 160

Leu Pro Val Val Asn Thr Val Ser Phe Ala Pro Ile His Pro Glu
                165                 170                 175

Pro Gln Gly Asn Arg Val Ala Ala Asp Thr Val Phe Arg Phe Asp Arg
```

```
                    180                 185                 190
Gln Asn His Ser Ile Glu Leu Glu Ile Ser Phe Asp Gly Gln Arg Tyr
            195                 200                 205

Glu Arg Ala Phe Val Glu Gln Ala Ala Asp His Leu Val Arg Leu Leu
        210                 215                 220

Ser Val Leu Leu Phe Gln Pro Asp Leu Lys Leu Gly Gln Ala Asp Val
225                 230                 235                 240

Leu Ser Pro Asp Glu Arg Glu Thr Leu Leu Lys Arg Phe Asn Asp Thr
                245                 250                 255

Glu Thr Glu Phe Glu Arg Gly Lys Thr Ile Tyr Gly Leu Phe Glu Glu
            260                 265                 270

Gln Ala Glu Leu Tyr Pro Asp Asn Val Ala Ala Val Met Asn Glu Arg
        275                 280                 285

Gln Leu Thr Tyr Arg Glu Leu Asn Glu Arg Ser Asn
    290                 295                 300

<210> SEQ ID NO 32
<211> LENGTH: 530
<212> TYPE: PRT
<213> ORGANISM: Polymyxa betae

<400> SEQUENCE: 32

Arg Leu Ala Arg Lys Leu Arg Glu Ala Gly Val Glu Ala Asp Gln Leu
1               5                   10                  15

Val Ala Ile Leu Ala Glu Arg Ser Leu Asp Met Val Val Gly Ile Leu
            20                  25                  30

Ala Ile Leu Lys Ala Gly Gly Ala Tyr Val Pro Val Asp Pro Asp Tyr
        35                  40                  45

Pro Glu Glu Arg Ile Arg Phe Met Ile Glu Asp Ser Gly Ala Pro Leu
    50                  55                  60

Leu Leu Ile Gln Lys His Leu His Glu Lys Thr Asp Phe Ala Gly Thr
65                  70                  75                  80

Arg Leu Glu Leu Asp Asp Phe Val Trp Gly Asp Arg Gly Ala Asn Ser
                85                  90                  95

Ala Glu Ala Leu Asp Ala Ser Asn Leu Glu Pro Ile Ser Gly Pro Gly
            100                 105                 110

Asn Leu Ala Tyr Val Ile Tyr Thr Ser Gly Thr Thr Gly Arg Pro Lys
        115                 120                 125

Gly Thr Leu Ile Glu His Lys Asn Val Val Arg Leu Leu Phe Asn Asp
    130                 135                 140

Lys Asn Leu Phe Asp Phe Gly Pro Ser Asp Thr Trp Thr Leu Phe His
145                 150                 155                 160

Ser Phe Cys Phe Asp Phe Ser Val Trp Glu Met Tyr Gly Ala Leu Leu
                165                 170                 175

Tyr Gly Gly Lys Leu Val Ile Val Pro Pro Leu Thr Ala Lys Asn Pro
            180                 185                 190

Ala Asp Phe Leu Ala Leu Leu Gly Arg Glu Gln Val Thr Ile Leu Asn
        195                 200                 205

Gln Thr Pro Thr Tyr Phe Tyr Gln Leu Leu Arg Lys Val Leu Ala Asp
    210                 215                 220

His Pro Tyr Asp Leu Arg Ile Arg Asn Val Ile Phe Gly Gly Glu Ala
225                 230                 235                 240

Leu Ser Pro Leu Leu Leu Lys Gly Phe Lys Thr Lys Tyr Pro Glu Thr
                245                 250                 255
```

```
Lys Leu Ile Asn Met Tyr Gly Ile Thr Glu Thr Thr Val His Val Thr
            260                 265                 270

Tyr Lys Glu Ile Thr Trp Val Glu Met Glu Ala Ala Lys Ser Asn Ile
        275                 280                 285

Gly Lys Pro Ile Pro Thr Leu Arg Val Tyr Val Leu Asp Glu Asn Arg
    290                 295                 300

Arg Leu Val Pro Ile Gly Val Ala Gly Glu Met Tyr Val Ala Gly Glu
305                 310                 315                 320

Gly Leu Ala Arg Gly Tyr Leu Asn Arg Pro Asp Leu Thr Ala Glu Lys
                325                 330                 335

Phe Val Asp Ser Pro Phe Ala Glu Gly Arg Leu Tyr Arg Ser Gly
            340                 345                 350

Asp Leu Ala Ala Trp Leu Pro Asp Gly Asn Ile Glu Tyr Leu Gly Arg
        355                 360                 365

Ile Asp His Gln Val Lys Ile Arg Gly Tyr Arg Ile Glu Leu Asp Glu
    370                 375                 380

Ile Glu Thr Gln Leu Leu Asn Ala Arg Gly Val Glu Ala Val Val
385                 390                 395                 400

Leu Ala Arg Asp Asp Ala His Gly His Lys Gln Leu Val Ala Tyr Tyr
                405                 410                 415

Val Ala Glu Thr Arg Leu Ala Ala Asn Glu Leu Lys Glu Glu Leu Ala
            420                 425                 430

Lys Gln Leu Pro Gly Tyr Met Ile Pro Ser His Leu Val Gln Leu Ser
        435                 440                 445

Arg Met Pro Leu Thr Pro Asn Gly Lys Ile Asp Arg Lys Ala Leu Pro
    450                 455                 460

Ala Pro Glu Glu Ala Ala Gly Gly Ala Glu Tyr Val Ala Pro Arg
465                 470                 475                 480

Thr Leu Leu Glu Met Lys Ile Val Arg Val Trp Gln Asp Thr Leu Gly
                485                 490                 495

Val Pro Gln Val Gly Val Lys Asp Asn Phe Phe Glu Leu Gly Gly Asn
            500                 505                 510

Ser Leu Ser Leu Met Arg Leu Val Gln Ala Val Tyr Asp Glu Thr Gly
        515                 520                 525

Ile Glu
    530

<210> SEQ ID NO 33
<211> LENGTH: 14
<212> TYPE: PRT
<213> ORGANISM: Polymyxa betae

<400> SEQUENCE: 33

Ile Pro Leu Asn Arg Gln Phe His Asn Val Thr Val Glu Ala
1               5                   10

<210> SEQ ID NO 34
<211> LENGTH: 62
<212> TYPE: PRT
<213> ORGANISM: Polymyxa betae

<400> SEQUENCE: 34

Met Ala Phe Gly Glu Gly Asp Leu Gly Leu Asp Lys Gly Gly Asp Ser
1               5                   10                  15

Phe Ile Lys Leu Asn Lys Ala Gly Asp Leu Asn Val Phe Cys Phe Pro
            20                  25                  30
```

```
Pro Gly Ser Gly Phe Gly Ile Gly Tyr Arg Glu Leu Ala Ser Arg Leu
            35                  40                  45

Asp Gly Arg Phe Val Leu Tyr Gly Ile Asp Phe Ile Asp Asp
 50                  55                  60
```

<210> SEQ ID NO 35
<211> LENGTH: 25
<212> TYPE: PRT
<213> ORGANISM: Polymyxa betae

<400> SEQUENCE: 35

```
Ala Ala Asp Tyr Glu Ala Met Leu Asn Arg Tyr Val Asp Glu Ile Val
  1               5                  10                  15

Arg Ile Gln Pro Glu Gly Pro Tyr Val
             20                  25
```

<210> SEQ ID NO 36
<211> LENGTH: 171
<212> TYPE: PRT
<213> ORGANISM: Polymyxa betae

<400> SEQUENCE: 36

```
Leu Leu Gly Tyr Cys Phe Gly Gly Asn Leu Met Phe Glu Val Ala Lys
  1               5                  10                  15

Thr Met Glu Lys Arg Glu Tyr Ser Val Thr Asp Val Leu Met Val Asp
             20                  25                  30

Ser Trp Ile Lys Asp Thr Leu Thr Pro Ser Glu Thr Ser Glu Lys Glu
         35                  40                  45

Leu Glu Glu Thr Leu Ala Asp Phe Asp Glu Glu Lys Glu Leu Met
 50                  55                  60

Ser Asn Pro Leu Val Arg Glu Arg Val His Arg Lys Val Lys Ala Thr
 65                  70                  75                  80

Leu Ala Tyr Glu Ala Gln Leu Met Asn Ser Gly Thr Ile Pro Ala Arg
                 85                  90                  95

Ile Tyr Glu Leu Ile Ala Lys Asp Ser Glu Ala Phe Arg Leu Glu His
            100                 105                 110

Gln Leu Pro Ser Trp Arg Gly Ala Thr Thr Gln Ala Tyr Ala Asp Tyr
        115                 120                 125

Arg Leu Glu Gly Ala His Glu Glu Leu Leu Glu Leu Ala Arg Val Asp
    130                 135                 140

Glu Thr Ala Val Val Ile Arg Asp Ile Leu Glu Gln Val Lys Arg Gln
145                 150                 155                 160

Ile Glu Ala Glu Ala Gly Val Leu His Gly Ser
                165                 170
```

<210> SEQ ID NO 37
<211> LENGTH: 70
<212> TYPE: PRT
<213> ORGANISM: Polymyxa betae

<400> SEQUENCE: 37

```
Met Arg Glu Asn Thr Lys Glu Gln Tyr Gly Leu Thr Gln Ala Gln Arg
  1               5                  10                  15

Arg Ile Trp Phe Met Glu Ile Met Asn Pro Gly Thr Ser Ile Thr Met
             20                  25                  30

Leu Ser Ala Thr Tyr Gln Ile Thr Gly Glu Ile Asn Thr Gln Leu Leu
         35                  40                  45

Glu Gln Ala Ala Ala Glu Ile Val Lys Thr Tyr Asp Val Phe Arg Ile
```

50                  55                  60
Arg Ile Ser Gly Asp Leu
 65                  70

<210> SEQ ID NO 38
<211> LENGTH: 432
<212> TYPE: PRT
<213> ORGANISM: Polymyxa betae

<400> SEQUENCE: 38

Gln Asn Pro Thr Gln Trp Phe Glu Glu Pro Glu Asn Val Gln Ala Arg
 1               5                  10                  15

Ile Ser Arg Leu Glu Ile Gly Thr Thr Glu Gln Phe Tyr Ala Trp Val
                20                  25                  30

Lys Glu Val Ser Glu Lys Pro Ala Ser Val Phe Asp Glu His Leu His
            35                  40                  45

Gln Phe Thr Ile Ile His Phe Val Asn Gly Gln Val Trp Leu Asn Leu
        50                  55                  60

Thr Val Asn His Ile Ile Ala Asp Gly Leu Ser Val Asn Ala Leu Leu
 65                  70                  75                  80

His Ala Val Met Glu Lys Tyr Leu Glu Leu Arg Lys Gly Ile Ser Ser
                85                  90                  95

Ser Tyr Gln Ala Pro Ser Tyr Leu Asp Tyr Ile Ser Ala Glu Arg Glu
            100                 105                 110

Tyr Glu Gln Ser Gln Arg Tyr Gln Lys Gly Lys Glu Tyr Trp Leu Thr
        115                 120                 125

Lys Tyr Asn Thr Leu Pro Glu Thr Thr Gly Ile Lys Ser Tyr Pro Pro
130                 135                 140

Phe Ser Ile Gly Ser Glu Ser Asn Lys Leu Ser Ile Thr Leu Asp Gly
145                 150                 155                 160

Ser Arg Tyr Glu Arg Ile Leu Thr Phe Ser Glu Gln Tyr Gln Val Ser
                165                 170                 175

Leu Tyr Thr Leu Phe Leu Ser Ala Met Tyr Ala Leu Leu Tyr Lys Leu
            180                 185                 190

Thr Asp Ser Ile Asp Val Pro Val Gly Thr Val Phe Ala Asn Arg Thr
        195                 200                 205

Ser Lys Lys Glu Lys Glu Thr Ile Gly Met Phe Val Ser Thr Val Ala
        210                 215                 220

Thr Arg Ile Arg Leu Asn Pro Asp Arg Asn Val Leu Ser Leu Ile Gln
225                 230                 235                 240

Thr Val Ser Lys Glu Asn Thr Ala Asp Leu Arg Tyr Gln Lys Tyr Pro
                245                 250                 255

Tyr Asn Gln Leu Ile Gln Asp Leu Arg Glu Gln His Gly Arg Asn Asp
            260                 265                 270

Leu Ser Gly Leu Phe Arg Thr Ser Leu Glu Tyr Leu Pro Leu Lys Ile
        275                 280                 285

Val Glu Tyr Glu Glu Ile Lys Val Arg Leu Glu Ala His Phe Ala Arg
    290                 295                 300

His Glu Met Asp Asp Leu Leu Leu Arg Phe Asp His Met Leu Asn Glu
305                 310                 315                 320

Gly His Val Ile Leu His Ala Ser Tyr Arg Thr Gly Leu Phe Glu Thr
                325                 330                 335

Ala Glu Ile Asp Arg Ile Met Glu Gln Tyr Val Thr Val Leu Asp Gln
            340                 345                 350

Phe Leu Gln Thr Pro Glu Leu Pro Ile Arg Glu Ile Ser Leu Leu Ser
                355                 360                 365

Asp Glu Glu Arg His Arg Ile Leu Asn Val Phe Asn Pro Pro Val Ala
            370                 375                 380

Gly Leu Ser Glu Gly Ala Phe His Arg Tyr Val Glu Lys Phe Ala
385                 390                 395                 400

Arg Glu Ile Pro Asp His Pro Ala Val Val Tyr Met Asp Lys Gln Leu
                405                 410                 415

Thr Tyr Gly Glu Leu Asn Glu Arg Ala Glu Arg Leu Ala Ser Leu Leu
            420                 425                 430

<210> SEQ ID NO 39
<211> LENGTH: 535
<212> TYPE: PRT
<213> ORGANISM: Polymyxa betae

<400> SEQUENCE: 39

Leu Ala Ser Leu Leu Arg Glu Gln Gly Val Gly Lys Glu Thr Ile Thr
1               5                   10                  15

Gly Ile Trp Ala Glu Arg Ser Val Glu Leu Leu Val Gly Val Leu Ala
            20                  25                  30

Val Trp Lys Ala Gly Gly Ala Tyr Val Pro Leu Asp Pro Asp Tyr Pro
        35                  40                  45

Ala Glu Arg Ile Glu Tyr Met Leu Ser Asp Ser Asp Ala Ser Val Leu
    50                  55                  60

Leu Thr Gln Arg His Leu Leu Glu Arg Ala Gly Gly Trp Leu Ala Asp
65                  70                  75                  80

Asp Arg Leu Lys Leu Gln Ala Val Tyr Ala Met Asp Asp Glu Gln Ile
                85                  90                  95

Tyr Asn Gly Asp Ala Leu Ala Val Glu Phe Glu Ser Ala Gly Ser Ala
            100                 105                 110

Pro Gln Asp Leu Ala Tyr Val Ile Tyr Thr Ser Gly Thr Thr Gly Arg
        115                 120                 125

Pro Lys Gly Val Met Ile Glu His Gly Ser Leu Val Asn Thr Ala Asp
    130                 135                 140

Ala Tyr Arg Arg Glu Tyr Arg Leu Asp Gln Phe Pro Val Arg Leu Leu
145                 150                 155                 160

Gln Leu Ala Ser Phe Ser Phe Asp Val Phe Val Gly Asp Ile Ala Arg
                165                 170                 175

Thr Leu Tyr Asn Gly Gly Thr Met Val Ile Val Pro Lys Asp Asp Arg
            180                 185                 190

Ile Asp Pro Asn Leu Leu Tyr Gly Trp Ile Arg Asp Gln Asn Ile Thr
        195                 200                 205

Val Phe Glu Ser Thr Pro Ala Leu Ile Leu Pro Phe Met Gln His Ile
    210                 215                 220

Tyr Glu Glu Gly Leu Asp Val Ser Ser Met Gln Leu Leu Ile Thr Ser
225                 230                 235                 240

Ser Asp Ala Cys Ser Val Thr Asp Tyr Arg Leu Leu Gln Glu Arg Phe
                245                 250                 255

Gly Gly Gln Phe Arg Ile Ile Asn Ser Tyr Gly Val Thr Glu Ala Ala
            260                 265                 270

Ile Asp Ser Ser Phe Tyr Gly Glu Pro Leu Asp Lys Leu Pro Pro Ser
        275                 280                 285

Gly His Val Pro Ile Gly Lys Ala Trp Leu Asn Ala Arg Phe Tyr Ile
    290                 295                 300

```
Val Asp Ala Ala Leu Lys Pro Val Pro Val Gly Val Pro Gly Glu Leu
305                 310                 315                 320

Val Ile Gly Gly Ala Gly Val Ala Arg Gly Tyr Trp Asn Arg Pro Asp
            325                 330                 335

Leu Thr Ala Glu Lys Phe Ala Asp Ser Pro Phe Val Pro Gly Glu Arg
                340                 345                 350

Leu Tyr Arg Thr Gly Asp Leu Ala Arg Trp Leu Glu Asp Gly Asn Val
            355                 360                 365

Asp Phe Ile Gly Arg Ile Asp Tyr Gln Val Lys Ile Arg Gly Phe Arg
    370                 375                 380

Ile Glu Leu Gly Glu Ile Glu Thr Ala Leu Leu Arg Phe Pro Gly Val
385                 390                 395                 400

Lys Gln Ala Val Val Thr Asp Arg Thr Asp Glu Gln Gly Glu Lys Tyr
                405                 410                 415

Leu Cys Gly Tyr Val Ala Ala Asp Ala Ser Leu Gln Leu Ser Asp Leu
            420                 425                 430

Leu Ser Gln Leu Lys Gln Glu Leu Pro Ala His Met Val Pro Ala Arg
        435                 440                 445

Leu Val Ser Leu Asp Lys Leu Pro Leu Thr Pro Asn Gly Lys Ile Asp
    450                 455                 460

Arg Lys Ala Leu Pro Glu Pro Thr Gly Val Glu Ala Gly Arg Glu
465                 470                 475                 480

Tyr Val Ala Pro Arg Thr Thr Leu Glu Thr Arg Leu Ala Leu Ile Trp
            485                 490                 495

Gln Gln Val Leu Gly Ile Ala Arg Val Gly Val Gln Asp Asp Phe Phe
                500                 505                 510

Asp Leu Gly Gly His Ser Leu Arg Ala Ser Thr Leu Val Ser Lys Ile
            515                 520                 525

Arg Lys Glu Leu Gln Val Glu
    530                 535

<210> SEQ ID NO 40
<211> LENGTH: 15
<212> TYPE: PRT
<213> ORGANISM: Polymyxa betae

<400> SEQUENCE: 40

Val Pro Leu Arg Glu Val Phe Arg Tyr Thr Thr Ile Glu Gln Leu
1               5                   10                  15

<210> SEQ ID NO 41
<211> LENGTH: 64
<212> TYPE: PRT
<213> ORGANISM: Polymyxa betae

<400> SEQUENCE: 41

Ala Gln Arg Ile Gly Gly Leu Arg Gln Gln Glu Thr Tyr Glu Ile Thr
1               5                   10                  15

Lys Ala Ala Glu Ala Glu Tyr Tyr Pro Val Ser Ser Glu Gln Lys Arg
            20                  25                  30

Leu Tyr Val Leu Arg Gln Leu Asp Gly Ala Glu Arg Ser Tyr Asn Met
        35                  40                  45

Ser Ala Ala Leu Leu Leu Glu Gly Lys Leu Asp Arg Met Arg Val Glu
    50                  55                  60

<210> SEQ ID NO 42
```

```
<211> LENGTH: 21
<212> TYPE: PRT
<213> ORGANISM: Polymyxa betae

<400> SEQUENCE: 42

His Ala Phe Arg Ala Leu Ile Gln Arg His Glu Thr Leu Arg Thr Gly
 1               5                  10                  15

Ile Glu Gln Val Gln
            20

<210> SEQ ID NO 43
<211> LENGTH: 427
<212> TYPE: PRT
<213> ORGANISM: Polymyxa betae

<400> SEQUENCE: 43

Gly Glu Leu Val Gln Arg Ile Tyr Asp Glu Val Glu Phe Ala Val Asp
 1               5                  10                  15

Tyr Phe Gln Ala Ser Glu Arg Glu Val Glu Gln Val Val Glu Ala Tyr
            20                  25                  30

Tyr His Pro Phe Asp Leu Thr Lys Pro Pro Leu Leu Arg Ile Gly Leu
        35                  40                  45

Ile Glu Val Ala Glu Asp Arg His Ile Leu Leu Phe Asp Met His His
 50                  55                  60

Ile Val Ser Asp Gly Ile Ser Thr Ala Leu Leu Phe Asp Glu Phe Ser
 65                  70                  75                  80

Arg Leu Tyr Arg Gly Glu Glu Leu Gly Pro Leu Arg Ile Gln Tyr Lys
                85                  90                  95

Asp Tyr Ala Val Trp Gln His Ser Glu Ala Tyr Gly Gln Met Leu Gln
            100                 105                 110

Pro Gln Lys Glu Tyr Trp Leu Glu Gln Leu Ser Gly Glu Leu Pro Val
        115                 120                 125

Leu Glu Leu Pro Thr Asp Phe Pro Arg Pro Ala Val Gln Ser Phe Asp
130                 135                 140

Gly Arg Thr Val Lys Phe Tyr Ile Glu Lys Asp Arg Thr Glu Lys Leu
145                 150                 155                 160

Lys Glu Leu Ala Ala Arg Thr Gly Thr Thr Leu Tyr Met Val Leu Leu
                165                 170                 175

Ser Ala Tyr Thr Ile Leu Met His Lys Tyr Ser Gly Gln Glu Asp Leu
            180                 185                 190

Ile Val Gly Thr Pro Ile Ala Gly Arg Thr Gln Glu Glu Val Gln Pro
        195                 200                 205

Ile Val Gly Met Phe Ile Asn Thr Leu Ala Ile Arg Ser Arg Pro Glu
210                 215                 220

Arg Ser Lys Pro Tyr Leu Ser Tyr Leu Glu Glu Ile Lys Asp Ile Thr
225                 230                 235                 240

Leu Gly Ala Phe Glu His Gln Asn Tyr Leu Phe Glu Asp Leu Val Glu
                245                 250                 255

Ser Leu His Ile Pro Arg Ala Thr Gly Arg Asn Pro Leu Phe Asp Thr
            260                 265                 270

Phe Phe Ser Leu Gln Asn Thr Glu Asn Glu Gln Ile Val Ile Glu Gly
        275                 280                 285

Leu Glu Gln Ser Phe Tyr Pro Leu Glu Asn Gln Thr Ser Lys Phe Glu
290                 295                 300

Leu Leu Leu Asp Ile Ser Glu Leu Asp Gly Gln Leu Glu Cys Arg Leu
305                 310                 315                 320
```

```
Glu Tyr Ala Thr Ala Leu Tyr Lys Gln Glu Thr Ala Glu Arg Phe Ala
                325                 330                 335

Arg His Tyr Asp Lys Leu Leu Glu Thr Ile Ala Ala Pro Asp Gly
            340                 345                 350

Asp Ile Ala Ser Leu Glu Met Leu Lys Glu Glu Ile Arg Glu Leu
        355                 360                 365

Val Arg Gly Phe Asn Asp Ser Glu Ala Asp Tyr Pro Arg Gln Gln Thr
    370                 375                 380

Ile His Gly Leu Phe Glu Gln Ala Glu Leu Tyr Pro Asp Asn Val
385                 390                 395                 400

Ala Ala Val Met Asn Glu Arg Gln Leu Thr Tyr Arg Glu Leu Asn Glu
                405                 410                 415

Arg Ser Asn Arg Leu Ala Arg Lys Leu Arg Glu
                420                 425

<210> SEQ ID NO 44
<211> LENGTH: 520
<212> TYPE: PRT
<213> ORGANISM: Polymyxa betae

<400> SEQUENCE: 44

Arg Glu Thr Gly Val Glu Ala Asp Gln Leu Val Ala Ile Leu Ala Glu
1               5                   10                  15

Arg Ser Leu Asp Met Val Val Gly Ile Leu Ala Ile Leu Lys Ala Gly
                20                  25                  30

Gly Ala Tyr Val Pro Val Asp Pro Asp Tyr Pro Glu Glu Arg Ile Arg
            35                  40                  45

Phe Met Ile Glu Asp Ser Gly Ala Pro Leu Leu Leu Ile Gln Lys His
    50                  55                  60

Leu His Glu Lys Thr Asp Phe Ala Gly Thr Arg Leu Glu Leu Asp Asp
65                  70                  75                  80

Phe Val Trp Gly Asp Arg Gly Ala Asn Ser Ala Glu Ala Leu Asp Ala
                85                  90                  95

Ser Asn Leu Glu Pro Ile Ser Gly Pro Gly Asn Leu Ala Tyr Val Ile
                100                 105                 110

Tyr Thr Ser Gly Thr Thr Gly Arg Pro Lys Gly Thr Leu Ile Glu His
            115                 120                 125

Lys Asn Val Val Arg Leu Leu Phe Asn Asp Lys Asn Leu Phe Asp Phe
        130                 135                 140

Gly Pro Ser Asp Thr Trp Thr Leu Phe His Ser Phe Cys Phe Asp Phe
145                 150                 155                 160

Ser Val Trp Glu Met Tyr Gly Ala Leu Leu Tyr Gly Gly Lys Leu Val
                165                 170                 175

Ile Val Pro Pro Leu Thr Ala Lys Asn Pro Ala Asp Phe Leu Ala Leu
                180                 185                 190

Leu Gly Arg Glu Gln Val Thr Ile Leu Asn Gln Thr Pro Thr Tyr Phe
            195                 200                 205

Tyr Gln Leu Leu Arg Glu Val Leu Ala Asp His Pro Tyr Asp Leu Arg
        210                 215                 220

Ile Arg Asn Val Ile Phe Gly Gly Glu Ala Leu Ser Pro Leu Leu Leu
225                 230                 235                 240

Lys Gly Phe Lys Thr Lys Tyr Pro Glu Thr Lys Leu Ile Asn Met Tyr
                245                 250                 255

Gly Ile Thr Glu Thr Thr Val His Val Thr Tyr Lys Glu Ile Thr Trp
```

```
                    260                 265                 270
Val Glu Met Glu Ala Ala Lys Ser Asn Ile Gly Lys Pro Ile Pro Thr
            275                 280                 285

Leu Arg Val Tyr Val Leu Asp Glu Asn Arg Arg Pro Val Pro Ile Gly
        290                 295                 300

Val Ala Gly Glu Met Tyr Val Ala Gly Glu Gly Leu Ala Arg Gly Tyr
305                 310                 315                 320

Leu Asn Arg Pro Asp Leu Thr Ala Glu Lys Phe Val Asp Ser Pro Phe
                325                 330                 335

Ala Glu Gly Glu Lys Leu Tyr Arg Ser Gly Asp Leu Ala Ala Trp Leu
            340                 345                 350

Pro Asp Gly Asn Ile Glu Tyr Leu Gly Arg Ile Asp His Gln Val Lys
        355                 360                 365

Ile Arg Gly Tyr Arg Ile Glu Leu Asp Glu Ile Glu Thr Gln Leu Leu
370                 375                 380

Asn Val Arg Gly Val Glu Glu Ala Val Val Leu Ala Arg Gln Asp Gly
385                 390                 395                 400

Gly Gly Glu Lys Ala Leu Val Ala Tyr Phe Val Ala Asp Arg Thr Leu
                405                 410                 415

Thr Val Ser Glu Met Arg Thr Ser Leu Ala Gln Gly Met Pro Gly Tyr
            420                 425                 430

Met Ile Pro Ser Tyr Phe Val Gln Leu Glu Arg Met Pro Leu Thr Thr
        435                 440                 445

Asn Gly Lys Val Asp Arg Lys Ala Leu Pro Glu Pro Gln Gly Gly Ile
    450                 455                 460

Gln Thr Gly Val Glu Tyr Val Ala Pro Arg Asn Trp Thr Glu Ser Gln
465                 470                 475                 480

Leu Val Lys Ile Trp Glu Val Leu Gly Tyr Ser Gly Ile Gly Val
                485                 490                 495

Leu Asp Asn Phe Phe Glu Leu Gly Gly His Ser Leu Arg Ala Thr Asn
                500                 505                 510

Leu Val Ser Lys Ile Arg Lys Glu
            515                 520

<210> SEQ ID NO 45
<211> LENGTH: 20
<212> TYPE: PRT
<213> ORGANISM: Polymyxa betae

<400> SEQUENCE: 45

Met Asn Val Glu Leu Pro Leu Arg Asp Val Phe Arg Tyr Thr Thr Val
1               5                   10                  15

Glu Ser Met Ala
            20

<210> SEQ ID NO 46
<211> LENGTH: 63
<212> TYPE: PRT
<213> ORGANISM: Polymyxa betae

<400> SEQUENCE: 46

Gly Ala Ile Ala Ser Leu Glu Glu Thr Gln His Ser Ser Ile Pro Lys
1               5                   10                  15

Ala Glu Glu Lys Ala Tyr Tyr Pro Val Ser Ser Ala Gln Lys Arg Leu
            20                  25                  30

Tyr Val Leu His Gln Leu Asp Ser Ser Glu Leu Asn Tyr Asn Leu Pro
```

```
            35                  40                  45
Ser Ala Leu Gln Leu Glu Gly Ala Leu Asn Glu Ala Lys Val Glu
 50                  55                  60

<210> SEQ ID NO 47
<211> LENGTH: 21
<212> TYPE: PRT
<213> ORGANISM: Polymyxa betae

<400> SEQUENCE: 47

Lys Ala Leu Thr Thr Leu Val Ala Arg His Asp Met Leu Arg Thr Gly
  1               5                  10                  15

Phe Glu Ile Val Asn
             20

<210> SEQ ID NO 48
<211> LENGTH: 427
<212> TYPE: PRT
<213> ORGANISM: Polymyxa betae

<400> SEQUENCE: 48

Gly Glu Pro Val Gln Arg Ile His Pro Leu Val Ala Phe Lys Val Glu
  1               5                  10                  15

Lys Leu Gln Ala Ser Glu Asp Gln Val Ala Ala Ile Leu Glu Gly Phe
                 20                  25                  30

Ile Gln Pro Phe Asp Leu Thr Gln Pro Pro Leu Leu Arg Ala Leu Leu
             35                  40                  45

Ile Glu Leu Glu Lys Glu Lys Phe Leu Leu Ala Leu Asp Ile His His
 50                  55                  60

Ile Gly Ser Asp Gly Leu Ser Met Asp Val Leu Leu Arg Glu Phe Val
 65                  70                  75                  80

Arg Leu Tyr Asn Gly Glu Glu Leu Pro Glu Leu Arg Ile Gln Tyr Lys
                 85                  90                  95

Asp Tyr Ala Val Trp Gln Gln Ser Glu Glu Gln Arg Gln Arg Ile Lys
            100                 105                 110

Arg Gln Glu Glu Tyr Trp Arg Gly Val Phe Ser Ser Glu Leu Pro Val
            115                 120                 125

Leu Glu Leu Pro Leu Asp Phe Ser Arg Pro Ala Val Gln Gln Phe Asp
130                 135                 140

Gly Gln Thr Leu Thr Phe Thr Leu Asp Ala Glu Lys Ser Glu Ala Leu
145                 150                 155                 160

Lys Arg Leu Ala Gly Asp Ser Gly Ala Thr Leu Tyr Met Leu Leu Leu
                165                 170                 175

Ala Ala Tyr Ser Val Leu Leu His Lys Tyr Ala Gly Gln Glu Asp Ile
                180                 185                 190

Val Val Gly Thr Pro Ile Ala Ala Arg Ser His Ala Asp Leu Gln Pro
            195                 200                 205

Ile Ile Gly Met Phe Val Asn Thr Leu Ala Leu Arg Leu Arg Pro Ala
210                 215                 220

Ala Glu Arg Thr Phe Leu Asp Tyr Leu Gln Glu Val Lys Glu Thr Thr
225                 230                 235                 240

Leu Gly Ala Tyr Glu His Gln Asp Tyr Pro Phe Glu Glu Leu Val Glu
                245                 250                 255

Ala Leu Gln Val Ser Arg Asp Leu Ser Arg Asn Pro Leu Phe Asp Thr
            260                 265                 270

Met Phe Ser Leu Gln Lys His Glu Ser Leu Asp Leu Thr Leu Glu Gly
```

```
                275                 280                 285
Leu Gln Trp Ser Leu Phe Asp Ile Glu Glu Lys Thr Ala Lys Phe Asp
        290                 295                 300

Leu Ser Phe Asp Ile Val Glu Ala Asp Asn Glu Leu Val Cys Lys Ile
305                 310                 315                 320

Glu Tyr Ala Thr Ser Leu Phe Arg Gln Glu Thr Met Val Arg Leu Ala
                325                 330                 335

Gly His Tyr Glu Gln Leu Leu Ala Ser Ile Leu Ala Gln Pro Gly Ala
            340                 345                 350

Arg Ile Ser Asp Leu Asp Ile Leu Thr Asp Ser Glu Lys His Asp Leu
        355                 360                 365

Leu Val Gly Phe Asp Val Ser Ser Ser Ala Leu Ala Lys Gln Pro Ala
    370                 375                 380

Ala Glu Gly Thr Gly Leu Glu Ala Asp Glu Ser Trp Arg Glu Arg Thr
385                 390                 395                 400

Phe His Glu Leu Phe Glu Glu Gln Ala Glu Arg Thr Pro Gly Ala Leu
                405                 410                 415

Ala Val Val Tyr Glu Asp Ser Lys Leu Thr Tyr
            420                 425

<210> SEQ ID NO 49
<211> LENGTH: 31
<212> TYPE: PRT
<213> ORGANISM: Polymyxa betae

<400> SEQUENCE: 49

Ala Glu Leu Asn Ala Lys Ala Asn Arg Leu Ala Tyr Ala Leu Arg Ala
1               5                   10                  15

Arg Gly Val Lys Pro Glu Gln Val Val Gly Ile Leu Ala Gly Arg
            20                  25                  30

<210> SEQ ID NO 50
<211> LENGTH: 556
<212> TYPE: PRT
<213> ORGANISM: Polymyxa betae

<400> SEQUENCE: 50

Ser Ala Glu Leu Leu Val Gly Val Leu Ala Val Trp Lys Ala Gly Gly
1               5                   10                  15

Ala Tyr Val Pro Leu Asp Pro Asp Tyr Pro Ala Glu Arg Ile Glu Tyr
            20                  25                  30

Met Leu Ala Asp Ser Gly Ala Ser Val Leu Leu Thr Gln Thr Cys Leu
        35                  40                  45

Leu Glu Gln Ala Glu Ala Trp Arg Ser Asp Gly Ala Leu Val Leu Gln
    50                  55                  60

Thr Val Leu Ala Leu Asp Asp Ala Ala Thr Tyr Ser Leu Gly Ala Ala
65                  70                  75                  80

Glu Ala Ala Val Gly Val Gln Ala Leu Gly Glu Ala Gly Ala Glu Ala
                85                  90                  95

Glu Ala Leu Ala Gln Ala Glu Thr Ala Ala Glu Lys Ser Ala Thr
            100                 105                 110

Ala Glu Ala Glu Lys Asn Val Leu Ala Ala Asp Leu Ala Ser Asn Pro
        115                 120                 125

Ala Asn Val Asn Lys Pro Ser Asp Leu Ala Tyr Val Ile Tyr Thr Ser
    130                 135                 140

Gly Thr Thr Gly Arg Pro Lys Gly Val Ala Val Glu His Arg Ser Leu
```

```
            145                 150                 155                 160
        Val Asn Thr Ala Ala Gly Tyr Arg Arg Asp Tyr Arg Leu Asp Gln Phe
                        165                 170                 175

Pro Ile Arg Leu Leu Gln Leu Ala Ser Phe Ser Phe Asp Val Phe Val
                        180                 185                 190

Gly Asp Ile Ala Arg Thr Leu Tyr Asn Gly Gly Thr Met Val Ile Val
                        195                 200                 205

Pro Lys Asp Asp Arg Ile Asp Pro Thr Arg Leu Tyr Gly Trp Ile Arg
                        210                 215                 220

Asp Tyr Ala Val Thr Val Phe Glu Ser Thr Pro Ala Leu Ile Val Pro
        225                 230                 235                 240

Phe Met Glu His Val His Ala Glu Gly Leu Asp Leu Ser Ser Met Gln
                        245                 250                 255

Leu Leu Ile Thr Ser Ser Asp Ala Cys Ser Val Ala Asp Tyr Arg Thr
                        260                 265                 270

Leu Gln Glu Arg Phe Gly Ser Gln Phe Arg Ile Ile Asn Ser Tyr Gly
                        275                 280                 285

Val Thr Glu Ala Ala Ile Asp Ser Ser Phe Tyr Asp Glu Pro Leu Glu
                        290                 295                 300

Lys Leu Pro Lys Thr Gly Ser Val Pro Ile Gly Lys Ala Trp Leu Asn
        305                 310                 315                 320

Ala Lys Phe Tyr Ile Val Asp Ala Asn Leu Lys Pro Val Pro Ile Gly
                        325                 330                 335

Val Leu Gly Glu Leu Val Ile Gly Gly Ala Gly Val Ala Arg Gly Tyr
                        340                 345                 350

Leu Asn Arg Pro Asp Leu Thr Ala Glu Lys Phe Val Asp Ser Pro Phe
                        355                 360                 365

Ala Ala Gly Glu Arg Leu Tyr Arg Thr Gly Asp Leu Ala Arg Trp Met
                        370                 375                 380

Pro Asp Gly Asn Val Asp Phe Ile Gly Arg Ile Asp Asn Gln Val Lys
        385                 390                 395                 400

Ile Arg Gly Tyr Arg Ile Glu Leu Gly Glu Ile Glu Ala Ala Met Lys
                        405                 410                 415

Asn Phe Ala Gly Val Arg Gln Ala Leu Val Ile Asp Arg Thr Asp Glu
                        420                 425                 430

Arg Gly Gln Lys Tyr Leu Cys Gly Tyr Val Val Ala Asp Ser Ser Phe
                        435                 440                 445

Asp Leu Glu Gly Leu Val Ala His Leu Asp Ala Ala Leu Pro Ser His
                        450                 455                 460

Met Val Pro Ser Arg Ile Met Arg Leu Asp Gln Met Pro Leu Thr Pro
        465                 470                 475                 480

Asn Gly Lys Ile Asp Arg Lys Ala Leu Pro Val Pro Glu Gly Ser Ile
                        485                 490                 495

Arg Ala Glu Ala Ala Tyr Thr Ala Pro Arg Thr Pro Ala Glu Gln Ala
                        500                 505                 510

Leu Ala Ser Val Trp Gln Ser Val Leu Gly Val Asp Gln Val Gly Thr
                        515                 520                 525

Met Asp Asn Phe Phe Ala Leu Gly Gly Asp Ser Ile Lys Ala Leu Gln
                        530                 535                 540

Val Ser Ser Arg Leu Leu Gln Thr Gly Tyr Lys Leu
        545                 550                 555

<210> SEQ ID NO 51
```

```
<211> LENGTH: 14
<212> TYPE: PRT
<213> ORGANISM: Polymyxa betae

<400> SEQUENCE: 51

Val Met Lys Asp Leu Phe His Tyr Pro Thr Ile Ser Ala Leu
1               5                   10

<210> SEQ ID NO 52
<211> LENGTH: 61
<212> TYPE: PRT
<213> ORGANISM: Polymyxa betae

<400> SEQUENCE: 52

Ser Leu Gln Leu Gln Thr Ala Glu Arg Thr Ala Ser Gln Ala Glu Val
1               5                   10                  15

Thr Gly Glu Val Ile Leu Thr Pro Ile Gln Arg Trp Phe Phe Glu Gln
                20                  25                  30

Asn Pro Ala Asp Val His His Ser Asn Gln Ala Phe Met Gln Phe Ser
            35                  40                  45

Lys Glu Gly Phe Asp Glu Glu Ala Leu Arg Gln Ala Val
        50                  55                  60

<210> SEQ ID NO 53
<211> LENGTH: 20
<212> TYPE: PRT
<213> ORGANISM: Polymyxa betae

<400> SEQUENCE: 53

Arg Gln Ile Val Val His His Asp Ala Leu Arg Thr Val Tyr Arg Gln
1               5                   10                  15

Ala Asp Asn Gly
            20

<210> SEQ ID NO 54
<211> LENGTH: 459
<212> TYPE: PRT
<213> ORGANISM: Polymyxa betae

<400> SEQUENCE: 54

Tyr Thr Ala Trp Asn Arg Gly Ala Gly Glu Asn Glu Ala Leu Phe Asp
1               5                   10                  15

Leu Glu Val Val Asp Phe Lys Gly Val Gly Asp Val Lys Glu Ala Val
                20                  25                  30

Glu Ala Lys Ala Asn Asp Ile Gln Ala Ser Ile Asp Leu Glu Asn Gly
            35                  40                  45

Pro Leu Val Lys Leu Gly Leu Phe Arg Cys Asp Gly Asp His Leu
        50                  55                  60

Leu Ile Ala Ile His His Leu Val Val Asp Gly Val Ser Trp Arg Ile
65                  70                  75                  80

Leu Leu Glu Asp Phe Ala Ala Gly Tyr Glu Gln Ala Leu Gln Gly Gln
                85                  90                  95

Pro Ile Arg Leu Pro Leu Lys Thr Asp Ser Phe Gln Thr Trp Ala Lys
            100                 105                 110

Gln Leu Ala Asp Tyr Ala Asn Ser Pro Ala Met Glu Ser Glu Arg Glu
        115                 120                 125

Tyr Trp Gln His Ile Glu Gln Leu Thr Tyr Glu Pro Leu Pro Lys Asp
    130                 135                 140

Phe Glu Gln Gly Arg Ser Lys Leu Lys Asp Ser Gly Leu Val Thr Val
```

```
            145                 150                 155                 160
Arg Trp Thr Ala Glu Glu Thr Glu Gln Leu Leu Lys Gln Ala His Arg
                165                 170                 175
Ala Tyr His Thr Glu Met Asn Asp Leu Leu Ala Ala Leu Gly Leu
            180                 185                 190
Ala Leu Gln Ala Trp Ser Gly Arg Glu Arg Val Leu Val Asn Leu Glu
        195                 200                 205
Gly His Gly Arg Glu Asp Ile Leu Pro Asp Val Asp Ile Thr Arg Thr
    210                 215                 220
Val Gly Trp Phe Thr Ser Gln Phe Pro Val Val Leu Glu Pro Gly His
225                 230                 235                 240
Ala Gln Ala Leu Gly His Gln Val Lys Gln Val Lys Glu Ser Leu Arg
                245                 250                 255
Arg Ile Pro Asn Lys Gly Ile Gly Tyr Gly Ile Leu Arg Tyr Leu Ser
            260                 265                 270
Ala Pro Arg Glu Gly Glu Tyr Phe Val Leu Glu Pro Glu Ile Ser Phe
        275                 280                 285
Asn Tyr Leu Gly Gln Phe Asp His Asp Tyr Glu Ser Ser Ser Ser Gln
    290                 295                 300
Pro Ser Pro Phe Ser Pro Gly Ser Asp Ser Ser Pro Asn Ala Val Met
305                 310                 315                 320
Asp Tyr Val Leu Asp Ile Asn Gly Met Val Ser Gly Ala Leu Glu
                325                 330                 335
Leu Thr Ile Arg Tyr Gly Glu Thr Gln Tyr Lys Arg Glu Thr Val Glu
            340                 345                 350
Arg Leu Gly Thr Leu Leu Gln Ser Ser Leu Arg Glu Val Ile Ser His
        355                 360                 365
Cys Leu Ser Lys Glu Arg Pro Glu Leu Thr Pro Ser Asp Val Leu Leu
    370                 375                 380
Gln Asp Val Thr Val Glu Leu Glu Arg Leu Ser Glu His Thr Val
385                 390                 395                 400
Ala Leu Gly Glu Leu Glu Asn Val Tyr Thr Leu Thr Pro Leu Gln Lys
                405                 410                 415
Gly Met Leu Phe His Ser Leu Leu Asp Ala Asp Ser Glu Ala Tyr Phe
            420                 425                 430
Glu Gln Val Thr Phe Asp Leu Tyr Gly Ser Leu Asn Val Glu Ala Phe
        435                 440                 445
Thr Arg Gly Leu Asp Thr Leu Val Gln Arg Asn
    450                 455

<210> SEQ ID NO 55
<211> LENGTH: 11
<212> TYPE: PRT
<213> ORGANISM: Polymyxa betae

<400> SEQUENCE: 55

Glu Ala Leu Arg Thr Asn Phe Ile Thr Gly Trp
1               5                   10

<210> SEQ ID NO 56
<211> LENGTH: 437
<212> TYPE: PRT
<213> ORGANISM: Polymyxa betae

<400> SEQUENCE: 56

Arg Asp Glu Pro Ile Gln Val Val Phe Arg Glu Arg Lys Cys Glu Val
```

```
  1               5                   10                  15
Tyr Phe Glu Asp Ile Arg Ser Val Ser Asp Glu His Pro Glu Lys Thr
                20                  25                  30

Ile Ala Asp Phe Val Ser Ala Asp Lys Ala Asn Lys Phe Asp Leu Ala
                35                  40                  45

Arg Gly Pro Leu Met Arg Val Thr Val Val Arg Thr Gly Asp Glu Ser
            50                  55                  60

Tyr His Val Ile Trp Ser His His Ile Leu Met Asp Gly Trp Cys
65                  70                  75                  80

Met Ser Phe Met Ile Lys Glu Val Phe Asp Thr Tyr Phe Ala Phe Gln
                85                  90                  95

Glu Lys Arg Thr Leu Glu Leu Pro Pro Val Thr Ser Tyr Ser Arg Tyr
                100                 105                 110

Ile Glu Trp Leu Glu Ala Gln Asp Ala Ala Lys Ala Ser Arg Tyr Trp
            115                 120                 125

Ser Glu Tyr Leu Ala Gly Tyr Asp Gln Gln Thr Lys Leu Pro Gln Glu
    130                 135                 140

Lys Thr Gln Leu Lys Gln Gly Ala Phe Glu Ala Ala Glu Ile Asp Val
145                 150                 155                 160

Glu Leu Ser Lys Glu Leu Thr Gly Gln Ile Glu Arg Val Ala Arg Gln
                165                 170                 175

Gln Gln Val Thr Leu Asn Thr Phe Met Gln Thr Val Trp Gly Leu Val
                180                 185                 190

Leu Gln Ile Tyr Asn Asn Ser Glu Asp Val Val Phe Gly Ser Val Val
            195                 200                 205

Ser Gly Arg Pro Ala Glu Ile Pro Gly Ile Glu Ser Met Ile Gly Leu
    210                 215                 220

Phe Ile Asn Thr Ile Pro Val Arg Ile Gln Gly Lys Ala Glu Glu Arg
225                 230                 235                 240

Val Ala Asp Ile Leu Arg Lys Thr Gln Asp Gln Ala Leu Ala Ser Gly
                245                 250                 255

Ala Tyr Glu Thr Phe Pro Leu Phe Glu Ile Gln Ser Leu Ser Glu Gln
                260                 265                 270

Lys Arg Asp Leu Ile Asn His Ile Met Val Phe Glu Asn Tyr Pro Met
        275                 280                 285

Glu Glu Gln Ile Glu Gln Val Val Gly Gly Arg Glu Ala Leu Lys
    290                 295                 300

Ile Ala Asn Ile Gln Ser Pro Glu Gln Thr Asn Tyr Asp Leu Asp Ile
305                 310                 315                 320

Thr Val Ile Pro Glu Glu His Ile Leu Leu Arg Phe Thr Tyr Asn Ala
                325                 330                 335

Leu Thr Phe Arg Glu Asp Asp Ile Arg Gln Ile His Ser His Phe Ala
                340                 345                 350

Trp Ala Leu Glu Lys Val Ala Ala Asn Pro Asn Ile Leu Val Asn Gln
            355                 360                 365

Leu Glu Leu Leu Thr Ala Ala Glu Lys Glu Gln Ile Leu Gly Ala Phe
    370                 375                 380

Asn Pro Ala Gln Pro Glu Ala Ala Pro Ala Ala Phe His Arg Leu
385                 390                 395                 400

Phe Glu Glu Gln Val Glu Arg Thr Pro Glu Glu Ala Ala Val Val Tyr
                405                 410                 415

Glu Asn Asp Arg Leu Thr Tyr Ala Glu Leu Asn Glu Arg Ala Asn Arg
                420                 425                 430
```

Leu Ala Ala Thr Leu
        435

<210> SEQ ID NO 57
<211> LENGTH: 556
<212> TYPE: PRT
<213> ORGANISM: Polymyxa betae

<400> SEQUENCE: 57

Ala Thr Leu Arg Ala Ser Gly Ile Gly Arg Glu Thr Ile Val Gly Ile
 1               5                  10                  15

Leu Ala Glu Arg Ser Val Asp Leu Leu Val Ala Val Leu Ala Val Trp
            20                  25                  30

Lys Ala Gly Gly Ala Tyr Val Pro Leu Asp Pro Asp Tyr Pro Ala Asp
        35                  40                  45

Arg Val Arg Phe Met Leu Glu Asp Ser Gly Ala Lys Val Leu Leu Thr
    50                  55                  60

Gln Thr Ala Leu Arg Glu Arg Ala Glu Ala Trp Leu Gly Glu Glu Glu
65                  70                  75                  80

Leu Ala Leu Ala Ala Val Leu Tyr Leu Asp Asp Glu Ala Ser Tyr Asn
                85                  90                  95

Glu Glu Arg Ala Asn Ala Pro Val Gly Ser Gly Met Val Ser Gly Lys
            100                 105                 110

Leu Thr Asp Ala Val Asp Asp Gly Asp Glu Ser His Gln Asn Val Gly
        115                 120                 125

Thr Asp Gly Phe His Glu Ala Arg Pro Glu Asp Leu Ala Tyr Val Ile
    130                 135                 140

Tyr Thr Ser Gly Thr Thr Gly Lys Pro Lys Gly Val Met Ile Glu His
145                 150                 155                 160

Arg Ser Leu Val Asn Thr Ala Ala Gly Tyr Arg Arg Glu Tyr Arg Leu
                165                 170                 175

Asp Gln Phe Pro Val Arg Leu Leu Gln Leu Ala Ser Phe Ser Phe Asp
            180                 185                 190

Val Phe Val Gly Asp Ile Ala Arg Thr Leu Tyr Asn Gly Gly Thr Met
        195                 200                 205

Val Ile Val Pro Lys Asp Asp Arg Ile Asp Pro Ser Arg Leu His His
    210                 215                 220

Trp Met Glu Arg Glu Arg Val Thr Ile Phe Glu Ser Thr Pro Ala Leu
225                 230                 235                 240

Ile Val Pro Phe Leu Glu Tyr Val His Asp Gln Gln Leu Asp Met Ser
                245                 250                 255

Trp Met Glu Leu Leu Ile Thr Ser Ser Asp Ser Cys Ser Val Ala Asp
            260                 265                 270

Tyr Arg Thr Leu Gln Glu Arg Phe Gly Ser Leu Phe Arg Ile Ile Asn
        275                 280                 285

Ala Tyr Gly Val Thr Glu Ala Ala Ile Asp Ser Ser Phe Tyr Asp Glu
    290                 295                 300

Glu Leu Ala Lys Leu Pro Gln Thr Gly His Val Pro Ile Gly Lys Ala
305                 310                 315                 320

Trp Leu Asn Ala Lys Phe Tyr Ile Val Asp Ala His Leu Asn Pro Val
                325                 330                 335

Pro Val Gly Val Leu Gly Glu Leu Val Ile Gly Gly Val Gly Val Ala
            340                 345                 350

Arg Gly Tyr Leu Asn Arg Pro Glu Leu Thr Gly Glu Lys Phe Val Asp

-continued

```
                355                 360                 365
Ser Pro Phe Ala Ala Gly Glu Arg Leu Tyr Arg Thr Gly Asp Leu Ala
370                 375                 380

Arg Trp Met Glu Asp Gly Asn Val Asp Phe Ile Gly Arg Ile Asp Asn
385                 390                 395                 400

Gln Ala Lys Ile Arg Gly Tyr Arg Ile Glu Thr Gly Glu Val Glu Ala
                405                 410                 415

Lys Leu Leu Ser Val Gly Val Lys Glu Ala Val Val Val Arg
                420                 425                 430

Glu Asp Gln Glu Gly Gln Lys Ala Leu Cys Ala Tyr Tyr Thr Ala Glu
                435                 440                 445

Glu Gly Leu Thr Ala Ala Asp Leu Lys Arg Ala Ile Ala Ser Glu Leu
                450                 455                 460

Pro Gly Tyr Met Ile Pro Ser Tyr Phe Val Glu Leu Glu Arg Leu Pro
465                 470                 475                 480

Leu Thr Pro Asn Gly Lys Ile Asp Arg Lys Ala Leu Pro Ala Pro Glu
                485                 490                 495

Gly Gly Ala Gly Gly Arg Glu Tyr Val Ala Pro Arg Thr Glu Leu
                500                 505                 510

Glu Ala Lys Leu Ala Ala Ile Trp Gln Asp Val Leu Val Arg Glu Lys
                515                 520                 525

Ala Val Gly Val Thr Asp Asn Phe Phe Asp Leu Gly His Ser Leu
530                 535                 540

Arg Ala Thr Thr Leu Val Ser Lys Met His Lys Glu
545                 550                 555
```

```
<210> SEQ ID NO 58
<211> LENGTH: 18
<212> TYPE: PRT
<213> ORGANISM: Polymyxa betae

<400> SEQUENCE: 58

Leu Gly Val Glu Phe Pro Leu Arg Asp Val Phe Arg Tyr Pro Thr Val
1               5                   10                  15

Glu Glu

<210> SEQ ID NO 59
<211> LENGTH: 65
<212> TYPE: PRT
<213> ORGANISM: Polymyxa betae

<400> SEQUENCE: 59

Met Ala Ala Ala Met Glu Arg Leu Glu Ile Gly Ser Phe Met Ala Ile
1               5                   10                  15

Pro Ala Ala Glu Pro Ser Glu Tyr Tyr Pro Leu Ser Ser Ala Gln Lys
                20                  25                  30

Arg Leu Tyr Ile Leu Asn Gln Leu Gly Ala Glu Leu Ser Tyr Asn
            35                  40                  45

Ile Pro Gly Ala Met Leu Leu Glu Gly Glu Leu Asp Arg Gln Arg Phe
        50                  55                  60

Glu
65

<210> SEQ ID NO 60
<211> LENGTH: 21
<212> TYPE: PRT
<213> ORGANISM: Polymyxa betae
```

<400> SEQUENCE: 60

| Glu | Ala | Phe | Arg | Gly | Leu | Val | Ala | Arg | His | Glu | Thr | Leu | Arg | Thr | Gly |
|---|---|---|---|---|---|---|---|---|---|---|---|---|---|---|---|
| 1 | | | | 5 | | | | | 10 | | | | | 15 | |

| Phe | Glu | Met | Val | Lys |
|---|---|---|---|---|
| | | | | 20 |

<210> SEQ ID NO 61
<211> LENGTH: 425
<212> TYPE: PRT
<213> ORGANISM: Polymyxa betae

<400> SEQUENCE: 61

| Gly | Glu | Ala | Val | Gln | Arg | Ile | Tyr | Glu | Glu | Ala | Phe | Gln | Val | Glu |
|---|---|---|---|---|---|---|---|---|---|---|---|---|---|---|
| 1 | | | | 5 | | | | | 10 | | | | | 15 |

| Tyr | Val | Gln | Ile | Ser | Ala | Glu | Gln | Ala | Glu | Glu | Thr | Val | Arg | Gln | Phe |
|---|---|---|---|---|---|---|---|---|---|---|---|---|---|---|---|
| | | | 20 | | | | | 25 | | | | | 30 | | |

| Val | Arg | Pro | Phe | Asp | Leu | Ala | Lys | Pro | Pro | Leu | Leu | Arg | Val | Gly | Leu |
|---|---|---|---|---|---|---|---|---|---|---|---|---|---|---|---|
| | | | 35 | | | | | 40 | | | | | 45 | | |

| Ala | Glu | Leu | Ala | Pro | Asp | Arg | His | Ile | Leu | Met | Phe | Asp | Thr | His | His |
|---|---|---|---|---|---|---|---|---|---|---|---|---|---|---|---|
| | 50 | | | | | 55 | | | | | 60 | | | | |

| Ile | Val | Ser | Asp | Gly | Val | Ser | Ile | Asp | Val | Leu | Ile | Glu | Glu | Leu | Val |
|---|---|---|---|---|---|---|---|---|---|---|---|---|---|---|---|
| 65 | | | | | 70 | | | | | 75 | | | | | 80 |

| Arg | Leu | Tyr | Ser | Gly | Glu | Gln | Leu | Glu | Pro | Leu | Arg | Ile | Gln | Tyr | Lys |
|---|---|---|---|---|---|---|---|---|---|---|---|---|---|---|---|
| | | | | 85 | | | | | 90 | | | | | 95 | |

| Asp | Tyr | Ala | Val | Trp | Gln | Gln | Ser | Asp | Glu | Gln | Lys | Ala | Gln | Leu | Ala |
|---|---|---|---|---|---|---|---|---|---|---|---|---|---|---|---|
| | | | 100 | | | | | 105 | | | | | 110 | | |

| Lys | Gln | Glu | Ala | Tyr | Trp | Leu | Asp | Met | Phe | Arg | Gly | Glu | Leu | Pro | Val |
|---|---|---|---|---|---|---|---|---|---|---|---|---|---|---|---|
| | | 115 | | | | | 120 | | | | | 125 | | | |

| Leu | Glu | Leu | Pro | Thr | Asp | Tyr | Pro | Arg | Pro | Ala | Met | Gln | Ser | Tyr | Glu |
|---|---|---|---|---|---|---|---|---|---|---|---|---|---|---|---|
| | 130 | | | | | 135 | | | | | 140 | | | | |

| Gly | Arg | Thr | Leu | Gln | Leu | Phe | Met | His | Ser | Glu | Lys | Ser | Glu | Gly | Leu |
|---|---|---|---|---|---|---|---|---|---|---|---|---|---|---|---|
| 145 | | | | | 150 | | | | | 155 | | | | | 160 |

| Lys | Arg | Leu | Ala | Ala | Glu | Asn | Gly | Ala | Thr | Leu | Tyr | Met | Val | Leu | Leu |
|---|---|---|---|---|---|---|---|---|---|---|---|---|---|---|---|
| | | | | 165 | | | | | 170 | | | | | 175 | |

| Ala | Gly | Tyr | Thr | Ile | Leu | Leu | His | Lys | Tyr | Thr | Gly | Gln | Glu | Asp | Val |
|---|---|---|---|---|---|---|---|---|---|---|---|---|---|---|---|
| | | | 180 | | | | | 185 | | | | | 190 | | |

| Val | Val | Gly | Thr | Pro | Ile | Ala | Gly | Arg | Asn | His | Ser | Asp | Val | Gln | Pro |
|---|---|---|---|---|---|---|---|---|---|---|---|---|---|---|---|
| | | 195 | | | | | 200 | | | | | 205 | | | |

| Leu | Ile | Gly | Met | Phe | Val | Asn | Thr | Leu | Ala | Ile | Arg | Ser | Tyr | Pro | Ala |
|---|---|---|---|---|---|---|---|---|---|---|---|---|---|---|---|
| | 210 | | | | | 215 | | | | | 220 | | | | |

| Ala | Asp | Lys | Thr | Phe | Leu | Glu | Tyr | Leu | Lys | Glu | Ile | Lys | Glu | Thr | Thr |
|---|---|---|---|---|---|---|---|---|---|---|---|---|---|---|---|
| 225 | | | | | 230 | | | | | 235 | | | | | 240 |

| Leu | Gly | Ala | Phe | Glu | His | Gln | Asn | Tyr | Pro | Phe | Glu | Glu | Leu | Val | Asp |
|---|---|---|---|---|---|---|---|---|---|---|---|---|---|---|---|
| | | | | 245 | | | | | 250 | | | | | 255 | |

| Lys | Val | Asn | Val | Ala | Arg | Asp | Leu | Arg | Arg | Asn | Pro | Leu | Phe | Asp | Thr |
|---|---|---|---|---|---|---|---|---|---|---|---|---|---|---|---|
| | | | 260 | | | | | 265 | | | | | 270 | | |

| Met | Phe | Ala | Leu | Gln | Asn | Thr | Glu | Asn | Leu | Glu | Ile | Gln | Leu | Pro | Gly |
|---|---|---|---|---|---|---|---|---|---|---|---|---|---|---|---|
| | | 275 | | | | | 280 | | | | | 285 | | | |

| Leu | His | Leu | Ser | Thr | Tyr | Ala | Ser | Glu | Glu | Ile | Val | Ser | Lys | Phe | Asp |
|---|---|---|---|---|---|---|---|---|---|---|---|---|---|---|---|
| | 290 | | | | | 295 | | | | | 300 | | | | |

| Leu | Ser | Leu | Asp | Val | Thr | Glu | Ile | Glu | Glu | Gly | Leu | Glu | Tyr | Leu | Phe |
|---|---|---|---|---|---|---|---|---|---|---|---|---|---|---|---|
| 305 | | | | | 310 | | | | | 315 | | | | | 320 |

| Glu | Tyr | Ala | Thr | Ala | Leu | Tyr | Lys | Thr | Glu | Thr | Val | Glu | Lys | Leu | Ala |
|---|---|---|---|---|---|---|---|---|---|---|---|---|---|---|---|
| | | | | 325 | | | | | 330 | | | | | 335 | |

-continued

```
Ala His Tyr Leu Gln Leu Leu Glu Ser Ile Leu Arg Asn Pro Ser Ala
            340                 345                 350

Thr Ile Ala Glu Leu Gly Ile Leu Thr Pro Ala Glu Lys Glu Gln Ile
        355                 360                 365

Leu Gly Ala Phe Asn Pro Ala Gln Pro Glu Ala Ala Pro Ala Thr Ala
    370                 375                 380

Phe His Arg Leu Phe Glu Glu Gln Val Glu Arg Thr Pro Glu Glu Ala
385                 390                 395                 400

Ala Val Val Tyr Glu Asn Asp Arg Leu Thr Tyr Ala Glu Leu Asn Lys
                405                 410                 415

Arg Ala Asn Arg Leu Ala Ala Thr Leu
            420                 425

<210> SEQ ID NO 62
<211> LENGTH: 556
<212> TYPE: PRT
<213> ORGANISM: Polymyxa betae

<400> SEQUENCE: 62

Ala Thr Leu Arg Ala Gly Gly Ile Gly Arg Glu Thr Ile Val Gly Ile
1               5                   10                  15

Leu Ala Glu Arg Ser Val Asp Leu Leu Val Ala Val Leu Ala Ile Trp
            20                  25                  30

Lys Ala Gly Gly Ala Tyr Val Pro Leu Asp Pro Asp Tyr Pro Ala Asp
        35                  40                  45

Arg Val Arg Phe Met Leu Glu Asp Ser Gly Ala Lys Val Leu Leu Thr
    50                  55                  60

Gln Thr Pro Leu Arg Glu Arg Ala Glu Ala Trp Leu Gly Glu Glu Glu
65                  70                  75                  80

Leu Ala Leu Ala Ala Val Leu Tyr Leu Asp Asp Glu Thr Ser Tyr Ser
                85                  90                  95

Glu Glu Arg Ala Asn Ala Pro Ile Gly Ser Gly Met Val Ser Gly Lys
            100                 105                 110

Leu Thr Asp Ala Val Asn Asp Gly Asp Glu Ser His Gln Asn Val Gly
        115                 120                 125

Thr Asp Ser Phe His Glu Ala Arg Pro Glu Asn Leu Ala Tyr Val Ile
    130                 135                 140

Tyr Thr Ser Gly Thr Thr Gly Lys Pro Lys Gly Val Met Ile Glu His
145                 150                 155                 160

Arg Ser Leu Val Asn Thr Ala Val Gly Tyr Arg Arg Glu Tyr Arg Leu
                165                 170                 175

Asp Gln Phe Pro Val Arg Leu Leu Gln Leu Ala Ser Phe Ser Phe Asp
            180                 185                 190

Val Phe Val Gly Asp Ile Ala Arg Thr Leu Tyr Asn Gly Gly Thr Met
        195                 200                 205

Val Ile Val Pro Lys Asp Asp Arg Ile Asp Pro Ser Arg Leu His His
    210                 215                 220

Trp Met Glu Arg Glu Val Thr Ile Phe Glu Ser Thr Pro Ala Leu
225                 230                 235                 240

Ile Val Pro Phe Leu Glu Tyr Val His Asp Gln Gln Leu Asp Met Ser
                245                 250                 255

Trp Met Glu Leu Leu Ile Thr Ser Ser Asp Ser Cys Ser Val Ala Asp
            260                 265                 270

Tyr Arg Thr Leu Gln Glu Arg Phe Gly Ser Leu Phe Arg Ile Ile Asn
```

```
                275                 280                 285
Ala Tyr Gly Val Thr Glu Ala Ile Asp Ser Ser Phe Tyr Asp Glu
    290                 295                 300
Glu Leu Ala Lys Leu Pro Gln Thr Gly His Val Pro Ile Gly Lys Ala
305                 310                 315                 320
Trp Leu Asn Ala Lys Phe Tyr Ile Val Asp Ala His Leu Asn Pro Val
                325                 330                 335
Pro Val Gly Val Met Gly Glu Leu Val Ile Gly Val Gly Val Ala
                340                 345                 350
Arg Gly Tyr Leu Asn Arg Pro Glu Leu Thr Glu Glu Lys Phe Val Asp
                355                 360                 365
Ser Pro Phe Ala Ala Gly Glu Arg Leu Tyr Arg Thr Gly Asp Leu Ala
    370                 375                 380
Arg Trp Met Glu Asp Gly Asn Val Asp Phe Ile Gly Arg Ile Asp Asn
385                 390                 395                 400
Gln Ala Lys Ile Arg Gly Tyr Arg Ile Glu Thr Gly Glu Ile Glu Ser
                405                 410                 415
Gln Leu Leu Arg Val Glu Gly Val Arg Glu Ala Val Val Leu Val Arg
                420                 425                 430
Ser Asp Ser Asn Gly Gln Lys Ala Leu Ser Ala Tyr Tyr Thr Ile Asp
    435                 440                 445
Gly Glu Leu Thr Ala Ala Asp Leu Lys Arg Ala Ile Ser Ser Glu Leu
    450                 455                 460
Pro Gly Tyr Met Ile Pro Ser Tyr Phe Val Glu Leu Glu Arg Leu Pro
465                 470                 475                 480
Leu Thr Pro Asn Gly Lys Ile Asp Arg Lys Glu Leu Pro Ala Pro Glu
                485                 490                 495
Gly Gly Ala Ser Ala Gly Arg Glu Tyr Val Ala Pro Arg Thr Glu Leu
                500                 505                 510
Glu Ala Lys Leu Val Ala Ile Trp Gln Asp Val Leu Gly Pro Ile Thr
                515                 520                 525
Ile Gly Val Thr Asp Asn Phe Phe Asp Leu Gly Gly His Ser Leu Arg
                530                 535                 540
Ala Thr Thr Leu Val Ser Lys Val His Lys Glu Leu
545                 550                 555

<210> SEQ ID NO 63
<211> LENGTH: 18
<212> TYPE: PRT
<213> ORGANISM: Polymyxa betae

<400> SEQUENCE: 63

Ser Val Asp Leu Pro Leu Arg Asp Val Phe Arg His Ser Thr Ile Glu
1               5                   10                  15

Ala Met

<210> SEQ ID NO 64
<211> LENGTH: 64
<212> TYPE: PRT
<213> ORGANISM: Polymyxa betae

<400> SEQUENCE: 64

Ala Glu Ala Ile Ser Gln Leu Glu Arg Gln Glu His Leu Ser Ile Pro
1               5                   10                  15

Val Leu Asp Lys Arg Asp Tyr Tyr Pro Leu Ser Ser Val Gln Lys Arg
                20                  25                  30
```

-continued

Leu Tyr Ile Gln Gln Gln Met Glu Gly Ala Glu Leu Ser Tyr Asn Met
         35                  40                  45

Ser Gly Met Thr Val Leu Val Gly Arg Leu Glu Arg Asn Gln Phe Glu
     50                  55                  60

<210> SEQ ID NO 65
<211> LENGTH: 21
<212> TYPE: PRT
<213> ORGANISM: Polymyxa betae

<400> SEQUENCE: 65

Ala Ala Leu Lys Gly Leu Ile Ala Arg His Glu Ile Leu Arg Thr Gly
 1               5                  10                  15

Phe Glu Met Val Asp
             20

<210> SEQ ID NO 66
<211> LENGTH: 377
<212> TYPE: PRT
<213> ORGANISM: Polymyxa betae

<400> SEQUENCE: 66

Gly Glu Pro Val Gln Arg Ile Tyr Pro Asp Leu Lys Phe Ala Val Glu
 1               5                  10                  15

Tyr Thr Lys Ala Met Glu Ser Glu Thr Lys Ser Ile Val Asp Gly Phe
             20                  25                  30

Val Arg Val Phe Asp Leu Glu Arg Pro Leu Leu Arg Val Gly Leu
         35                  40                  45

Val Glu Met Glu Ala Glu Arg His Leu Leu Met Leu Asp Ile His His
     50                  55                  60

Ile Val Thr Asp Gly Met Ser Met Gly Ile Phe Val Glu Glu Leu Leu
 65                  70                  75                  80

Arg Leu Tyr Asn Gly Glu Thr Leu Glu Pro Leu Arg Ile Gln Tyr Lys
                 85                  90                  95

Glu Phe Ala Ala Trp Gln Gln Ser Glu Pro Val Lys Glu Arg Leu Lys
            100                 105                 110

Arg Gln Glu Ala Tyr Trp Leu Asp Val Leu Glu Gly Glu Leu Pro Thr
        115                 120                 125

Leu Glu Leu Pro Thr Asp Phe Val Arg Pro Ala Ala Arg Ser Phe Glu
    130                 135                 140

Gly Asp Val Leu Pro Phe Ser Ile Asp Lys Gln Met Thr Asp Ser Leu
145                 150                 155                 160

Gln Arg Ile Ala Asp Glu Asn Gly Ala Thr Leu Tyr Met Val Leu Leu
                165                 170                 175

Ala Ala Tyr Ser Ile Leu Leu Ser Lys Tyr Ser Gly Gln Glu Asp Phe
            180                 185                 190

Ile Val Gly Thr Pro Val Ser Gly Arg Thr His Ala Asp Leu Glu Pro
        195                 200                 205

Leu Ile Gly Met Phe Val Asn Thr Leu Ala Ile Arg His Tyr Pro Ser
    210                 215                 220

Gly Glu Lys Thr Phe Leu Ala Tyr Leu Asn Glu Val Lys Glu Thr Met
225                 230                 235                 240

Leu Gly Ala Tyr Glu His Gln Asp Tyr Pro Phe Glu Glu Leu Val Lys
                245                 250                 255

Lys Leu Gln Ala Pro Arg Asp Gln Ser Arg Asn Pro Val Phe Asp Val
            260                 265                 270

```
                                    -continued

Met Phe Ala Leu Glu Thr Lys Glu Asp Asn Val Gln Ser Phe Gly Asp
            275                 280                 285

Ile Lys Ile Glu Ser Tyr Pro Glu Thr His Thr Val Ser Gln Phe Asp
        290             295             300

Leu Thr Leu Val Ile Ser Leu Leu Asp Glu Gly Met Asn Gly Gln Phe
305                 310                 315                 320

Glu Tyr Ala Thr Lys Leu Phe Thr Arg Asn Leu Ile Asp Asn Phe Ala
                325                 330                 335

Gln Asp Leu Leu Val Ile Ile Thr Gln Ile Cys Glu Gln Pro Ser Ala
            340                 345                 350

Leu Leu Lys Asp Ile Ser Leu Asn Gly Gln Ser Glu Gln Glu Gln Asp
        355                 360                 365

Val Leu Glu Ala Ile Asp Ile Ile Phe
    370                 375
```